US011583172B2

(12) United States Patent
Petroff et al.

(10) Patent No.: US 11,583,172 B2
(45) Date of Patent: Feb. 21, 2023

(54) IMAGING SYSTEM INCLUDES IMAGING PROBE AND DELIVERY DEVICES

(71) Applicant: GENTUITY, LLC, Sudbury, MA (US)

(72) Inventors: Christopher Petroff, Groton, MA (US); Christopher Petersen, Carlisle, MA (US); David W. Kolstad, Carlisle, MA (US)

(73) Assignee: Gentuity, LLC, Sudbury, MA (US)

( * ) Notice: Subject to any disclaimer, the term of this patent is extended or adjusted under 35 U.S.C. 154(b) by 0 days.

(21) Appl. No.: 17/350,021

(22) Filed: Jun. 17, 2021

(65) Prior Publication Data
US 2022/0142464 A1 May 12, 2022

Related U.S. Application Data

(63) Continuation of application No. 16/820,991, filed on Mar. 17, 2020, now Pat. No. 11,064,873, which is a
(Continued)

(51) Int. Cl.
A61B 1/05 (2006.01)
A61B 1/06 (2006.01)
(Continued)

(52) U.S. Cl.
CPC .............. A61B 1/05 (2013.01); A61B 1/0676 (2013.01); A61B 5/0066 (2013.01);
(Continued)

(58) Field of Classification Search
CPC ....... A61B 1/05; A61B 1/0676; A61B 5/0066; A61B 5/0084; A61B 17/00234;
(Continued)

(56) References Cited

U.S. PATENT DOCUMENTS 4,554,929 A 11/1985 Samson et al.
4,566,330 A 1/1986 Fujii et al.
(Continued)

FOREIGN PATENT DOCUMENTS

AU 2014200116 1/2014
CN 1684624 10/2005
(Continued)

OTHER PUBLICATIONS

Extended European Search Report dated Jun. 8, 2022 issued in related European Application No. 21217738.0.
(Continued)

Primary Examiner — Seung C Sohn
(74) Attorney, Agent, or Firm — Onello & Mello, LLP

(57) ABSTRACT

An imaging system is provided comprising an imaging probe and at least one delivery device. The imaging probe comprises an elongate shaft, a rotatable optical core and an optical assembly. The elongate shaft comprises a proximal end, a distal portion, and a lumen extending between the proximal end and the distal portion. The rotatable optical core is positioned within the lumen of the elongate shaft and comprises a proximal end and a distal end. The rotatable optical core is configured to optically and mechanically connect with an interface unit. The optical assembly is positioned in the elongate shaft distal portion and proximate the rotatable optical core distal end. The optical assembly is configured to direct light to tissue and collect reflected light from the tissue. The imaging probe is constructed and arranged to collect image data from a patient site. The at least one delivery device is constructed and arranged to slidingly engage the imaging probe. Methods of introducing the imaging probe and the at least one delivery catheter into a patient are also provided.

25 Claims, 13 Drawing Sheets

Related U.S. Application Data continuation of application No. 15/751,570, filed as application No. PCT/US2016/049415 on Aug. 30, 2016, now Pat. No. 10,631,718.

(60) Provisional application No. 62/368,387, filed on Jul. 29, 2016, provisional application No. 62/212,173, filed on Aug. 31, 2015.

(51) Int. Cl.
| | | |
|---|---|---|
| *A61B 17/00* | (2006.01) | |
| *A61B 5/00* | (2006.01) | |
| *H04N 5/225* | (2006.01) | |
| *A61B 8/06* | (2006.01) | |
| *A61B 8/12* | (2006.01) | |
| *A61B 6/12* | (2006.01) | |
| *A61B 6/00* | (2006.01) | |
| *A61B 5/01* | (2006.01) | |
| *A61B 5/021* | (2006.01) | |

(52) U.S. Cl.
CPC ...... *A61B 5/0084* (2013.01); *A61B 17/00234* (2013.01); *A61B 5/0073* (2013.01); *A61B 5/01* (2013.01); *A61B 5/021* (2013.01); *A61B 6/12* (2013.01); *A61B 6/487* (2013.01); *A61B 8/06* (2013.01); *A61B 8/12* (2013.01); *A61B 2017/0034* (2013.01); *A61B 2017/00336* (2013.01); *A61B 2562/0233* (2013.01); *H04N 5/2256* (2013.01); *H04N 2005/2255* (2013.01)

(58) Field of Classification Search
CPC ......... A61B 5/0073; A61B 5/01; A61B 5/021; A61B 6/12; A61B 6/487; A61B 8/06; A61B 8/12; A61B 2017/00336; A61B 2017/0034; A61B 2562/0233; H04N 5/2256; H04N 2005/2255
See application file for complete search history.

(56) References Cited

U.S. PATENT DOCUMENTS

| | | |
|---|---|---|
| 4,583,184 A | 4/1986 | Murase |
| 4,594,895 A | 6/1986 | Fujii |
| 4,597,292 A | 7/1986 | Fujii et al. |
| 4,646,748 A | 3/1987 | Fujii et al. |
| 4,753,248 A | 6/1988 | Engler et al. |
| 4,957,482 A | 9/1990 | Shiber |
| 4,961,427 A | 10/1990 | Namekawa et al. |
| 5,002,059 A | 3/1991 | Crowley et al. |
| 5,039,193 A | 8/1991 | Snow et al. |
| 5,058,587 A | 10/1991 | Kohno et al. |
| 5,118,405 A | 6/1992 | Kaneko et al. |
| 5,127,405 A | 7/1992 | Alcala et al. |
| 5,143,075 A | 9/1992 | Ishizuka |
| 5,151,603 A | 9/1992 | Nakamura |
| 5,152,277 A | 10/1992 | Honda et al. |
| 5,158,086 A | 10/1992 | Brown et al. |
| 5,212,671 A | 5/1993 | Fujii et al. |
| 5,219,335 A | 6/1993 | Willard et al. |
| 5,321,501 A | 6/1994 | Swanson et al. |
| 5,331,309 A | 7/1994 | Sakai |
| 5,383,467 A | 1/1995 | Auer et al. |
| 5,443,781 A | 8/1995 | Saab |
| 5,456,245 A | 10/1995 | Bornhop et al. |
| 5,459,570 A | 10/1995 | Swanson et al. |
| 5,554,139 A | 9/1996 | Okajima |
| 5,568,314 A | 10/1996 | Omori et al. |
| 5,568,503 A | 10/1996 | Omori |
| 5,644,427 A | 7/1997 | Omori et al. |
| 5,647,359 A | 7/1997 | Kohno et al. |
| 5,649,897 A | 7/1997 | Nakamura et al. |
| 5,689,316 A | 11/1997 | Hattori et al. |
| 5,738,100 A | 4/1998 | Yagami et al. |
| 5,745,163 A | 4/1998 | Nakamura et al. |
| 5,774,175 A | 6/1998 | Hattori |
| 5,774,261 A | 6/1998 | Omori et al. |
| 5,793,341 A | 8/1998 | Omori et al. |
| 5,818,399 A | 10/1998 | Omori et al. |
| 5,860,923 A | 1/1999 | Lenker et al. |
| 5,976,017 A | 11/1999 | Omori et al. |
| 5,999,591 A | 12/1999 | Kobayashi et al. |
| 6,011,580 A | 1/2000 | Hattori et al. |
| 6,011,809 A | 1/2000 | Tosaka |
| 6,019,507 A | 2/2000 | Takaki |
| 6,019,737 A | 2/2000 | Murata |
| 6,033,383 A | 3/2000 | Ginsburg |
| 6,036,682 A | 3/2000 | Lange et al. |
| 6,052,613 A | 4/2000 | Takaki |
| 6,064,684 A | 5/2000 | Yoon et al. |
| 6,069,698 A | 5/2000 | Ozawa et al. |
| 6,115,058 A | 9/2000 | Omori et al. |
| 6,134,003 A | 10/2000 | Tearney et al. |
| 6,160,826 A | 12/2000 | Swanson et al. |
| 6,165,127 A | 12/2000 | Crowley |
| 6,191,862 B1 | 2/2001 | Swanson et al. |
| 6,208,887 B1 | 3/2001 | Clarke |
| 6,217,828 B1 | 4/2001 | Bretscher et al. |
| 6,283,632 B1 | 9/2001 | Takaki |
| 6,296,608 B1 | 10/2001 | Daniels et al. |
| 6,309,358 B1 | 10/2001 | Okubo |
| 6,341,036 B1 | 1/2002 | Tearney et al. |
| 6,364,841 B1 | 4/2002 | White et al. |
| 6,383,209 B1 | 5/2002 | Crowley |
| 6,445,939 B1 | 9/2002 | Swanson et al. |
| 6,449,500 B1 | 9/2002 | Asai et al. |
| 6,471,656 B1 | 10/2002 | Shalman et al. |
| 6,485,413 B1 | 11/2002 | Boppart et al. |
| 6,485,482 B1 | 11/2002 | Belef |
| 6,520,959 B1 | 2/2003 | Iwahashi et al. |
| 6,530,921 B1 | 3/2003 | Maki |
| 6,547,757 B1 | 4/2003 | Kranz et al. |
| 6,549,687 B1 | 4/2003 | Kochergin et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,570,893 B1 | 5/2003 | Libatique et al. |
| 6,572,553 B2 | 6/2003 | Crowley |
| 6,577,391 B1 | 6/2003 | Faupel et al. |
| 6,579,286 B1 | 6/2003 | Maki et al. |
| 6,589,233 B1 | 7/2003 | Maki |
| 6,601,459 B1 | 8/2003 | Jenni |
| 6,607,526 B1 | 8/2003 | Maki |
| 6,615,072 B1 | 9/2003 | Izatt et al. |
| 6,654,630 B2 | 11/2003 | Zuluaga et al. |
| 6,658,278 B2 | 12/2003 | Gruhl |
| 6,879,851 B2 | 4/2005 | McNamara et al. |
| 6,881,194 B2 | 4/2005 | Miyata et al. |
| 6,891,984 B2 | 5/2005 | Petersen et al. |
| 6,904,197 B2 | 6/2005 | Bhagavatula et al. |
| 6,904,199 B2 | 6/2005 | Zuluaga |
| 6,925,320 B2 | 8/2005 | Gruhl |
| 6,940,885 B1 | 9/2005 | Cheng et al. |
| 7,003,184 B2 | 2/2006 | Ronnekleiv et al. |
| 7,016,024 B2 | 3/2006 | Bridge et al. |
| 7,022,118 B2 | 4/2006 | Ariura et al. |
| 7,029,436 B2 | 4/2006 | Iizuka et al. |
| 7,099,358 B1 | 8/2006 | Chong |
| 7,134,994 B2 | 11/2006 | Alpert et al. |
| 7,155,272 B2 | 12/2006 | Yamaguchi et al. |
| 7,231,243 B2 | 6/2007 | Tearney et al. |
| 7,241,286 B2 | 7/2007 | Atlas |
| 7,365,859 B2 | 4/2008 | Yun et al. |
| 7,366,376 B2 | 4/2008 | Shishkov et al. |
| 7,382,949 B2 | 6/2008 | Bouma et al. |
| 7,450,980 B2 | 11/2008 | Kawanishi |
| 7,551,293 B2 | 6/2009 | Yelin et al. |
| 7,567,349 B2 | 7/2009 | Tearney et al. |
| 7,625,366 B2 | 12/2009 | Atlas |
| 7,682,089 B2 | 3/2010 | Rohlen |
| 7,691,061 B2 | 4/2010 | Hirota |

(56) References Cited

U.S. PATENT DOCUMENTS

| | | | |
|---|---|---|---|
| 7,711,413 | B2 | 5/2010 | Feldman et al. |
| 7,724,786 | B2 | 5/2010 | Bouma et al. |
| 7,733,497 | B2 | 6/2010 | Yun et al. |
| 7,738,941 | B2 | 6/2010 | Hirota |
| 7,740,408 | B2 | 6/2010 | Irisawa |
| 7,742,173 | B2 | 6/2010 | Yun et al. |
| 7,761,139 | B2 | 7/2010 | Tearney et al. |
| 7,783,337 | B2 | 8/2010 | Feldman et al. |
| 7,794,230 | B2 | 9/2010 | Lakin et al. |
| 7,803,141 | B2 | 9/2010 | Epstein et al. |
| 7,812,961 | B2 | 10/2010 | Yamaguchi |
| 7,813,609 | B2 | 10/2010 | Petersen et al. |
| 7,815,632 | B2 | 10/2010 | Hayakawa et al. |
| 7,843,572 | B2 | 11/2010 | Tearney et al. |
| 7,847,949 | B2 | 12/2010 | Tearney et al. |
| 7,848,791 | B2 | 12/2010 | Schmitt et al. |
| 7,872,759 | B2 | 1/2011 | Tearney et al. |
| 7,905,838 | B2 | 3/2011 | Hirota |
| 7,911,621 | B2 | 3/2011 | Motaghiannezam et al. |
| 7,916,387 | B2 | 3/2011 | Schmitt |
| 7,920,271 | B2 | 4/2011 | Vakoc et al. |
| 7,922,650 | B2 | 4/2011 | McWeeney et al. |
| 7,926,562 | B2 | 4/2011 | Poitzsch et al. |
| 7,935,060 | B2 | 5/2011 | Schmitt et al. |
| 7,940,397 | B2 | 5/2011 | Masuda |
| 7,969,578 | B2 | 6/2011 | Yun et al. |
| 7,982,879 | B2 | 7/2011 | Desjardins et al. |
| 8,018,598 | B2 | 9/2011 | Cense et al. |
| 8,029,446 | B2 | 10/2011 | Horiike et al. |
| 8,029,447 | B2 | 10/2011 | Kanz et al. |
| 8,032,200 | B2 | 10/2011 | Tearney et al. |
| 8,040,524 | B2 | 10/2011 | Ozawa |
| 8,047,996 | B2 | 11/2011 | Goodnow et al. |
| 8,049,900 | B2 | 11/2011 | Kemp et al. |
| 8,052,605 | B2 | 11/2011 | Muller et al. |
| 8,055,107 | B2 | 11/2011 | Masuda |
| 8,081,316 | B2 | 12/2011 | De Boer et al. |
| 8,094,319 | B2 | 1/2012 | Onimura |
| 8,100,833 | B2 | 1/2012 | Hirota |
| 8,108,032 | B2 | 1/2012 | Onimura et al. |
| 8,116,605 | B2 | 2/2012 | Petersen et al. |
| 8,125,648 | B2 | 2/2012 | Milner et al. |
| 8,149,418 | B2 | 4/2012 | Tearney et al. |
| 8,157,741 | B2 | 4/2012 | Hirota |
| 8,157,742 | B2 | 4/2012 | Taylor |
| 8,174,702 | B2 | 5/2012 | Tearney et al. |
| 8,206,372 | B2 | 6/2012 | Larson et al. |
| 8,206,377 | B2 | 6/2012 | Petroff |
| 8,208,995 | B2 | 6/2012 | Tearney et al. |
| 8,231,516 | B2 | 7/2012 | Maschke |
| 8,241,196 | B2 | 8/2012 | Scibona |
| 8,289,522 | B2 | 10/2012 | Fearney et al. |
| RE43,875 | E | 12/2012 | Shishkov et al. |
| 8,322,932 | B2 | 12/2012 | Irisawa |
| 8,325,419 | B2 | 12/2012 | Schmitt |
| 8,337,379 | B2 | 12/2012 | Fletcher et al. |
| 8,339,592 | B2 | 12/2012 | Hlavinka et al. |
| 8,346,348 | B2 | 1/2013 | Onimura |
| 8,351,665 | B2 | 1/2013 | Tearney et al. |
| 8,355,138 | B2 | 1/2013 | Yun et al. |
| 8,384,907 | B2 | 2/2013 | Tearney et al. |
| 8,384,909 | B2 | 2/2013 | Yun et al. |
| 8,412,312 | B2 | 4/2013 | Judell et al. |
| 8,414,496 | B2 | 4/2013 | Goodnow et al. |
| 8,449,439 | B2 | 5/2013 | Fletcher et al. |
| 8,449,468 | B2 | 5/2013 | Petersen et al. |
| 8,452,371 | B2 | 5/2013 | Feldman et al. |
| 8,473,037 | B2 | 6/2013 | Irisawa |
| 8,473,073 | B2 | 6/2013 | Vardiman |
| 8,478,384 | B2 | 7/2013 | Schmitt et al. |
| 8,478,387 | B2 | 7/2013 | Xu |
| 8,493,567 | B2 | 7/2013 | Inoue |
| 8,501,015 | B2 | 8/2013 | Fletcher et al. |
| 8,503,844 | B2 | 8/2013 | Petersen et al. |
| 8,531,676 | B2 | 9/2013 | Condit et al. |
| 8,535,210 | B2 | 9/2013 | Kolenbrander et al. |
| 8,556,820 | B2 | 10/2013 | Alpert et al. |
| 8,559,012 | B2 | 10/2013 | Tearney et al. |
| 8,581,643 | B1 | 11/2013 | Schmitt |
| 8,582,109 | B1 | 11/2013 | Schmitt |
| 8,582,619 | B2 | 11/2013 | Adler |
| 8,582,934 | B2 | 11/2013 | Adler et al. |
| 8,585,592 | B2 | 11/2013 | Luevano et al. |
| 8,593,619 | B2 | 11/2013 | Colice et al. |
| 8,593,641 | B2 | 11/2013 | Kemp et al. |
| 8,618,032 | B2 | 12/2013 | Kurita |
| 8,626,453 | B2 | 1/2014 | Myoujou et al. |
| 8,636,659 | B2 | 1/2014 | Alpert et al. |
| 8,676,013 | B2 | 3/2014 | Bouma et al. |
| 8,676,299 | B2 | 3/2014 | Schmitt et al. |
| 8,687,201 | B2 | 4/2014 | Adler |
| 8,705,046 | B2 | 4/2014 | Yun et al. |
| 8,712,506 | B2 | 4/2014 | Courtney et al. |
| 8,753,281 | B2 | 6/2014 | Schmitt et al. |
| 8,760,663 | B2 | 6/2014 | Tearney et al. |
| 8,761,469 | B2 | 6/2014 | Kemp et al. |
| 8,786,336 | B1 | 7/2014 | Schmitt |
| 8,804,126 | B2 | 8/2014 | Tearney et al. |
| 8,808,186 | B2 | 8/2014 | Fruland et al. |
| 8,810,901 | B2 | 8/2014 | Huber et al. |
| 8,825,142 | B2 | 9/2014 | Suehara |
| 8,827,926 | B2 | 9/2014 | Kinoshita et al. |
| 8,831,321 | B1 | 9/2014 | Elbasiony |
| 8,868,159 | B2 | 10/2014 | Onimura |
| 8,885,171 | B2 | 11/2014 | Watanabe et al. |
| 8,896,838 | B2 | 11/2014 | Tearney et al. |
| 8,902,941 | B2 | 12/2014 | Schmitt |
| 8,909,324 | B2 | 12/2014 | Furuichi |
| 8,911,357 | B2 | 12/2014 | Omori |
| 8,926,590 | B2 | 1/2015 | Petroff |
| 8,928,889 | B2 | 1/2015 | Tearney et al. |
| 8,945,526 | B2 | 2/2015 | Akitsu et al. |
| 8,948,228 | B2 | 2/2015 | Adler |
| 8,948,613 | B2 | 2/2015 | Schmitt et al. |
| 8,953,911 | B1 | 2/2015 | Xu et al. |
| 8,983,582 | B2 | 3/2015 | Webler |
| 8,989,849 | B2 * | 3/2015 | Milner ............... A61M 25/0074 600/478 |
| 8,994,803 | B2 | 3/2015 | Kaneko |
| 8,996,099 | B2 | 3/2015 | Feldman et al. |
| 8,998,797 | B2 | 4/2015 | Omori |
| 9,007,696 | B2 | 4/2015 | Petersen et al. |
| 9,033,890 | B2 | 5/2015 | Furuichi |
| 9,036,966 | B2 | 5/2015 | Bhagavatula et al. |
| 9,039,626 | B2 | 5/2015 | Courtney |
| 9,060,689 | B2 | 6/2015 | Tearney et al. |
| 9,069,396 | B2 | 6/2015 | Adler et al. |
| 9,081,148 | B2 | 7/2015 | Tearney et al. |
| 9,084,532 | B2 | 7/2015 | Horiike |
| 9,087,368 | B2 | 7/2015 | Tearney et al. |
| 9,091,524 | B2 | 7/2015 | Adler et al. |
| 9,101,298 | B2 | 8/2015 | Hossack et al. |
| 9,107,682 | B2 | 8/2015 | Scheller et al. |
| 9,107,687 | B2 | 8/2015 | Kinoshita et al. |
| 9,121,926 | B2 | 9/2015 | Nair et al. |
| 9,131,850 | B2 | 9/2015 | Liu et al. |
| 9,138,147 | B2 | 9/2015 | Schmitt et al. |
| 9,164,240 | B2 | 10/2015 | Schmitt et al. |
| 9,168,003 | B2 | 10/2015 | Suzuki et al. |
| 9,173,572 | B2 | 11/2015 | Colice et al. |
| 9,173,591 | B2 | 11/2015 | Elbasiony et al. |
| 9,194,690 | B2 | 11/2015 | Bhagavatula et al. |
| 9,207,064 | B2 | 12/2015 | Inoue |
| 9,226,660 | B2 | 1/2016 | De Boer et al. |
| 9,226,665 | B2 | 1/2016 | Tearney et al. |
| 9,254,102 | B2 | 2/2016 | Tearney et al. |
| 9,289,127 | B2 | 3/2016 | Mitsuhashi et al. |
| 9,289,582 | B2 | 3/2016 | Suehara |
| 9,295,450 | B2 | 3/2016 | Furuichi et al. |
| 9,295,455 | B2 | 3/2016 | Karino et al. |
| 9,301,687 | B2 | 4/2016 | Kemp |
| 9,304,121 | B2 | 4/2016 | Tearney et al. |
| 9,322,639 | B2 | 4/2016 | Watanabe et al. |
| 9,326,789 | B2 | 5/2016 | Fruland et al. |

(56) References Cited

U.S. PATENT DOCUMENTS

| | | |
|---|---|---|
| 9,330,092 B2 | 5/2016 | Vakoc et al. |
| 9,339,173 B2 | 5/2016 | McWeeney et al. |
| 9,339,348 B2 | 5/2016 | Davies et al. |
| 9,345,864 B2 | 5/2016 | Suehara |
| 9,347,765 B2 | 5/2016 | Kemp et al. |
| 9,351,698 B2 | 5/2016 | Dascal et al. |
| 9,357,923 B2 | 6/2016 | Courtney et al. |
| 9,375,148 B2 | 6/2016 | Senoo |
| 9,375,158 B2 | 6/2016 | Vakoc et al. |
| 9,375,164 B2 | 6/2016 | Tolkowsky et al. |
| 9,377,290 B2 | 6/2016 | Yun et al. |
| 9,404,731 B2 | 8/2016 | Adler et al. |
| 9,408,539 B2 | 8/2016 | Tearney et al. |
| 9,417,052 B2 | 8/2016 | Adler |
| 9,435,736 B2 | 9/2016 | Kolenbrander et al. |
| 9,435,956 B1 | 9/2016 | Xu et al. |
| 9,439,570 B2 | 9/2016 | Vertikov |
| 9,441,948 B2 | 9/2016 | Vakoc et al. |
| 9,462,950 B2 | 10/2016 | Xu |
| 9,464,883 B2 | 10/2016 | Swanson et al. |
| 9,488,464 B1 | 11/2016 | Schmitt |
| 9,507,074 B2 | 11/2016 | Zhu et al. |
| 9,513,276 B2 | 12/2016 | Tearney et al. |
| 9,526,424 B2 | 12/2016 | Judell et al. |
| 9,566,752 B2 | 2/2017 | Hartkorn |
| 9,572,495 B2 | 2/2017 | Schmitt et al. |
| 9,572,496 B2 | 2/2017 | Furuichi et al. |
| 9,605,942 B2 | 3/2017 | Staloff |
| 9,610,064 B2 | 4/2017 | Adler et al. |
| 9,615,771 B2 | 4/2017 | Furuichi et al. |
| 9,622,706 B2 | 4/2017 | Dick et al. |
| 9,638,862 B2 | 5/2017 | Bhagavatula et al. |
| 9,642,531 B2 | 5/2017 | Tearney et al. |
| 9,645,322 B2 | 5/2017 | Murashima et al. |
| 9,646,377 B2 | 5/2017 | Tearney et al. |
| 9,659,375 B2 | 5/2017 | Zagrodsky et al. |
| 9,702,687 B2 | 7/2017 | Schmitt |
| 9,702,762 B2 | 7/2017 | Friedman et al. |
| 9,704,240 B2 | 7/2017 | Lam et al. |
| 9,710,891 B2 | 7/2017 | Sakamoto |
| 9,730,613 B2 | 8/2017 | Stigall et al. |
| 9,763,623 B2 | 9/2017 | Tearney et al. |
| 9,778,020 B2 | 10/2017 | Tumlinson et al. |
| 9,788,790 B2 | 10/2017 | Black et al. |
| 9,808,303 B2 | 11/2017 | Ryba et al. |
| 9,812,846 B2 | 11/2017 | Yun et al. |
| 9,833,221 B2 | 12/2017 | Hutchins et al. |
| 9,836,835 B2 | 12/2017 | Furuichi et al. |
| 9,843,159 B2 | 12/2017 | Cable et al. |
| 9,855,020 B2 | 1/2018 | Nair et al. |
| 9,858,387 B2 | 1/2018 | Lavi et al. |
| 9,864,140 B2 | 1/2018 | Adler et al. |
| 9,872,665 B2 | 1/2018 | Okubo et al. |
| 9,891,044 B2 | 2/2018 | Tu et al. |
| 9,897,538 B2 | 2/2018 | Tearney et al. |
| 9,907,527 B2 | 3/2018 | Dascal et al. |
| 9,933,244 B2 | 4/2018 | Krol et al. |
| 9,940,723 B2 | 4/2018 | Gopinath et al. |
| 9,943,233 B2 | 4/2018 | Lavi et al. |
| 9,962,127 B2 | 5/2018 | Wang et al. |
| 9,980,648 B2 | 5/2018 | Itoh et al. |
| 9,983,356 B2 | 5/2018 | Schmitt et al. |
| 9,986,938 B2 | 6/2018 | Tu et al. |
| 9,989,945 B2 | 6/2018 | Adler et al. |
| 9,996,921 B2 | 6/2018 | Ambwani et al. |
| 10,004,400 B2 | 6/2018 | Nakamoto et al. |
| 10,004,863 B2 | 6/2018 | Vazales et al. |
| 10,006,753 B2 | 6/2018 | Schmitt et al. |
| 10,028,725 B2 | 7/2018 | Petroff |
| 10,089,755 B2 | 10/2018 | Griffin et al. |
| 10,092,188 B2 | 10/2018 | Jaffer et al. |
| 10,109,058 B2 | 10/2018 | Ambwani et al. |
| 10,124,153 B2 | 11/2018 | Feig et al. |
| 10,140,712 B2 | 11/2018 | Ambwani |
| 10,162,114 B2 | 12/2018 | Bhagavatula et al. |
| 10,172,582 B2 | 1/2019 | Dascal et al. |
| 10,186,056 B2 | 1/2019 | Senzig et al. |
| 10,207,124 B2 | 2/2019 | Shimizu et al. |
| 10,213,109 B2 | 2/2019 | Itoh et al. |
| 10,213,186 B2 | 2/2019 | Inoue et al. |
| 10,219,780 B2 | 3/2019 | Castella et al. |
| 10,222,956 B2 | 3/2019 | Gopinath et al. |
| 10,238,349 B2 | 3/2019 | Furuichi et al. |
| 10,261,223 B2 | 4/2019 | Tearney et al. |
| 10,271,818 B2 | 4/2019 | Kobayashi |
| 10,285,568 B2 | 5/2019 | Tearney et al. |
| 10,327,726 B2 | 6/2019 | Dascal et al. |
| 10,331,099 B2 | 6/2019 | Adler et al. |
| 10,335,039 B2 | 7/2019 | Xu |
| 10,338,795 B2 | 7/2019 | Gopinath et al. |
| 10,342,502 B2 | 7/2019 | Dascal et al. |
| 10,387,013 B2 | 8/2019 | Jamello |
| 10,453,190 B2 | 10/2019 | Griffin |
| 10,453,196 B2 | 10/2019 | Ambwani |
| 10,463,254 B2 | 11/2019 | Tearney et al. |
| 10,499,813 B2 | 12/2019 | Adler |
| 10,529,093 B2 | 1/2020 | Griffin et al. |
| 10,551,251 B2 | 2/2020 | Friedman et al. |
| 10,593,037 B2 | 3/2020 | Gopinath |
| 10,631,754 B2 | 4/2020 | Gopinath |
| 10,646,198 B2 | 5/2020 | Peterson et al. |
| 10,648,918 B2 | 5/2020 | Schmitt |
| 10,687,777 B2 | 6/2020 | Dascal et al. |
| 10,713,786 B2 | 7/2020 | Ambwani et al. |
| 10,729,376 B2 | 8/2020 | Courtney |
| 10,792,012 B2 | 10/2020 | Hutchins et al. |
| 10,806,421 B2 | 10/2020 | Keller |
| 10,878,572 B2 | 12/2020 | Gopinath et al. |
| 10,902,599 B2 | 1/2021 | Ambwani et al. |
| 2002/0041724 A1 | 4/2002 | Ronnekleiv et al. |
| 2002/0072880 A1 | 6/2002 | Svanerudh et al. |
| 2002/0099289 A1 | 7/2002 | Crowley |
| 2002/0131049 A1 | 9/2002 | Schmitt |
| 2002/0151823 A1 | 10/2002 | Miyata et al. |
| 2002/0163622 A1 | 11/2002 | Magnin et al. |
| 2002/0183601 A1 | 12/2002 | Tearney et al. |
| 2002/0183622 A1 | 12/2002 | Zuluaga et al. |
| 2002/0188204 A1 | 12/2002 | McNamara et al. |
| 2002/0198457 A1 | 12/2002 | Tearney et al. |
| 2003/0004417 A1 | 1/2003 | Ariura et al. |
| 2003/0013952 A1 | 1/2003 | Iizuka et al. |
| 2003/0073909 A1 | 4/2003 | Gruhl |
| 2003/0081875 A1 | 5/2003 | Kochergin et al. |
| 2003/0165291 A1 | 9/2003 | Bhagavatula et al. |
| 2003/0216621 A1 | 11/2003 | Alpert et al. |
| 2004/0017961 A1 | 1/2004 | Petersen et al. |
| 2004/0034290 A1 | 2/2004 | Zuluaga |
| 2004/0082861 A1 | 4/2004 | Gruhl |
| 2004/0092913 A1 | 5/2004 | Hennings et al. |
| 2004/0215166 A1 | 10/2004 | Atlas |
| 2005/0004453 A1 | 1/2005 | Tearney et al. |
| 2005/0038406 A1 | 2/2005 | Epstein et al. |
| 2005/0101870 A1 | 5/2005 | Yamaguchi et al. |
| 2005/0128488 A1 | 6/2005 | Yelin et al. |
| 2005/0187422 A1 | 8/2005 | Maschke |
| 2005/0201662 A1 | 9/2005 | Petersen et al. |
| 2005/0221277 A1 | 10/2005 | Kawanishi |
| 2005/0259242 A1 | 11/2005 | Bridge et al. |
| 2005/0272975 A1 | 12/2005 | McWeeney et al. |
| 2005/0288583 A1 | 12/2005 | Hirota |
| 2006/0039004 A1 | 2/2006 | De Boer et al. |
| 2006/0055936 A1 | 3/2006 | Yun et al. |
| 2006/0058622 A1 | 3/2006 | Tearney et al. |
| 2006/0067620 A1 | 3/2006 | Shishkov et al. |
| 2006/0091566 A1 | 5/2006 | Yang et al. |
| 2006/0093276 A1 | 5/2006 | Bouma et al. |
| 2006/0095065 A1 | 5/2006 | Tanimura et al. |
| 2006/0135870 A1 | 6/2006 | Webler |
| 2006/0166176 A1 | 7/2006 | Lakin et al. |
| 2006/0227333 A1 | 10/2006 | Tearney et al. |
| 2006/0241484 A1 | 10/2006 | Horiike et al. |
| 2006/0241493 A1 | 10/2006 | Feldman et al. |
| 2006/0241503 A1 | 10/2006 | Schmitt et al. |
| 2006/0244973 A1 | 11/2006 | Yun et al. |

(56) References Cited

U.S. PATENT DOCUMENTS

| | | |
|---|---|---|
| 2006/0247743 A1 | 11/2006 | Hayakawa et al. |
| 2006/0279742 A1 | 12/2006 | Tearney et al. |
| 2007/0012886 A1 | 1/2007 | Tearney et al. |
| 2007/0015969 A1 | 1/2007 | Feldman et al. |
| 2007/0035743 A1 | 2/2007 | Vakoc et al. |
| 2007/0038040 A1 | 2/2007 | Cense et al. |
| 2007/0038274 A1 | 2/2007 | Ishii et al. |
| 2007/0060822 A1 | 3/2007 | Alpert et al. |
| 2007/0073162 A1 | 3/2007 | Tearney et al. |
| 2007/0081236 A1 | 4/2007 | Tearney et al. |
| 2007/0106155 A1 | 5/2007 | Goodnow et al. |
| 2007/0121196 A1 | 5/2007 | Tearney et al. |
| 2007/0201033 A1 | 8/2007 | Desjardins et al. |
| 2007/0229801 A1 | 10/2007 | Tearney et al. |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0233396 A1 | 10/2007 | Tearney et al. |
| 2007/0236700 A1 | 10/2007 | Yun et al. |
| 2007/0244391 A1 | 10/2007 | Hirota |
| 2007/0260198 A1 | 11/2007 | Atlas |
| 2008/0002211 A1 | 1/2008 | Park et al. |
| 2008/0004530 A1 | 1/2008 | Feldman et al. |
| 2008/0007734 A1 | 1/2008 | Park et al. |
| 2008/0019908 A1 | 1/2008 | Akitsu et al. |
| 2008/0021275 A1 | 1/2008 | Tearney et al. |
| 2008/0045394 A1 | 2/2008 | Fletcher et al. |
| 2008/0049232 A1 | 2/2008 | Vakoc et al. |
| 2008/0161696 A1 | 7/2008 | Schmitt et al. |
| 2008/0165366 A1 | 7/2008 | Schmitt |
| 2008/0177139 A1 | 7/2008 | Courtney et al. |
| 2008/0181263 A1 | 7/2008 | Bouma et al. |
| 2008/0208227 A1 | 8/2008 | Kadykowski et al. |
| 2008/0225301 A1 | 9/2008 | Yamaguchi |
| 2008/0262346 A1 | 10/2008 | Assis et al. |
| 2008/0269572 A1 | 10/2008 | Kanz et al. |
| 2008/0291463 A1 | 11/2008 | Milner et al. |
| 2008/0297806 A1 | 12/2008 | Motaghiannezam et al. |
| 2009/0018393 A1 | 1/2009 | Dick et al. |
| 2009/0027689 A1 | 1/2009 | Yun et al. |
| 2009/0036782 A1 | 2/2009 | Vakoc et al. |
| 2009/0043191 A1 | 2/2009 | Castella et al. |
| 2009/0046295 A1 | 2/2009 | Kemp et al. |
| 2009/0046980 A1 | 2/2009 | Rohlen |
| 2009/0073454 A1 | 3/2009 | Ozawa |
| 2009/0073455 A1 | 3/2009 | Onimura |
| 2009/0093980 A1 | 4/2009 | Kemp et al. |
| 2009/0122320 A1 | 5/2009 | Petersen et al. |
| 2009/0131801 A1 | 5/2009 | Suter et al. |
| 2009/0135429 A1 | 5/2009 | Masuda |
| 2009/0143686 A1 | 6/2009 | Onimura et al. |
| 2009/0182246 A1 | 7/2009 | Kinoshita et al. |
| 2009/0192519 A1 | 7/2009 | Omori |
| 2009/0196477 A1 | 8/2009 | Cense et al. |
| 2009/0196554 A1 | 8/2009 | Irisawa |
| 2009/0251704 A1 | 10/2009 | Masuda |
| 2009/0261240 A1 | 10/2009 | Watanabe et al. |
| 2009/0262361 A1 | 10/2009 | Tanioka et al. |
| 2009/0283258 A1 | 11/2009 | Poitzsch et al. |
| 2009/0299195 A1 | 12/2009 | Muller et al. |
| 2009/0306520 A1 | 12/2009 | Schmitt et al. |
| 2010/0019189 A1 | 1/2010 | Kurita |
| 2010/0042084 A1 | 2/2010 | Nariyuki et al. |
| 2010/0073682 A1 | 3/2010 | Inoue |
| 2010/0076320 A1 | 3/2010 | Petersen et al. |
| 2010/0094127 A1 | 4/2010 | Xu |
| 2010/0110414 A1 | 5/2010 | Colice et al. |
| 2010/0130872 A1 | 5/2010 | Irisawa |
| 2010/0157309 A1 | 6/2010 | Tearney et al. |
| 2010/0158339 A1 | 6/2010 | Omori |
| 2010/0160134 A1 | 6/2010 | Scibona |
| 2010/0160780 A1 | 6/2010 | Swan et al. |
| 2010/0168587 A1 | 7/2010 | Feldman et al. |
| 2010/0220334 A1 | 9/2010 | Condit et al. |
| 2010/0241154 A1 | 9/2010 | Larson et al. |
| 2010/0249588 A1 | 9/2010 | Knight |
| 2010/0249601 A1 | 9/2010 | Courtney |
| 2010/0253949 A1 | 10/2010 | Adler et al. |
| 2010/0298908 A1 | 11/2010 | Vardiman |
| 2010/0305452 A1 | 12/2010 | Black et al. |
| 2010/0309477 A1 | 12/2010 | Yun et al. |
| 2011/0007315 A1 | 1/2011 | Petersen et al. |
| 2011/0009741 A1 | 1/2011 | Matthews et al. |
| 2011/0019182 A1 | 1/2011 | Hlavinka et al. |
| 2011/0058178 A1 | 3/2011 | Tearney et al. |
| 2011/0071404 A1 | 3/2011 | Schmitt et al. |
| 2011/0071405 A1 | 3/2011 | Judell et al. |
| 2011/0092823 A1 | 4/2011 | Tearney et al. |
| 2011/0101207 A1 | 5/2011 | Schmitt |
| 2011/0143905 A1 | 6/2011 | Kolenbrander et al. |
| 2011/0144504 A1 | 6/2011 | Tearney et al. |
| 2011/0149296 A1 | 6/2011 | Tearney et al. |
| 2011/0151980 A1 | 6/2011 | Petroff |
| 2011/0157686 A1 | 6/2011 | Huber et al. |
| 2011/0172511 A1 | 7/2011 | Petersen et al. |
| 2011/0178398 A1 | 7/2011 | Tearney et al. |
| 2011/0178413 A1 | 7/2011 | Schmitt et al. |
| 2011/0196217 A1 | 8/2011 | Myoujou et al. |
| 2011/0201924 A1 | 8/2011 | Tearney et al. |
| 2011/0216325 A1 | 9/2011 | Schmitt |
| 2011/0218403 A1 | 9/2011 | Tearney et al. |
| 2011/0224541 A1 | 9/2011 | Yun et al. |
| 2011/0228280 A1 | 9/2011 | Schmitt et al. |
| 2011/0237958 A1 | 9/2011 | Onimura |
| 2011/0245683 A1 | 10/2011 | Onimura |
| 2011/0245684 A1 | 10/2011 | Onimura |
| 2011/0261366 A1 | 10/2011 | Tearney et al. |
| 2011/0267340 A1 | 11/2011 | Kraus et al. |
| 2011/0270091 A1 | 11/2011 | Hossack et al. |
| 2011/0292400 A1 | 12/2011 | Fleming et al. |
| 2011/0299091 A1 | 12/2011 | Yun et al. |
| 2012/0002928 A1 | 1/2012 | Irisawa |
| 2012/0004506 A1 | 1/2012 | Tearney et al. |
| 2012/0007974 A1 | 1/2012 | Kaneko |
| 2012/0008146 A1 | 1/2012 | Tearney et al. |
| 2012/0013914 A1 | 1/2012 | Kemp et al. |
| 2012/0022360 A1 | 1/2012 | Kemp |
| 2012/0035454 A1 | 2/2012 | Tearney et al. |
| 2012/0053918 A1 | 3/2012 | Taylor |
| 2012/0057157 A1 | 3/2012 | Petersen et al. |
| 2012/0063570 A1 | 3/2012 | Furuichi et al. |
| 2012/0065517 A1 | 3/2012 | Goodnow et al. |
| 2012/0071736 A1 | 3/2012 | Luevano et al. |
| 2012/0123352 A1 | 5/2012 | Fruland et al. |
| 2012/0127476 A1 | 5/2012 | De Boer et al. |
| 2012/0135384 A1 | 5/2012 | Nakao |
| 2012/0170848 A1 | 7/2012 | Kemp et al. |
| 2012/0190974 A1 | 7/2012 | Suehara |
| 2012/0215091 A1 | 8/2012 | Suzuki et al. |
| 2012/0220836 A1 | 8/2012 | Alpert et al. |
| 2012/0226151 A1 | 9/2012 | Irisawa |
| 2012/0236883 A1 | 9/2012 | Adler |
| 2012/0238869 A1 | 9/2012 | Schmitt et al. |
| 2012/0243761 A1 | 9/2012 | Senzig et al. |
| 2012/0245459 A1 | 9/2012 | Senoo |
| 2012/0250028 A1 | 10/2012 | Schmitt et al. |
| 2012/0253114 A1 | 10/2012 | Kinoshita et al. |
| 2012/0253123 A1 | 10/2012 | Shimizu et al. |
| 2012/0253184 A1 | 10/2012 | Furuichi et al. |
| 2012/0253185 A1* | 10/2012 | Furuichi .......... A61B 8/4461 600/425 |
| 2012/0281237 A1 | 11/2012 | Tearney et al. |
| 2012/0310081 A1 | 12/2012 | Adler et al. |
| 2012/0330101 A1 | 12/2012 | Brennan et al. |
| 2013/0002843 A1 | 1/2013 | Horiike |
| 2013/0006104 A1 | 1/2013 | Mitsuhashi et al. |
| 2013/0006105 A1 | 1/2013 | Furuichi |
| 2013/0010303 A1 | 1/2013 | Petersen et al. |
| 2013/0012810 A1 | 1/2013 | Nakamoto et al. |
| 2013/0012811 A1 | 1/2013 | Schmitt et al. |
| 2013/0023760 A1 | 1/2013 | Liu et al. |
| 2013/0023761 A1 | 1/2013 | Petroff |
| 2013/0046190 A1 | 2/2013 | Davies et al. |

(56) References Cited

U.S. PATENT DOCUMENTS

| | | |
|---|---|---|
| 2013/0051728 A1 | 2/2013 | Petroff et al. |
| 2013/0072367 A1 | 3/2013 | Fletcher et al. |
| 2013/0072805 A1 | 3/2013 | Schmitt et al. |
| 2013/0079630 A1 | 3/2013 | Horiike |
| 2013/0079631 A1 | 3/2013 | Horiike et al. |
| 2013/0100455 A1 | 4/2013 | Tearney et al. |
| 2013/0107043 A1 | 5/2013 | Fletcher et al. |
| 2013/0116671 A1 | 5/2013 | Scheller et al. |
| 2013/0128274 A1 | 5/2013 | Yun et al. |
| 2013/0148106 A1 | 6/2013 | Tearney et al. |
| 2013/0176571 A1 | 7/2013 | Tearney et al. |
| 2013/0185023 A1 | 7/2013 | Vakoc et al. |
| 2013/0188850 A1 | 7/2013 | Tearney et al. |
| 2013/0215427 A1 | 8/2013 | Bouma et al. |
| 2013/0217964 A1 | 8/2013 | Kumoyama et al. |
| 2013/0222813 A1 | 8/2013 | Watanabe et al. |
| 2013/0246034 A1 | 9/2013 | Sharma et al. |
| 2013/0266259 A1 | 10/2013 | Bhagavatula et al. |
| 2013/0278936 A1 | 10/2013 | Inoue |
| 2013/0281844 A1 | 10/2013 | Karino et al. |
| 2013/0303907 A1 | 11/2013 | Corl |
| 2013/0310698 A1 | 11/2013 | Judell et al. |
| 2013/0314716 A1 | 11/2013 | Tearney et al. |
| 2013/0331689 A1 | 12/2013 | Le et al. |
| 2014/0005023 A1 | 1/2014 | Kolenbrander et al. |
| 2014/0018669 A1 | 1/2014 | Xu |
| 2014/0024930 A1 | 1/2014 | Furuichi et al. |
| 2014/0024931 A1 | 1/2014 | Winston et al. |
| 2014/0031677 A1 | 1/2014 | Iftimia et al. |
| 2014/0031679 A1 | 1/2014 | Tashiro et al. |
| 2014/0036941 A1 | 2/2014 | Adler |
| 2014/0063488 A1 | 3/2014 | Adler |
| 2014/0066706 A1 | 3/2014 | McWeeney et al. |
| 2014/0066756 A1 | 3/2014 | Sinclair et al. |
| 2014/0083970 A1 | 3/2014 | Kumar et al. |
| 2014/0088411 A1 | 3/2014 | Suehara et al. |
| 2014/0094697 A1 | 4/2014 | Petroff et al. |
| 2014/0100451 A1 | 4/2014 | Tolkowsky et al. |
| 2014/0114182 A1 | 4/2014 | Petersen et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0150782 A1 | 6/2014 | Vazales et al. |
| 2014/0177935 A1 | 6/2014 | Nair et al. |
| 2014/0180071 A1 | 6/2014 | Stigall et al. |
| 2014/0187929 A1 | 7/2014 | Schmitt et al. |
| 2014/0200867 A1 | 7/2014 | Lavi et al. |
| 2014/0206989 A1 | 7/2014 | Colice et al. |
| 2014/0207168 A1 | 7/2014 | Kawaura et al. |
| 2014/0218742 A1 | 8/2014 | Adler |
| 2014/0243876 A1 | 8/2014 | Suehara |
| 2014/0247454 A1 | 9/2014 | Bhagavatula et al. |
| 2014/0249407 A1 | 9/2014 | Adler et al. |
| 2014/0257087 A1 | 9/2014 | Elbasiony et al. |
| 2014/0267038 A1 | 9/2014 | Adler et al. |
| 2014/0268167 A1 | 9/2014 | Friedman et al. |
| 2014/0270436 A1 | 9/2014 | Dascal et al. |
| 2014/0270445 A1 | 9/2014 | Kemp |
| 2014/0276020 A1 | 9/2014 | Hutchins et al. |
| 2014/0276108 A1 | 9/2014 | Vertikov |
| 2014/0277072 A1 | 9/2014 | Suehara |
| 2014/0301620 A1 | 10/2014 | Tearney et al. |
| 2014/0323877 A1 | 10/2014 | Courtney et al. |
| 2014/0346693 A1 | 11/2014 | Hartkorn |
| 2014/0371598 A1 | 12/2014 | Okubo et al. |
| 2014/0376000 A1 | 12/2014 | Swanson et al. |
| 2014/0378845 A1 | 12/2014 | Nadkarni |
| 2014/0379269 A1 | 12/2014 | Schmitt |
| 2015/0005615 A1 | 1/2015 | Inoue et al. |
| 2015/0005626 A1 | 1/2015 | Kaneko |
| 2015/0005627 A1 | 1/2015 | Itoh et al. |
| 2015/0005628 A1 | 1/2015 | Itoh et al. |
| 2015/0025369 A1 | 1/2015 | Bhagavatula et al. |
| 2015/0029513 A1 | 1/2015 | Tearney et al. |
| 2015/0036146 A1 | 2/2015 | Staloff |
| 2015/0049339 A1 | 2/2015 | Tearney et al. |
| 2015/0051485 A1 | 2/2015 | Itoh et al. |
| 2015/0057958 A1 | 2/2015 | Watanabe et al. |
| 2015/0077755 A1 | 3/2015 | Yun et al. |
| 2015/0080700 A1 | 3/2015 | Fruland et al. |
| 2015/0099968 A1 | 4/2015 | Jamello |
| 2015/0099975 A1 | 4/2015 | Lam et al. |
| 2015/0119707 A1 | 4/2015 | Petroff |
| 2015/0133773 A1 | 5/2015 | Jaffer et al. |
| 2015/0133776 A1 | 5/2015 | Hoffman |
| 2015/0133789 A1 | 5/2015 | Ariura et al. |
| 2015/0153157 A1 | 6/2015 | Schmitt et al. |
| 2015/0164331 A1 | 6/2015 | Burgess et al. |
| 2015/0164423 A1 | 6/2015 | Webler |
| 2015/0182192 A1 | 7/2015 | Kaneko |
| 2015/0190054 A1 | 7/2015 | Kaneko |
| 2015/0192405 A1 | 7/2015 | Schmitt |
| 2015/0196285 A1 | 7/2015 | Mori |
| 2015/0216415 A1 | 8/2015 | Uribe-Patarroyo et al. |
| 2015/0219854 A1 | 8/2015 | Bhagavatula et al. |
| 2015/0230775 A1 | 8/2015 | Kobayashi |
| 2015/0238084 A1 | 8/2015 | Tearney et al. |
| 2015/0238121 A1 | 8/2015 | Tu et al. |
| 2015/0245768 A1 | 9/2015 | Hasegawa et al. |
| 2015/0257704 A1 | 9/2015 | Courtney |
| 2015/0257850 A1 | 9/2015 | Sakamoto |
| 2015/0265152 A1 | 9/2015 | Feldman et al. |
| 2015/0265162 A1 | 9/2015 | Lavi et al. |
| 2015/0268039 A1 | 9/2015 | Tu et al. |
| 2015/0282737 A1 | 10/2015 | Tolkowsky et al. |
| 2015/0297373 A1 | 10/2015 | Schmitt et al. |
| 2015/0306361 A1 | 10/2015 | Feig et al. |
| 2015/0320317 A1 | 11/2015 | Furuichi et al. |
| 2015/0366534 A1 | 12/2015 | Nair et al. |
| 2015/0370229 A1 | 12/2015 | Adler et al. |
| 2015/0371382 A1 | 12/2015 | Furuichi et al. |
| 2016/0000406 A1 | 1/2016 | Petroff |
| 2016/0007838 A1 | 1/2016 | Ariura et al. |
| 2016/0008090 A1 | 1/2016 | Yokoi et al. |
| 2016/0015337 A1 | 1/2016 | Inoue et al. |
| 2016/0018211 A1 | 1/2016 | Adler et al. |
| 2016/0022208 A1 | 1/2016 | Gopinath |
| 2016/0022248 A1 | 1/2016 | Mori et al. |
| 2016/0070066 A1 | 3/2016 | Schmitt et al. |
| 2016/0073885 A1 | 3/2016 | Adler |
| 2016/0089203 A1 | 3/2016 | Shimizu et al. |
| 2016/0089547 A1 | 3/2016 | Shimizu et al. |
| 2016/0092749 A1 | 3/2016 | Sakamoto |
| 2016/0093049 A1 | 3/2016 | Kobayashi |
| 2016/0095577 A1 | 4/2016 | Itoh et al. |
| 2016/0120408 A1 | 5/2016 | Bhagavatula et al. |
| 2016/0120492 A1 | 5/2016 | Honma et al. |
| 2016/0124134 A1 | 5/2016 | Zhu et al. |
| 2016/0157803 A1 | 6/2016 | Keller |
| 2016/0166815 A1 | 6/2016 | Suehara |
| 2016/0171701 A1 | 6/2016 | Zagrodsky et al. |
| 2016/0171711 A1 | 6/2016 | Gopinath et al. |
| 2016/0174925 A1 | 6/2016 | Dascal et al. |
| 2016/0199017 A1 | 7/2016 | Shimizu et al. |
| 2016/0202417 A1 | 7/2016 | Bhagavatula et al. |
| 2016/0206208 A1 | 7/2016 | Yamamoto et al. |
| 2016/0206267 A1 | 7/2016 | Shimizu et al. |
| 2016/0206290 A1 | 7/2016 | Itoh et al. |
| 2016/0228071 A1 | 8/2016 | Wang et al. |
| 2016/0270766 A1 | 9/2016 | Kobayashi |
| 2016/0301189 A1 | 10/2016 | Cable et al. |
| 2016/0313507 A1 | 10/2016 | Adler et al. |
| 2016/0320170 A1 | 11/2016 | Yun et al. |
| 2016/0320564 A1 | 11/2016 | Murashima et al. |
| 2016/0335763 A1 | 11/2016 | Ambwani et al. |
| 2016/0335766 A1 | 11/2016 | Ambwani et al. |
| 2016/0338753 A1 | 11/2016 | Ryba et al. |
| 2016/0341538 A1 | 11/2016 | Tumlinson et al. |
| 2016/0349417 A1 | 12/2016 | Tearney et al. |
| 2016/0370168 A1 | 12/2016 | Krol et al. |
| 2017/0014100 A1 | 1/2017 | Mori |
| 2017/0020392 A1 | 1/2017 | Xu |
| 2017/0024532 A1 | 1/2017 | Gopinath et al. |
| 2017/0024910 A1 | 1/2017 | Griffin et al. |

(56) References Cited

U.S. PATENT DOCUMENTS

| | | | |
|---|---|---|---|
| 2017/0103520 A1 | 4/2017 | Gopinath et al. |
| 2017/0135663 A1 | 5/2017 | Dascal et al. |
| 2017/0140243 A1 | 5/2017 | Ambwani |
| 2017/0140531 A1 | 5/2017 | Dascal et al. |
| 2017/0140532 A1 | 5/2017 | Dascal et al. |
| 2017/0140560 A1 | 5/2017 | Kraus et al. |
| 2017/0143296 A1 | 5/2017 | Peterson et al. |
| 2017/0148161 A1 | 5/2017 | Griffin |
| 2017/0153439 A1 | 6/2017 | Horiike |
| 2017/0188831 A1 | 7/2017 | Adler et al. |
| 2017/0238809 A1 | 8/2017 | Tearney et al. |
| 2017/0261378 A1 | 9/2017 | Friedman et al. |
| 2017/0301084 A1 | 10/2017 | Gopinath |
| 2017/0311806 A1 | 11/2017 | Comstock, II et al. |
| 2017/0325712 A1 | 11/2017 | Gopinath |
| 2017/0367581 A1 | 12/2017 | Tearney et al. |
| 2018/0003482 A1 | 1/2018 | Schmitt |
| 2018/0085095 A1 | 3/2018 | Hutchins et al. |
| 2018/0085170 A1 | 3/2018 | Gopinath |
| 2018/0125372 A1 | 5/2018 | Petroff et al. |
| 2018/0172424 A1 | 6/2018 | Comstock, II et al. |
| 2018/0177404 A1 | 6/2018 | Liu |
| 2018/0192957 A1 | 7/2018 | Schmitt et al. |
| 2018/0192983 A1 | 7/2018 | Dascal et al. |
| 2018/0225830 A1 | 8/2018 | Gopinath et al. |
| 2018/0226773 A1 | 8/2018 | Yun et al. |
| 2018/0275622 A1 | 9/2018 | Adler et al. |
| 2018/0293730 A1 | 10/2018 | Ambwani et al. |
| 2018/0306569 A1 | 10/2018 | Schmitt et al. |
| 2018/0344173 A1 | 12/2018 | Tu et al. |
| 2018/0344174 A9 | 12/2018 | Schmitt et al. |
| 2018/0353241 A1 | 12/2018 | Tu et al. |
| 2019/0035114 A1 | 1/2019 | Griffin et al. |
| 2019/0096063 A1 | 3/2019 | Ambwani |
| 2019/0099237 A1 | 4/2019 | Booker et al. |
| 2019/0220980 A1 | 7/2019 | Ambwani et al. |
| 2019/0307412 A1 | 10/2019 | Dascal et al. |
| 2019/0365480 A1 | 12/2019 | Gopinath et al. |
| 2019/0380594 A1 | 12/2019 | Schmitt et al. |
| 2020/0142575 A1 | 5/2020 | Gopinath et al. |
| 2020/0167923 A1 | 5/2020 | Gopinath |
| 2020/0355557 A1 | 11/2020 | Friedman et al. |
| 2020/0397405 A1 | 12/2020 | Hutchins et al. |
| 2021/0004955 A1 | 1/2021 | Ambwani et al. |

FOREIGN PATENT DOCUMENTS

| | | |
|---|---|---|
| CN | 1780584 | 5/2006 |
| CN | 203801215 | 9/2014 |
| CN | 203801216 | 9/2014 |
| CN | 203805643 | 9/2014 |
| CN | 203805646 | 9/2014 |
| CN | 105019592 | 11/2015 |
| CN | 204826364 | 12/2015 |
| CN | 105662387 | 6/2016 |
| CN | 106570313 | 4/2017 |
| CN | 106650029 | 5/2017 |
| CN | 106805989 | 6/2017 |
| CN | 106974622 | 7/2017 |
| CN | 107115108 | 9/2017 |
| CN | 107133959 | 9/2017 |
| CN | 107233106 | 10/2017 |
| CN | 107745346 | 3/2018 |
| CN | 107978371 | 5/2018 |
| CN | 108022650 | 5/2018 |
| CN | 108038848 | 5/2018 |
| CN | 207464715 | 6/2018 |
| DE | 69738291 | 9/2008 |
| DE | 112016005442 | 8/2018 |
| DE | 112016005603 | 10/2018 |
| EP | 0883793 | 12/1998 |
| EP | 1685366 | 8/2006 |
| EP | 2505129 | 10/2012 |
| EP | 2803973 | 11/2014 |
| JP | 2000503237 | 3/2000 |
| JP | 2005230552 | 9/2005 |
| JP | 2005533610 | 11/2005 |
| JP | 2006271869 | 10/2006 |
| JP | 2007268131 | 10/2007 |
| JP | 2008510586 | 4/2008 |
| JP | 2008523954 | 7/2008 |
| JP | 2009072291 | 4/2009 |
| JP | 4494203 | 6/2010 |
| JP | 2010167029 | 8/2010 |
| JP | 2010188138 | 9/2010 |
| JP | 2011078550 | 4/2011 |
| JP | 2012521852 | 9/2012 |
| JP | 5093787 | 12/2012 |
| JP | 2012254211 | 12/2012 |
| JP | 2013500142 | 1/2013 |
| JP | 2013506136 | 2/2013 |
| JP | 5269809 | 8/2013 |
| JP | 2014505496 | 3/2014 |
| JP | 5474190 | 4/2014 |
| JP | 2014180575 | 9/2014 |
| JP | 2014526283 | 10/2014 |
| JP | 5622796 | 11/2014 |
| JP | 5635149 | 12/2014 |
| JP | 5643315 | 12/2014 |
| JP | 2015013217 | 1/2015 |
| JP | 5689728 | 3/2015 |
| JP | 5721721 | 5/2015 |
| JP | 2015518393 | 7/2015 |
| JP | 5778579 | 9/2015 |
| JP | 2015164660 | 9/2015 |
| JP | 5814860 | 11/2015 |
| JP | 2015532717 | 11/2015 |
| JP | 5856605 | 2/2016 |
| JP | 2016508750 | 3/2016 |
| JP | 5987025 | 9/2016 |
| JP | 5997232 | 9/2016 |
| JP | 2018507400 | 3/2018 |
| JP | 2018527961 | 9/2018 |
| SB | 2512077 | 9/2014 |
| WO | 2004010856 | 2/2004 |
| WO | 2005047813 | 5/2005 |
| WO | 2006024015 | 3/2006 |
| WO | 2006068927 | 6/2006 |
| WO | 2008134449 | 11/2008 |
| WO | 2009009799 | 1/2009 |
| WO | 2009009802 | 1/2009 |
| WO | 2010095370 | 8/2010 |
| WO | 2010113374 | 10/2010 |
| WO | 2011038010 | 3/2011 |
| WO | 2012002302 | 1/2012 |
| WO | 2012064966 | 5/2012 |
| WO | 2013033415 | 3/2013 |
| WO | 2013126390 | 8/2013 |
| WO | 2014142789 | 9/2014 |
| WO | 2014142815 | 9/2014 |
| WO | 2014163601 | 10/2014 |
| WO | 2014175853 | 10/2014 |
| WO | 2015044978 | 4/2015 |
| WO | 2015044982 | 4/2015 |
| WO | 2015044983 | 4/2015 |
| WO | 2015044984 | 4/2015 |
| WO | 2015074018 | 5/2015 |
| WO | 2015136853 | 9/2015 |
| WO | 2015141136 | 9/2015 |
| WO | 2016168605 | 10/2016 |
| WO | 2016187218 | 11/2016 |
| WO | 2016187231 | 11/2016 |
| WO | 2016210132 | 12/2016 |
| WO | 2017011587 | 1/2017 |
| WO | 2017019626 | 2/2017 |
| WO | 2017019634 | 2/2017 |
| WO | 2015044987 | 3/2017 |
| WO | 2015045368 | 3/2017 |
| WO | 2017040484 | 3/2017 |
| WO | 2017097074 | 6/2017 |
| WO | 2017189942 | 11/2017 |

(56) References Cited

FOREIGN PATENT DOCUMENTS

| WO | 2017200381 | 11/2017 |
|---|---|---|
| WO | 2019108598 | 6/2019 |

OTHER PUBLICATIONS

Yun, S.H. et al. "High-speed optical frequency-domain imaging", Optics Express, vol. 11, No. 22 (Nov. 3, 2003), pp. 2953-2963.
Zheng, W. "Optic Lenses Manufactured on Fiber Ends", IEEE, 978-1-4673-7732-4/15, 2015, pp. 1-10.
International Search Report and Written Opinion dated Aug. 2, 2021 issued in corresponding International Application No. PCT/US2021/029836.
Extended European Search Report dated Apr. 21, 2022 issued in corresponding European Application No. 19862071.8.
Tran et al. "In vivo endoscopic optical coherence tomography by use of a rotational microelectromechanical system probe", Optics Letters, vol. 29 No. 11 (Jun. 1, 2004), p. 1236-1238.
Japanese Office Action dated Apr. 26, 2022 issued in corresponding Japanese Application No. 2021-068226, with English translation.
International Preliminary Report on Patentability dated Dec. 2, 2021 issued in related International Application No. PCT/US2020/033953.
"Imaging System Includes Imaging Probe and Delivery Devices" Specification, Drawings, and Prosecution History of U.S. Appl. No. 15/751,570, filed Feb. 9, 2018, now U.S Pat. No. 10,631,718, issued Apr. 28, 2020, by Christopher Petroff, et al.
Abozenadah, H., et al. Consumer Chemistry: How Organic Chemistry Impacts Our Lives. CC BY-NC-SA. Available at: https://wou.edu/chemistry/courses/online-chemistry-textbooks/ch105-consumer-chemistry/ (2017).
Athanasiou, L.S. et al. "Fully automated lumen segmentation of intracoronary optical coherence tomography images", Medical Imaging 2017, vol. 10133, pp. 101332I-1-101332I-7. Downloaded from the internet on Mar. 6, 2017: http://proceedings.spiedigitallibrary.org/.
Berger, J.D. et al. "Widely tunable external cavity diode laser based on a MEMS electrostatic rotary actuator", OSA/OFC 2001, pp. TuJ2-1-TuJ2-3.
BlazePhotonics. "NL-2.4-800 Highly nonlinear PCF" technical specification sheet.
Buus, J. et al. "Tunable Lasers in Optical Networks", Journal Of Lightwave Technology, vol. 24, No. 1 (Jan. 2006), pp. 5-11.
Chang-Hasnain, C.J. "Tunable VCSEL", IEEE Journal On Selected Topics In Quantum Electronics, vol. 6, No. 6 (Nov./Dec. 2000), pp. 978-987.
Chang-Hasnain, C.J., "Progress And Prospects Of Long-Wavelength VCSELs", IEEE Optical Communications (Feb. 2003), pp. S30-S34.
Chinn, S.R. et al. "Optical coherence tomography using a frequency-tunable optical source", Optics Letters, vol. 22, No. 5 (Mar. 1, 1997), pp. 340-342.
Chinese Notice of Allowance and Supplementary Search Report dated Jan. 13, 2021 issued in related Chinese Application No. 201680034490.4.
Chinese Office Action dated Aug. 28, 2019 issued in related Chinese Application No. 201680034490.4, with English translation.
Chinese Office Action dated Feb. 27, 2019 issued in related Chinese Application No. 201680034490.4, with English translation.
Chinese Office Action dated May 25, 2020 issued in related Chinese Application No. 201680034490.4, with English summary.
European Office Action dated Apr. 21, 2021 issued in corresponding European Application No. 16842796.1.
European Office Action dated Feb. 4, 2020 issued in related European Application No. 16780839.3.
Extended European Search Report dated Apr. 9, 2019 issued in related European Application No. 16842796.1.
Extended European Search Report dated Jan. 2, 2019 issued in related European Application No. 16780839.3.

International Preliminary Report on Patentability dated Jun. 11, 2020 issued in related International Application No. PCT/US2018/062766.
International Preliminary Report on Patentability dated Mar. 15, 2018 issued in related International Application No. PCT/US2016/049415.
International Preliminary Report on Patentability dated Oct. 17, 2017 issued in related International Application No. PCT/US2016/027764.
International Search Report & Written Opinion dated Feb. 11, 2019, issued in related International Application No. PCT/US2018/062766.
International Search Report and Written Opinion dated Jan. 31, 2020 issued in related International Application No. PCT/US2019/051447.
International Search Report and Written Opinion dated Jul. 30, 2020 issued in related International Applicatior No. PCT/US20/33953.
International Search Report and Written Opinion dated Sep. 14, 2020 issued in related International Application No. PCT/US20/30616.
International Search Report dated Jul. 14, 2016 issued in related International Application No. PCT/US2016/027764.
International Search Report dated Nov. 7, 2016, issued in related International Application No. PCT/US2016/049415.
Japanese Office Action dated Mar. 16, 2021 issued in related Japanese Application No. 2018-510969, with English language summary.
Japanese Office Action dated Mar. 31, 2020 issued in related Japanese Application No. 2018-505582, with English translation.
Japanese Office Action dated Nov. 17, 2020 issued in related Japanese Application No. 2018-505582, with English translation.
Japanese Office Action dated Sep. 15, 2020 issued in related Japanese Application No. 2018-510969, with English language summary.
Fermann, M.E. et al. "Ultrawide tunable Er solition fiber laser amplified in Yb-doped fiber", Optics Letters, vol. 24, No. 20 (Oct. 15, 1999), pp. 1428-1430.
Focabex, "Core Structure of Optical Cables" Article (online). Feb. 1, 2002 (retrieved Jan. 8, 2020). Retrieved from the Internet: URL: http://www.focabex.com/library-n/CORE-STRUCTURE-OF-OPTICAL-FIBER-CABLES.pdf.
Ghannam, M.T., et al. "Rheological Properties of Poly(dimethylsiloxane)". Industrial & Engineering Chemistry Research vol. 37, No. 4 (1998) pp. 1335-1340.
Golubovic, B. et al. "Optical frequency-domain reflectometry using rapid wavelength tuning of a Cr4+:forsterite laser", Optics Letters, vol. 22, No. 22 (Nov. 15, 1997), pp. 1704-1706.
Harris Jr., J.S. "Tunable Long-Wavelength Vertical-Cavity Lasers: The Engine of Next Generation Optical Networks?", IEEE Journal On Selected Topics In Quantum Electronics, vol. 6, No. 6 (Nov./Dec. 2000), pp. 1145-1160.
Introduction to silicone fluids (https://www.clearcoproducts.com/introduction-to-silicone-fluids.html), retrieved Sep. 24, 2020.
Jiefeng Xi, et al. "Diffractive catheter for ultrahigh-resolution spectral-domain volumetric OCT imaging", Optics Letters, vol. 39, No. 7, Optical Society of America, Mar. 26, 2014, pp. 2016-2019.
Kakuta, T. et al. "Behavior of optical fibers under heavy irradiation", Fusion Engineering And Design, vol. 41 (1998), pp. 201-205.
Madigan, Jeremy. "Vascular access: guide catheter selection, usage, and compatibility." Interventional Neuroradiology, Springer, London (2014), pp. 27-38.
Meuwissen, M. et al. "Role of Variability in Microvascular Resistance onFractional Flow Reserve and Coronary Blood Flow Velocity Reserve in Intermediate Coronary Lesions", Circulation, 103 (2001), pp. 184-187 [online—retrieved on Mar. 7, 2018]. Retrieved from the Internet URL: http://circ.ahajournals.org/content/103/2/184.
NKT Photonics. "ESM-12 Single0mode 12 urn core fiber" technical specification sheet.
NKT Photonics. "HC-1550-02 Hollow Core Photonic Bandgap Fiber" technical specification sheet.
NKT Photonics. "HC-800-02 Hollow Core Photonic Bandgap Fiber" technical specification sheet.

(56) References Cited

OTHER PUBLICATIONS

Ofili, E.O. et al. "Differential characterization of blood flow, velocity, and vascular resistance between proximal and distal normal epicardial human coronary arteries: Analysis by intracoronary Doppler spectral flow velocity", American Heart Journal (Jul. 1995), pp. 37-46.

Reed, W.A. et al. "Gradient-index fiber-optic microprobes for minimally invasive in vivo low-coherence interferometry", Optics Letters, vol. 27, No. 20 (Oct. 15, 2002), pp. 1794-1796.

Tearney, G.J. et al. "High-speed phase- and group-delay scanning with a grating-based phase control delay line", Optics Letters, vol. 22, No. 23 (Dec. 1, 1997), pp. 1811-1813.

Thorlabs, "Single Wavelength Graded-Index (GRIN) Lenses" Product Catalogue (online). Apr. 9, 2016 (retrieved Jan. 8, 2020). Retrieved from the Internet: URL: https://www.thorlabs.com/NewGroupPage9.cfm?ObjectGroup_ID=1209.

Von der Weid, J.P. et al. "On the Characterization of Optical Fiber Network Components with Optical Frequency Domain Reflectometry", Journal of Lightwave Technology, vol. 15, No. 7 (Jul. 1997), pp. 1131-1141.

Xi et al. "Diffractive catheter for ultrahigh-resolution spectral-domain volumetric OCT imaging", Optics Letters, vol. 39, No. 7 (Mar. 26, 2014), pp. 2016-2019.

Youngquist, R.C. et al."Optical coherence-domain reflectometry: a new optical evaluation technique", Optics Letters, vol. 12, No. 3 (Mar. 1987), pp. 158-160.

Japanese Office Action dated Aug. 2, 2022 issued in corresponding Japanese Application No. 2021-117103, with English translation.

Extended European Search Report dated Nov. 26, 2021 issued in corresponding European Application No. 18883166.3.

International Preliminary Report on Patentability dated Nov. 11, 2021 issued in corresponding International Application No. PCT/US20/30616.

Japanese Office Action dated Nov. 15, 2022 issued in related Japanese Application No. 2021-068226, with English translation.

International Preliminary Report on Patentability electronically transmitted to Applicant dated Nov. 10, 2022, issued in related International Application No. PCT/US2021/029836.

\* cited by examiner

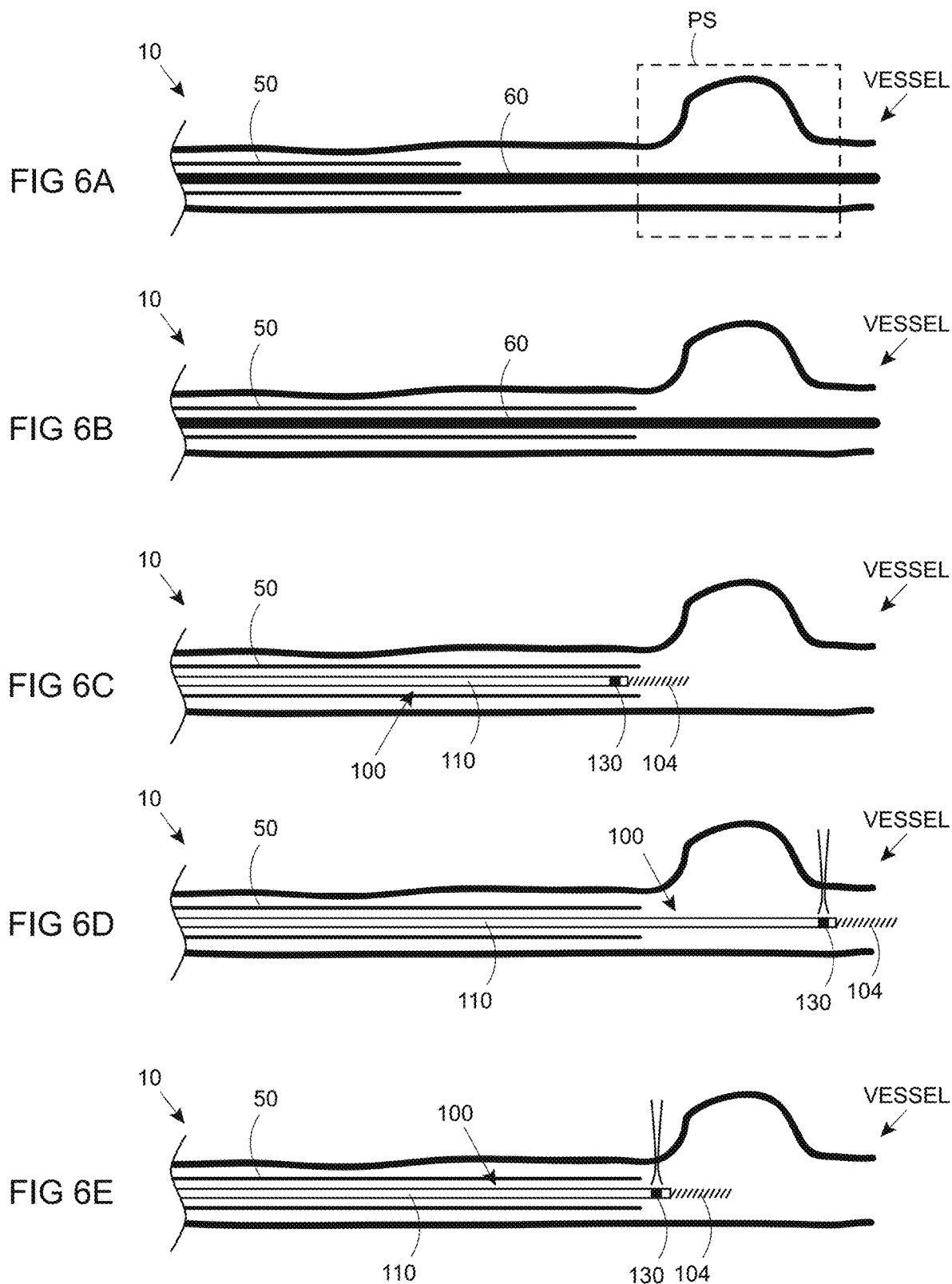

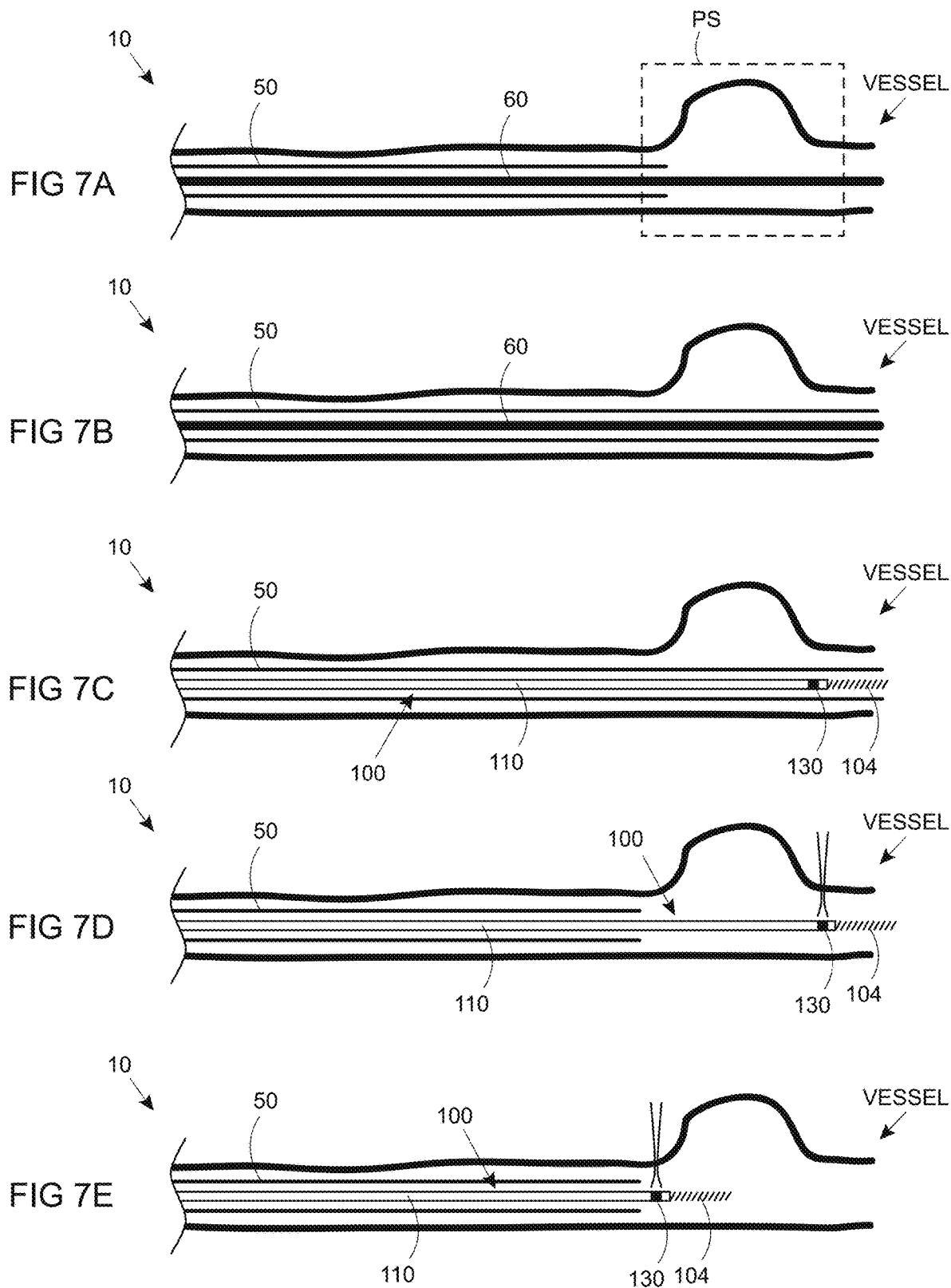

IMAGING SYSTEM INCLUDES IMAGING PROBE AND DELIVERY DEVICES

RELATED APPLICATIONS

This application is a continuation application of U.S. patent application Ser. No. 16/820,991, filed on Mar. 17, 2020, which is a continuation application of U.S. patent application Ser. No. 15/751,570, filed on Feb. 9, 2018, now U.S. Pat. No. 10,631,718, issued on Apr. 28, 2020, which is a U.S. National Stage entry of International Patent Application No. PCT/US2016/049415, filed Aug. 30, 2016, which claims priority to U.S. Provisional Application Ser. No. 62/212,173, titled "Imaging System includes Imaging Probe and Delivery Devices", filed Aug. 31, 2015; and U.S. Provisional Application Ser. No. 62/368,387, titled "Imaging System Includes Imaging Probe and Delivery Devices", filed Jul. 29, 2016; the content of each of which is incorporated herein by reference in its entirety.

This application is related to U.S. Provisional Application Ser. No. 62/212,173, titled "Imaging System including Imaging Probe and Delivery Devices", filed Aug. 31, 2015; and International PCT Patent Application Serial Number PCT/US2016/027764, titled "Micro-Optic Probes for Neurology" filed Apr. 15, 2016; the content of each of which is incorporated herein by reference in its entirety for all purposes.

FIELD

Inventive concepts relate generally to imaging systems, and in particular, neural and cardiac optical imaging systems including imaging probes and delivery devices.

BACKGROUND

Imaging probes have been commercialized for imaging various internal locations of a patient, such as an intravascular probe for imaging a patient's heart. Current imaging probes are limited in their ability to reach certain anatomical locations due to their size and rigidity. Current imaging probes are inserted over a guidewire, which can compromise their placement and limit use of one or more delivery catheters through which the imaging probe is inserted. There is a need for imaging systems that include probes with reduced diameter, high flexibility and the ability to be advanced to a patient site to be imaged without a guidewire, as well as systems with one or more delivery devices compatible with these improved imaging probes.

SUMMARY

According to one aspect of the present inventive concepts, an imaging system comprises an imaging probe comprising an elongate shaft comprising a proximal end, a distal portion, and a lumen extending between the proximal end and the distal portion. The imaging probe further comprises a rotatable optical core positioned within the lumen of the elongate shaft and comprising a proximal end and a distal end, the rotatable optical core configured to optically and mechanically connect with an interface unit, and an optical assembly positioned in the elongate shaft distal portion and proximate the rotatable optical core distal end, the optical assembly configured to direct light to tissue and collect reflected light from the tissue. The imaging probe is constructed and arranged to collect image data from a patient site. The system further comprises at least one delivery device (e.g. a first delivery catheter) constructed and arranged to slidingly engage (e.g. slidingly receive) the imaging probe. The imaging system can further comprise a rotating assembly constructed and arranged to rotate the optical assembly. The imaging system can further comprise a retraction assembly constructed and arranged to retract the optical assembly and the elongate shaft (e.g. retract the elongate shaft to cause retraction of the elongate shaft and the optical assembly in unison).

In some embodiments, the imaging probe is constructed and arranged such that relative motion between the elongate shaft and the optical assembly is prevented. In these embodiments, the elongate shaft can comprise a transparent segment (e.g. a transparent segment positioned about the optical assembly) that is less than or equal to 15 mm in length, less than or equal to 6 mm in length, or less than or equal to 4 mm in length. The imaging probe can further comprise a connector rotatably attached to the rotatable optical core and fixedly attached to the elongate shaft, and the connector can be constructed and arranged to cause the prevention of the relative motion between the elongate shaft and the rotatable optical core.

In some embodiments, the imaging system comprises an OCT imaging system.

In some embodiments, the imaging probe elongate shaft distal portion comprises an outer diameter (OD) less than or equal to 0.025".

In some embodiments, the imaging probe elongate shaft distal portion comprises an OD less than or equal to 0.022".

In some embodiments, the imaging probe elongate shaft distal portion comprises an OD less than or equal to 0.018".

In some embodiments, the imaging probe elongate shaft distal portion comprises an OD less than or equal to 0.016".

In some embodiments, the imaging probe elongate shaft distal portion comprises an OD less than or equal to 0.015".

In some embodiments, the imaging probe elongate shaft distal portion comprises an OD less than or equal to 0.014".

In some embodiments, the imaging probe elongate shaft comprises a material selected from the group consisting of: PEEK, polyimide, nylon; FEP; PTFE; Pebax; and combinations thereof.

In some embodiments, the imaging probe elongate shaft distal portion comprises a braided portion.

In some embodiments, the at least one delivery device comprises at least one delivery catheter constructed and arranged to slidingly receive the imaging probe. The at least one delivery catheter can comprise a catheter from the group consisting of: a 7 Fr to 9 Fr Introducer; a 5 Fr to 7 Fr guide catheter; an intermediate catheter with an inner diameter (ID) between 0.053" to 0.070"; a microcatheter with an ID between 0.0165" and 0.027"; and combinations thereof. The at least one delivery device can further comprise at least a first guidewire. The at least one delivery device can further comprise at least a second guidewire with an OD less than the OD of the first guidewire. The at least one delivery catheter can comprise an ID of approximately 0.021", or an ID of at least 0.0165". The at least one delivery catheter can comprise an ID of approximately 0.027". The at least one delivery device can be constructed and arranged to receive optically transparent fluid within the at least one delivery device. The at least one delivery catheter can comprise a proximal portion and a Touhy valve positioned on the proximal portion. The at least one delivery catheter can comprise a catheter with an OD of approximately 0.0240" and an ID of approximately 0.0165". The at least one delivery catheter can comprise a distal end and a marker proximate the distal end. The marker can comprise a marker selected from the group consisting of: radiopaque marker; ultrasonically visible marker; magnetic marker; and combinations thereof. The at least one delivery catheter can comprise a shaft with a distal portion including a transparent segment. The transparent segment can comprise an OD of approximately 0.022" and an ID of approximately 0.0165". The transparent segment can comprise a length of up to 50 cm. The transparent segment can comprise a length of up to 10 cm. The transparent segment can comprise a length of up to 5 cm. The transparent segment can be configured to be advanced within an implanted device, and the optical assembly can be configured to be retracted within the transparent segment. The implanted device can comprise a device selected from the group consisting of: flow diverter; Pipeline flow diverter; coil; stent; covered stent; aneurysm treatment implant; and combinations thereof.

In some embodiments, the at least one delivery device is constructed and arranged to slidingly receive the elongate shaft, and the at least one delivery device comprises a transparent distal portion.

In some embodiments, the at least one delivery device comprises at least one guidewire. The at least one guidewire can be constructed and arranged to slidingly engage the imaging probe. The imaging probe can comprise a rapid exchange lumen in the distal portion of its elongate shaft. The at least one delivery device can further comprise at least one delivery catheter constructed and arranged to slidingly receive the at least one guidewire. The at least one guidewire can comprise a guidewire selected from the group consisting of: a guidewire with an OD between 0.035" and 0.038"; a guidewire with an OD between 0.010" and 0.018"; an access length guidewire such as a guidewire with a length of approximately 200 cm; an exchange length guidewire such as a guidewire with a length of approximately 300 cm; a guidewire with a length between 175 cm and 190 cm; a guidewire with a length between 200 cm and 300 cm and/or an OD between 0.014" and 0.016"; a hydrophilic guidewire; a Stryker Synchro™ guidewire; a Terumo guidewire such as the Terumo Glidewire™ guidewire; a Terumo Traxcess™ guidewire; an X-Celerator™ guidewire; an X-Pedion™ guidewire; an Agility™ guidewire; a Bentson™ guidewire; a Coon™ guidewire; an Amplatz™ guidewire; and combinations thereof.

In some embodiments, the imaging probe comprises a diameter (e.g. an OD) between 0.014" and 0.016" and the at least one delivery device comprises a guidewire constructed and arranged to access the patient site, and the patient site comprises a neural site or a cardiac site. The at least one delivery device can further comprise a first delivery catheter comprising an ID between 0.021" and 0.027" and constructed and arranged to advance over the guidewire to the patient site. The imaging probe can be constructed and arranged to be advanced within the first delivery catheter after the guidewire is removed from the first delivery catheter, the first delivery catheter can be configured to be retracted after the imaging probe is advanced into the first delivery catheter, and the imaging probe can be configured to be retracted after retraction of the first delivery catheter, the retraction of the imaging probe can be performed while the image data is collected. The system can further comprise flushing medium constructed and arranged to be delivered through the first delivery device as the imaging probe is retracted to collect the image data (e.g. flushing medium which passes between the imaging probe and the first delivery device). The imaging probe can be constructed and arranged to be removed from the first delivery catheter after the image data is collected, and the guidewire can be constructed and arranged to be inserted into the first delivery catheter after the probe is removed. The neural or cardiac site can comprise at least one of aneurysm, stenosis, thrombus or an implant.

In some embodiments, the at least one delivery device comprises a first guidewire configured to access a patient site (e.g. a neural site or a cardiac site), a first delivery catheter including an ID between 0.021" and 0.027" and a distal portion comprising a transparent segment, and configured to advance over the guidewire to the patient site, and the system is configured to collect the image data by retracting the optical assembly while the optical assembly is positioned within the transparent segment of the first delivery catheter. The imaging probe elongate shaft distal portion can comprise an OD between 0.014" and 0.016".

In some embodiments, the patient site comprises a neural site or a cardiac site, and the patient site can comprise a site selected from the group consisting of: an aneurysm; stenosis; thrombus; implant; and combinations thereof. The at least one delivery device can comprise a delivery catheter.

In some embodiments, the at least one delivery device comprises: a first guidewire configured to access the patient site, such as when the patient site comprises a neural site or a cardiac site; a first delivery catheter comprising an ID of approximately 0.027", the first delivery catheter configured to be advanced over the first guidewire; and a second delivery catheter comprising an OD of approximately 0.025" and a distal portion including a transparent segment. The second delivery catheter can be configured to be advanced over the first guidewire through the first delivery catheter, and to slidingly receive the imaging probe. The imaging probe can comprise a diameter (e.g. an OD) of approximately 0.016".

In some embodiments, the at least one delivery device comprises a first delivery catheter comprising a 5 Fr to 7 Fr guide catheter and a proximal portion with a Touhy valve and a second delivery catheter configured to be slidingly received by the first delivery catheter and further configured to slidingly receive the imaging probe. The system can further comprise a third delivery catheter configured to be slidingly received by the second delivery catheter and further configured to slidingly receive the imaging probe. The imaging probe can comprise a diameter (e.g. an OD) between 0.014" and 0.016".

In some embodiments, the at least one delivery device comprises at least one delivery catheter, and the probe and the at least one delivery catheter are constructed and arranged such that the optical assembly remains beyond the distal end of the at least one delivery catheter during the collection of the image data. The system can be configured to retract the optical assembly during the image data collection. The imaging probe elongate shaft distal portion can comprise an OD of approximately 0.014". The at least one delivery catheter can comprise an OD of approximately 0.022". The imaging probe elongate shaft distal portion can comprise an OD of between 0.014" and 0.016" and the at least one delivery catheter can comprise an OD of approximately 0.032". The imaging probe can comprise a length up to 200 cm and the at least one delivery catheter can comprise a length at least 2 cm shorter than the length of the imaging probe. The imaging probe can further comprise a spring tip on the distal end of the imaging probe elongate shaft. The spring tip can comprise a radiopaque portion. The spring tip can comprise a length between 2 cm and 3 cm. The at least one delivery device can further comprise a guide catheter with a proximal end comprising a Touhy valve. The imaging probe can be configured to be removed from the at least one delivery catheter. The system can further comprise a treatment device configured to be inserted through the at least one delivery catheter.

In some embodiments, the at least one delivery device comprises at least one delivery catheter comprising a distal portion with a transparent segment, and the probe and the at least one delivery catheter are constructed and arranged such that the optical assembly remains within the transparent segment of the at least one delivery catheter during the collection of the image data. The imaging probe elongate shaft distal portion can comprise an OD of approximately 0.014". The at least one delivery catheter can comprise an ID of approximately 0.0165". The at least one delivery catheter can comprise an OD of approximately 0.022". The at least one delivery catheter distal portion can comprise a marker. The at least one delivery catheter can comprise a spring tip. The at least one delivery catheter can comprise a rapid exchange tip.

In some embodiments, the at least one delivery device comprises a first delivery catheter comprising an introducer such as a vascular introducer, and a second delivery catheter comprising a guide catheter such as a 6 Fr guide catheter including a distal end for positioning proximate the aortic arch and a third delivery catheter comprising an ID between 0.021" and 0.027" and a distal end constructed and arranged to be advanced to a location as distal as the middle cerebral artery (MCA). The third delivery catheter distal end can be constructed and arranged to be advanced to a location proximate a location selected from the group consisting of: internal ceratoid artery; intracranial internal carotid artery (from the cervical ICA); petrous ICA; proximal cavernous ICA; distal cavernous/clinoidal ICA; supraclinoid ICA; the M1 segment V3-4 junction of the vertebral artery; distal V4; proximal basilar; proximal-mid basilar; mid-basilar; and combinations thereof.

In some embodiments, the at least one delivery catheter comprises a component selected from the group consisting of: a first delivery catheter comprising an introducer with an ID between 7 Fr and 9 Fr; a second delivery catheter comprising a guide catheter configured to be slidingly received by the first delivery catheter and comprising an ID between 5 Fr and 7 Fr, a Touhy valve and/or a length of approximately 90 cm; a third delivery catheter comprising an intermediate catheter configured to be slidingly received by the second delivery catheter and comprising an OD less than 7 Fr and/or a length of approximately 115 cm; a fourth delivery catheter comprising a microcatheter configured to be slidingly received by the third delivery catheter and comprising an ID less than 0.027"; a first guidewire configured to be slidingly received by the first delivery catheter, the second delivery catheter, the third delivery catheter and/or the fourth delivery catheter and comprising a length of between 175 cm and 190 cm; a second guidewire configured to be slidingly received by the first delivery catheter, the second delivery catheter, the third delivery catheter and/or the fourth delivery catheter and comprising a length of between 175 cm and 190 cm; and combinations thereof. The system can further comprise a power injector. The system can further comprise an implant comprising a flow diverter. The flow diverter can comprise at least one of a Pipeline™ flow diverter or a Pipeline Flex™ flow diverter.

In some embodiments, the at least one delivery catheter comprises a component selected from the group consisting of: a first delivery catheter comprising an introducer with an ID between 7 Fr and 9 Fr; a second delivery catheter comprising a guide catheter configured to be slidingly received by the first delivery catheter and comprising an ID between 5 Fr and 7 Fr, a Touhy valve and/or a length of approximately 90 cm; a third delivery catheter comprising an intermediate catheter configured to be slidingly received by the second delivery catheter and comprising an OD less than 7 Fr and/or a length of approximately 115 cm; a fourth delivery catheter comprising a microcatheter configured to be slidingly received by the third delivery catheter and comprising a Surpass™ delivery catheter, an OD less than 3.3 Fr or less than 3.7 Fr and/or a length of approximately 135 cm; a first guidewire configured to be slidingly received by the first delivery catheter, the second delivery catheter, the third delivery catheter and/or the fourth delivery catheter and comprising an exchange length guidewire; and combinations thereof. The system can further comprise a power injector. The system can further comprise an implant comprising a flow diverter. The flow diverter can comprise at least one of a Surpass™ flow diverter or a Surpass Future™ flow diverter.

In some embodiments, the at least one delivery catheter comprises a component selected from the group consisting of: a first delivery catheter comprising an introducer with an ID between 7 Fr and 9 Fr; a second delivery catheter comprising a guide catheter configured to be slidingly received by the first delivery catheter and comprising an ID between 5 Fr and 7 Fr, an ID of approximately 0.088", a length of between 80 cm and 90 cm and/or a distal end configured to be positioned proximate the aortic arch; a third delivery catheter comprising a reperfusion catheter configured to be slidingly received by the second delivery catheter and comprising an OD between 3.8 Fr and 5.4 Fr and/or a length between 132 cm and 153 cm; a fourth delivery catheter comprising a microcatheter configured to be slidingly received by the third delivery catheter and comprising an OD of approximately 2.6 Fr and/or a length of approximately 160 cm; and combinations thereof. The system can further comprise a power injector. The system can further comprise a treatment device comprising a stent retriever or other thrombus removal device. The treatment device can comprise a Penumbra ACE™ stent retriever device.

In some embodiments, the at least one delivery catheter comprises a component selected from the group consisting of: a first delivery catheter comprising an introducer with an ID between 7 Fr and 9 Fr; a second delivery catheter comprising a guide catheter configured to be slidingly received by the first delivery catheter and comprising an ID between 5 Fr and 7 Fr, a Touhy valve and/or a length of approximately 90 cm; a third delivery catheter comprising an intermediate catheter configured to be slidingly received by the second delivery catheter and comprising an OD less than 7 Fr and/or a length of approximately 115 cm; a fourth delivery catheter comprising a microcatheter configured to be slidingly received by the third delivery catheter and comprising an ID of approximately 0.0165" and/or a length of approximately 150 cm; a first guidewire configured to be slidingly received by the first delivery catheter, the second delivery catheter, the third delivery catheter and/or the fourth delivery catheter and comprising an OD of approximately 0.014" and/or a length between 175 cm and 190 cm; and combinations thereof. The system can further comprise a power injector. The system can further comprise a treatment device comprising a coil deployment catheter. The system can further comprise at least one coil.

In some embodiments, the system further comprises a treatment device. The collected image data can include data of the treatment device. The treatment device can comprise a device selected from the group consisting of: a balloon catheter constructed and arranged to dilate a stenosis or other narrowing of a blood vessel; a drug eluting balloon; an aspiration catheter; a sonolysis device; an atherectomy device; a thrombus removal device such as a stent retriever device; a Trevo™ stentriever; a Solitaire™ stentriever; a Revive™ stentriever; an Eric™ stentriever; a Lazarus™ stentriever; a stent delivery catheter; a microbraid implant; an embolization system; a WEB™ embolization system; a Luna™ embolization system; a Medina™ embolization system; and combinations thereof. The treatment device can comprise a thrombus removal device. The thrombus removal device can comprise a stent retriever device.

In some embodiments, the system further comprises an implant. The collected image data can include data of the treatment device. The implant can comprise a device selected from the group consisting of: a flow diverter; a Pipeline™ flow diverter; a Surpass™ flow diverter; an embolization coil; a stent; a Wingspan™ stent; a covered stent; an aneurysm treatment implant; and combinations thereof. The implant can comprise an aneurysm treatment implant. The implant can comprise a flow diverter. The implant can comprise a covered stent. The implant can comprise a stent. The implant can comprise a coil.

In some embodiments, the system further comprises a console including an assembly selected from the group consisting of: rotating assembly; a retraction assembly; an imaging assembly; a light source; an algorithm; a display; and combinations of these.

In some embodiments, the system further comprises an imaging assembly configured to provide light to optical assembly and to collect light from optical assembly. The imaging assembly can comprise a light source. The light source can comprise at least two light sources. The light source can be configured to deliver light with a center wavelength between 800 nm and 1700 nm. The light source can be configured to deliver light with a center wavelength of approximately 1300 nm or approximately 1380 nm. The light source can be configured to deliver light with bandwidths between 5% and 15% of a center wavelength. The light source can be configured to deliver light in the 1.3 μm band. The light source can be configured to deliver light at a power level of approximately 20 mW.

In some embodiments, the system further comprises a rotating assembly constructed and arranged to rotate the optical assembly. The rotating assembly can be constructed and arranged to rotate the optical assembly at a rate between 40 rps and 1000 rps. The rotating assembly can be constructed and arranged to rotate the optical assembly at a rate between 50 rps and 2500 rps, or between 150 rps and 2500 rps. The rotating assembly can be constructed and arranged to rotate the optical assembly at a rate of approximately 250 rps. The system can be configured to operate in an imaging mode and a preview mode, and the rotating assembly can be constructed and arranged to rotate the optical assembly at a first rate during the imaging mode, and at a second rate during the preview mode, and the second rate can be slower than the first rate. The rotating assembly can be constructed and arranged to rotate the optical assembly at a rate between 40 rps and 1000 rps during the imaging mode and at a rate of between 30 rps and 140 rps during the preview mode. The system can be configured to linearly position the optical assembly while in the preview mode.

In some embodiments, the system further comprises a retraction assembly constructed and arranged to retract at least the optical assembly. The retraction assembly can be further constructed and arranged to retract the imaging probe elongate shaft (e.g. retract the elongate shaft and optical assembly in unison). The retraction assembly can be constructed and arranged to retract the optical assembly at a rate between 5 mm/sec and 60 mm/sec during the collection of the image data. The retraction assembly can be constructed and arranged to retract the optical assembly at a rate of approximately 40 mm/sec during the collection of the image data. The retraction assembly can be constructed and arranged to retract the optical assembly a distance between 10 mm and 150 mm during the collection of the image data. The retraction assembly can be constructed and arranged to retract the optical assembly a distance of approximately 40 mm during the collection of image data. The retraction assembly can be constructed and arranged to retract the optical assembly for a time period between 2 seconds and 15 seconds during the collection of image data.

In some embodiments, the system further comprises an algorithm configured to adjust an operational parameter. The operational parameter can comprise a parameter selected from the group consisting of: a rotational parameter such as rotational velocity of the rotatable optical core and/or the optical assembly; a retraction parameter of the imaging probe elongate shaft and/or the optical assembly such as retraction velocity, distance, start position, end position and/or retraction initiation timing; a position parameter such as position of the optical assembly; a line spacing parameter such as lines per frame; an image display parameter such as a scaling of display size to vessel diameter; an imaging probe configuration parameter; an injectate parameter such as a saline to contrast ratio configured to determine an appropriate index of refraction; a light source parameter such as power delivered and/or frequency of light delivered; and combinations thereof. The algorithm can be configured to adjust an operational parameter selected from the group consisting of: a retraction parameter; a parameter triggering the initiation of a pullback of the imaging probe elongate shaft; a pullback parameter adjusted based on lumen clearing; a pullback parameter adjusted based on a signal from an injector; a pullback parameter adjusted based on image data collected; an imaging probe parameter such as arm path length; and combinations thereof.

In some embodiments, the system further comprises a display configured to display one or more images based on the collected image data. The display can be configured to display video based on the collected image data. The display can be configured to display images at a frame rate of less than or equal to 250 frames/second.

In some embodiments, the system (e.g. the imaging probe or other system component) further comprises a functional element. The functional element can comprise at least two functional elements. The functional element can comprise an element selected from the group consisting of: sensor; transducer; and combinations thereof. The functional element can comprise a sensor configured to produce a signal. The functional element can comprise a sensor selected from the group consisting of: a physiologic sensor; a pressure sensor; a strain gauge; a position sensor; a GPS sensor; an accelerometer; a temperature sensor; a magnetic sensor; a chemical sensor; a biochemical sensor; a protein sensor; a flow sensor such as an ultrasonic flow sensor; a gas detecting sensor such as an ultrasonic bubble detector; a sound sensor such as an ultrasound sensor; and combinations thereof. The sensor can comprise a physiologic sensor selected from the group consisting of: a pressure sensor such as a blood pressure sensor; a blood gas sensor; a flow sensor such as a blood flow sensor; a temperature sensor such as a blood or other tissue temperature sensor; and combinations thereof. The sensor can comprise a position sensor configured to produce a signal related to a vessel path geometry (e.g. a 2D or 3D vessel path geometry). The sensor can comprise a magnetic sensor. The sensor can comprise a flow sensor. The system can further comprise an algorithm configured to process the signal produced by the sensor. The functional element can comprise a transducer. The functional element can comprise a transducer selected from the group consisting of: a heating element such as a heating element configured to deliver sufficient heat to ablate tissue; a cooling element such as a cooling element configured to deliver cryogenic energy to ablate tissue; a sound transducer such as an ultrasound transducer; a vibrational transducer; and combinations thereof. The functional element can comprise a pressure relief valve. The functional element can comprise at least one sidehole. The functional element can comprise a visualizable marker. The functional element can comprise a deployable functional element. The functional element can comprise an implantable functional element. The imaging probe can comprise the functional element. The functional assembly can be proximate the optical assembly. The system can further comprise a console, and the console can comprise the functional element. The system can further comprise an injector, and the injector can comprise the functional element.

In some embodiments, the system further comprises an injector constructed and arranged to deliver injectate to the at least one delivery device. The injector can be configured to deliver fluid to perform a flushing procedure. The flushing procedure can be performed based on a parameter selected from the group consisting of: a pre-determined volume of injectate to be delivered; a pre-determined time during which injectate is delivered; an amount of time of delivery including a time extending from a time prior to retraction of the imaging probe elongate shaft until the collecting of the image data has been completed; and combinations thereof. The system can further comprise injectate comprising one or more fluids to be delivered by the injector. The injectate can comprise fluid selected from the group consisting of: optically transparent material; saline; visualizable material; contrast; Dextran; an ultrasonically reflective material; a magnetic material; and combinations thereof. The injectate can comprise contrast and saline. The injectate can comprise at least 20% contrast. The injector can comprise a first reservoir and a second reservoir, and the injectate can comprise a first fluid delivered from the first reservoir and a second fluid delivered from the second reservoir. The injector can be configured to deliver the first and second fluids at different rates.

According to another aspect of the present inventive concepts, a method of creating an image comprises: (a) selecting an imaging probe according to any claim herein; (b) selecting at least one delivery device; (c) advancing a first delivery device within a blood vessel of the patient, the first delivery device comprising a first delivery catheter comprising a distal end; (d) advancing the imaging probe within the first delivery catheter such that the optical assembly of the imaging probe is proximate a patient site; (e) retracting the elongate shaft of the imaging probe and collecting image data of the patient site during the retraction; and (f) creating one or more images based on the collected image data. The optical assembly can be positioned within the first delivery catheter during the collection of the image data. The first delivery catheter can comprise a transparent segment and the optical assembly can be within the transparent segment during the collecting of the image data. The optical assembly can be positioned distal to the distal end of the first delivery catheter during the collection of the image data.

In some embodiments, the patient site comprises a blood vessel selected from the group consisting of: artery of patient's neck; vein of patient's neck; artery of patient's head; vein of patient's head; artery of patient's brain; vein of patient's brain; and combinations thereof.

In some embodiments, the patient site comprises one or more locations proximate the patient's spine.

In some embodiments, the image data comprises data representing tissue selected from the group consisting of: wall tissue of a blood vessel of the patient site; thrombus proximate the patient site; occlusive matter proximate the patient site; a blood vessel outside of blood vessel in which the optical assembly is positioned; tissue outside of blood vessel in which the optical assembly is positioned; extracellular deposits outside of the lumen of the blood vessel in which optical assembly is positioned; and combinations thereof.

In some embodiments, step (e) further comprises collecting image data of an implanted device proximate the patient site, and the image created in step (f) further comprises one or more images of the implanted device. The implanted device can comprise a device selected from the group consisting of: flow diverter; aneurysm repair implant; stent; covered stent; coil; and combinations thereof. Step (e) can further comprise collecting image data of an implant placement procedure, and the image created in step (f) can further comprise creating one or more images of the implant placement procedure. Step (e) can further comprise collecting image data of a treatment device, and the image created in step (f) can further comprise creating one or more images of the treatment device. Step (f) can further comprise creating one or more images of the treatment procedure.

In some embodiments, the at least one delivery device comprises at least one delivery catheter constructed and arranged to slidingly receive the imaging probe. The at least one delivery catheter can comprise a catheter from the group consisting of: a 6 Fr to 8 Fr guide catheter; a 5 Fr to 6 Fr intermediate catheter; a microcatheter with an ID between 0.0165" and 0.027" (e.g. between 0.021" and 0.027"); and combinations thereof. The at least one delivery device can further comprise at least a first guidewire. The at least one delivery device can further comprise at least a second guidewire with an OD less than the OD of the first guidewire.

In some embodiments, the first delivery catheter comprises a proximal end, a distal end and a lumen therebetween, and the imaging probe can be advanced within the first delivery catheter. During step (b) the distal end of the first delivery catheter can be advanced to a location at least partially within the patient site, and during step (d) the first delivery catheter can be retracted to expose the optical assembly prior to performing the retraction of step (e). During step (e) the optical assembly can remain distal to the distal end of the first delivery catheter during the collection of the image data. During step (b) the distal end of the first delivery catheter can be advanced to a location proximal to the patient site, and during the collection of image data in step (e) the optical assembly can remain distal to the first delivery catheter distal end. During step (b) the distal end of the first delivery catheter can be advanced to a location at least partially within the patient site, and during the collection of image data in step (e) the optical assembly can remain within first delivery catheter. The first delivery catheter can comprise a transparent segment, and the optical assembly can remain within the transparent segment during the collection of image data in step (e).

In some embodiments, the at least one delivery device comprises a first guidewire and a microcatheter comprising an ID of between 0.0165" and 0.027" (e.g. between 0.021" and 0.027"), and the method comprises: advancing the first guidewire to a location within or distal to the patient site; advancing the microcatheter over the first guidewire to a location within or distal to the patient site; removing the first guidewire and inserting the imaging probe through the microcatheter to a location within or distal to the patient site; retracting the microcatheter to expose the optical assembly; and flushing through at least one of the microcatheter or another delivery catheter while retracting the optical assembly during the image data collection of step (e). The method can further comprise removing the imaging probe from the microcatheter and inserting a second guidewire through the first delivery catheter. The first guidewire can comprise the second guidewire. The second guidewire can comprise a different guidewire than the first guidewire. The patient site can comprise a patient site selected from the group consisting of: aneurysm; stenosis; thrombus; implant; and combinations thereof, and the imaging probe can be advanced at least within the patient site.

In some embodiments, the at least one delivery device comprises a first guidewire and a microcatheter comprising an ID of between 0.0165" and 0.027" (e.g. between 0.021" and 0.027"), and a distal portion comprising a transparent segment, and the method comprises: advancing the first guidewire to a location within or distal to the patient site; advancing the microcatheter over the first guidewire to a location within or distal to the patient site; removing the first guidewire and inserting the imaging probe through the microcatheter to a location within or distal to the patient site; flushing through at least one of the microcatheter or another delivery catheter while retracting the optical assembly during the image data collection of step (e), and the optical assembly remains within the microcatheter transparent segment. The method can further comprise removing the imaging probe from the microcatheter and inserting a second guidewire through the first delivery catheter. The first guidewire can comprise the second guidewire. The second guidewire can comprise a different guidewire than the first guidewire. The patient site can comprise a neural site or a cardiac site selected from the group consisting of: aneurysm; stenosis; thrombus; implant; and combinations thereof, and the imaging probe can be advanced at least within the patient site.

In some embodiments, the first delivery catheter comprises a distal portion including one or more sideholes, and the method further comprises delivering injectate in a flushing procedure that causes the injectate to pass through the one or more sideholes (e.g. injectate exits the lumen of the first delivery catheter via the one or more sideholes). The first delivery catheter can comprise a microcatheter with an ID less than or equal to 0.027".

In some embodiments, the first delivery catheter is advanced to a location proximate the patient site, and the method comprises advancing the imaging probe optical assembly beyond the distal end of the first delivery catheter.

In some embodiments, the method further comprises implanting an implantable device. The implantable device can comprise a device selected from the group consisting of: a flow diverter; a Pipeline™ flow diverter; a Surpass™ flow diverter; an embolization coil; a stent; a Wingspan™ stent; a covered stent; an aneurysm treatment implant; and combinations thereof. The patient site can comprise the implanted device or a site in which the implanted device will be implanted, and the method can comprise advancing the imaging probe optical assembly to the patient site; collecting image data of the patient site; analyzing the image data collected; and implanting the implantable device based on the analysis. The analysis can modify an implantation parameter selected from the group consisting of: selection of the implantable device; selection of the implantable device porosity; selection of the implantable device coverage (e.g. percentage of the surface area of vessel covered by metal or other material of the implantable device); selection of the implantable device pore density; selection of the implantable device diameter; selection of the implantable device length; selection of the location to implant the implantable device; a dilation parameter for expanding the implantable device once implanted; a repositioning of the implantable device once implanted; selection of a second implantable device to be implanted; and combinations thereof.

In some embodiments, the method comprises accessing the patient site with the optical assembly; collecting image data of the implanted device; analyzing the image data and identifying at least one implantation issue; and adjusting the implantation of the implanted device. The implantation issue identified can comprise an issue selected from the group consisting of: malposition of implanted device; inadequate deployment of implanted device; presence of air bubbles; and combinations thereof.

In some embodiments, the method further comprises advancing a diagnostic and/or treatment device through the first delivery catheter while the imaging probe resides within the first delivery catheter. The first delivery catheter can comprise an ID between 0.050" and 0.085". The first delivery catheter can comprise an ID between 0.053" and 0.072". The first delivery catheter can comprise an ID between 0.070" and 0.072". The diagnostic and/or treatment device can be advanced within the first delivery catheter prior to Step (c). The diagnostic and/or treatment device can be advanced within the first delivery catheter after Step (c). The diagnostic and/or treatment device can comprise an OD less than or equal to 0.035". The diagnostic and/or treatment device can comprise an OD less than or equal to 0.030". The diagnostic and/or treatment device can comprise an OD less than or equal to 0.025". The diagnostic and/or treatment device can comprise an OD less than or equal to 0.020". The method can further comprise automatically detecting the delivery of a flushing material. The diagnostic and/or treatment device can comprise a treatment device configured to deliver one or more coils to treat an aneurysm. The diagnostic and/or treatment device can comprise a treatment device configured to remove thrombus. The diagnostic and/or treatment device can comprise a treatment device configured to deliver a stent. The treatment device can be configured to deliver a covered stent. The method can further comprise: performing a clinical procedure with the diagnostic and/or treatment device; performing an assessment of the image data; and determining if an additional clinical procedure is desired based on the image data. The assessment of the image data can comprise a review of a 2D and/or 3D image of the patient site PS prior to, during and/or after the clinical procedure. The assessment of the image data can comprise a review of a 2D and/or 3D image of any implants implanted in the patient during the procedure. The assessment can determine one or more of: sufficient occlusion; sufficient occlusion of an aneurysm by implantation of coils or a covered stent; adequate positioning of an implant with tissue; adequate apposition of an implant with tissue; adequate flow through a native vessel; and combinations thereof. The method can further comprise: performing an additional clinical procedure; and collecting additional image data related to the additional clinical procedure. The additional clinical procedure can comprise a procedure selected from the group consisting of: implantation of one or more additional implants; additional dilation of an implant; and combinations thereof.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

FIGS. 6A-E are schematic anatomical views of a series of steps for creating an image, including advancing an imaging probe beyond the distal end of a delivery catheter prior to collecting image data, consistent with the present inventive concepts.

FIGS. 7A-E are schematic anatomical views of a series of steps for creating an image, including retracting a delivery catheter to uncover an optical assembly of an imaging probe prior to collecting image data, consistent with the present inventive concepts.

DETAILED DESCRIPTION OF THE DRAWINGS

Figure 1:
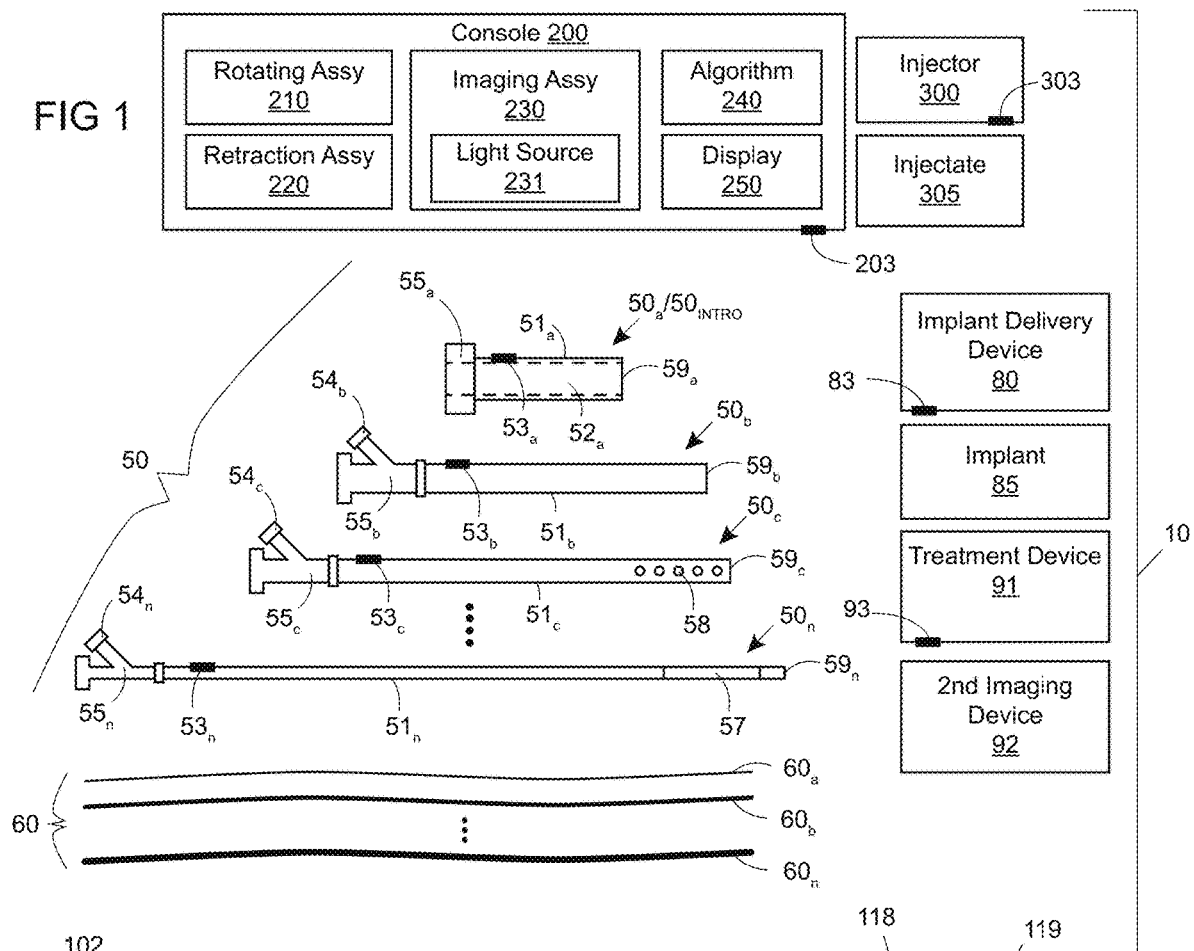
FIG. 1 is a schematic view of an imaging system comprising an imaging probe and one or more delivery devices, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element);

positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such as light (e.g. a transducer comprising a light emitting diode or light bulb), sound (e.g. a transducer comprising a piezo crystal configured to deliver ultrasound energy), pressure, heat energy, cryogenic energy, chemical energy; mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one or more of these.

As used herein, the term "patient site" refers to a location within the patient, such as a location within a body conduit such as a blood vessel (e.g. an artery or vein such as an artery or vein of the heart) or a segment of the GI tract (e.g. the esophagus, stomach or intestine), or a location within an organ. A "patient site" can refer to a location in the spine, such as within the epidural space or intrathecal space of the spine. A patient site can include a location including one or more of: an aneurysm; a stenosis; thrombus and/or an implant.

As used herein, the term "neural site" refers to a patient site proximate the brain, such as at a location within the neck, head or brain of a patient. A neural site can include a location proximate the brain including one or more of: an aneurysm; a stenosis; thrombus and/or an implant.

As used herein, the term "proximate" shall include locations relatively close to, on, in and/or within a referenced component or other location.

As used herein, the term "transparent" and "optically transparent" refer to a property of a material that is relatively transparent (e.g. not opaque) to light delivered and/or collected by one or more components of the imaging system or probe of the present inventive concepts (e.g. to collect image data of a patient site).

It is appreciated that certain features of the inventive concepts, which are, for clarity, described in the context of separate embodiments, may also be provided in combination in a single embodiment. Conversely, various features of the inventive concepts which are, for brevity, described in the context of a single embodiment, may also be provided separately or in any suitable sub-combination. For example, it will be appreciated that all features set out in any of the claims (whether independent or dependent) can be combined in any given way.

The present inventive concepts include imaging systems comprising imaging probes (e.g. optical imaging probes) and one or more delivery devices, such as delivery catheters and/or guidewires. The imaging probe can be configured to be positioned proximate a patient site and to collect image data from the patient site, such as a neural site, spinal site, cardiac site and/or other patient site (e.g. as defined hereabove). The imaging probe comprises an elongate shaft including a lumen. In some embodiments, a rotatable optical core and a distally positioned optical assembly are positioned within the lumen of the probe shaft. The present inventive concepts further includes methods of introducing the imaging probe to a patient site, such as a neural site or cardiac site, using one or more delivery devices such as delivery catheters and/or guidewires. In some embodiments, the imaging probe is advanced through a delivery catheter to a patient site, without being advanced over a guidewire.

Referring now to FIG. 1, a schematic view of an imaging system comprising an imaging probe and one or more delivery devices is illustrated, consistent with the present inventive concepts. System 10 is constructed and arranged to collect image data and produce an image based on the recorded data, such as when system 10 comprises an Optical Coherence Tomography (OCT) imaging system. System 10 comprises imaging probe 100, and at least one delivery device, such as at least one delivery catheter 50 and/or at least one guidewire 60. System 10 can further comprise console 200 which is configured to operably attach to imaging probe 100. System 10 can further comprise a fluid injector, such as injector 300 which can be configured to inject one or more fluids, such as a flushing fluid, an imaging contrast agent (e.g. a radiopaque contrast agent, hereinafter "contrast") and/or other fluid, such as injectate 305 shown. System 10 can further comprise an implant, such as implant 85 which can be implanted in the patient via implant delivery device 80. System 10 can further comprise a device configured to treat the patient, treatment device 91, which can be configured to dilate a stenotic site, remove stenotic material (e.g. thrombus) and/or otherwise treat a patient disease or disorder. System 10 can further comprise a second imaging device, such as imaging device 92 shown.

Imaging probe 100 comprises an elongate shaft, shaft 110, comprising proximal end 111, distal end 119, mid portion 115, and distal portion 118. A connector, connector 102 is positioned on the proximal end 111 of shaft 110, such as a connector configured to operably attach probe 100 to console 200. Imaging probe 100 is configured to provide a patient image (e.g. a three dimensional image created when shaft 110 of imaging probe 100 is retracted). In some embodiments, imaging probe 100 and/or another component of system 10 is of similar construction and arrangement to the similar components described in applicant's U.S. Provisional Application Ser. No. 62/148,355, titled "Micro-Optic Probes for Neurology", filed Apr. 29, 2015, the content of which is incorporated herein in its entirety.

Imaging probe 100 is constructed and arranged to collect image data from a patient site, such as patient site PS shown in FIG. 5, 6A-E, 7A-E, 8A-D, 9A-C, 10A-E or 12. In these embodiments, the distal portion 118 can be configured to pass through the patient site, such as a patient site including occlusive material such as thrombus or a patient site including an implant. In some embodiments, probe 100 is constructed and arranged to collect image data from a neural site, such as a neural site selected from the group consisting of: artery of patient's neck; vein of patient's neck; artery of patient's head; vein of patient's head; artery of patient's brain; vein of patient's brain; and combinations of one or more of these. In some embodiments, probe 100 is constructed and arranged to collect image data from a cardiac site, such as a cardiac site selected from the group consisting of: artery of the heart; vein of the heart; atrium of the heart; ventricle of the heart; and combinations of one or more of these. In some embodiments, probe 100 is constructed and arranged to collect image data from one or more locations along or otherwise proximate the patient's spine. In some embodiments, probe 100 is constructed and arranged to collect image data from tissue selected from the group consisting of: wall tissue of a blood vessel of the patient site; thrombus proximate the patient site; occlusive matter proximate the patient site; a blood vessel outside of blood vessel in which optical assembly 130 is positioned; tissue outside of blood vessel in which optical assembly 130 is positioned; extracellular deposits outside of the lumen of the blood vessel in which optical assembly 130 is positioned (e.g. within and/or outside of the blood vessel wall); and combinations of one or more of these. Alternatively or additionally, optical assembly 130 can be constructed and arranged to collect image data from an implanted device (e.g. a temporary or chronically implanted device), such as implant 85 described herebelow or a device previously implanted in the patient. In some embodiments, optical assembly 130 is constructed and arranged to collect image data regarding the placement procedure in which the implant was positioned within the patient (e.g. real time data collected during placement). Optical assembly 130 can be constructed and arranged to collect implant data comprising position and/or expansion data related to placement of an implant or other treatment device, such as a device selected from the group consisting of: a stent retriever (also known as a stentriever); an embolization device such as an embolization coil; an occlusion device; a flow diverter; and combinations of one or more of these. In some embodiments, optical assembly 130 is constructed and arranged to collect data related to the position of an implant 85 or other device comprising a stimulation element, such as an electrode or other stimulation element positioned proximate the brain (e.g. an electrode positioned in the deep brain or other brain location) or a stimulation element positioned proximate the spine (e.g. stimulation element configured to treat pain by stimulating spine tissue). Implantation of implant 85 can be performed based on an analysis of collected image data (e.g. an analysis of collected image data by algorithm 240). The analysis can be used to modify an implantation parameter selected from the group consisting of: selection of the implantable device (e.g. selection of implant 85); selection of the implantable device porosity; selection of the implantable device coverage (e.g. percentage of the surface area of vessel covered by metal or other material of the implantable device); selection of the implantable device pore density; selection of the implantable device diameter; selection of the implantable device length; selection of the location to implant the implantable device; a dilation parameter for expanding the implantable device once implanted; a repositioning of the implantable device once implanted; selection of a second implantable device to be implanted; and combinations thereof. An adjustment of the implantation can be performed based on one or more issues identified in the analysis, such as an issue selected from the group consisting of: malposition of implanted device; inadequate deployment of implanted device; presence of air bubbles; and combinations thereof.

In some embodiments, optical assembly 130 is constructed and arranged to collect data related to the position of a treatment device, such as treatment device 91 described herebelow, during a patient treatment procedure.

Delivery catheters 50 can comprise one or more delivery catheters, such as delivery catheters 50a, 50b, 50c through 50n shown. Delivery catheters 50 can include a vascular introducer, such as when delivery catheter 50a shown in FIG. 1 comprises a vascular introducer, delivery catheter $50_{INTRO}$. Other delivery catheters 50 can be inserted into the patient through delivery catheter $50_{INTRO}$, after the vascular introducer is positioned through the skin of the patient. Two or more delivery catheters 50 can collectively comprise sets of inner diameters (IDs) and outer diameters (ODs) such that a first delivery catheter 50 slidingly receives a second delivery catheter 50 (e.g. the second delivery catheter OD is less than or equal to the first delivery catheter ID), and the second delivery catheter 50 slidingly receives a third delivery catheter 50 (e.g. the third delivery catheter OD is less than or equal to the second delivery catheter ID), and so on. In these configurations, the first delivery catheter 50 can be advanced to a first anatomical location, the second delivery catheter 50 can be advanced through the first delivery catheter to a second anatomical location distal or otherwise remote (hereinafter "distal") to the first anatomical location, and so on as appropriate, using sequentially smaller diameter delivery catheters 50.

Each delivery catheter 50 comprises a shaft 51 (e.g. shafts 51a, 51b, 51c and 51n shown), each with a distal end 59 (e.g. distal ends 59a, 59b, 59c and 59n shown). A connector 55 (e.g. connectors 55a, 55b, 55c and 55n shown) is positioned on the proximal end of each shaft 51. Each connector 55 can comprise a Touhy or other valved connector, such as a valved connector configured to prevent fluid egress from the associated catheter 50 (with and/or without a separate shaft positioned within the connector 55). Each connector 55 can comprise a port 54 (e.g. ports 54b, 54c and 54n as shown on delivery catheters 50b, 50c, and 50n), such as a port constructed and arranged to allow introduction of fluid into the associated delivery catheter 50 and/or for removing fluids from an associated delivery catheter 50. In some embodiments, a flushing fluid, as described herebelow, is introduced via one or more ports 54, such as to remove blood or other undesired material from locations proximate optical assembly 130. Port 54 can be positioned on a side of connector 55 and can include a luer fitting and a cap and/or valve. Shafts 51, connectors 55 and ports 54 can each comprise standard materials and be of similar construction to commercially available introducers, guide catheters, diagnostic catheters, intermediate catheters and microcatheters used in interventional procedures.

Each delivery catheter 50 comprises a lumen 52 (reference number 52 shown on delivery catheter 50a but removed from the remaining delivery catheters 50 for illustrative clarity) extending from the connector 55 to the distal end 59 of shaft 51. The diameter of each lumen 52 defines the ID of the associated delivery catheter 50. Each delivery catheter 50 can be advanced over a guidewire (e.g. guidewire 60) via lumen 52. In some embodiments, a delivery catheter 50 is configured for rapid exchange advancement and retraction over a guidewire, such as via a sidecar as described herebelow in reference to FIG. 4B. In some embodiments, probe 100 and at least one delivery catheter 50 are cooperatively constructed and arranged such that the delivery catheter 50 is advanced through a vessel, such as a blood vessel, and probe 100 is slidingly received by the delivery catheter 50 and advanced through the delivery catheter 50 to a location proximate a patient site PS to be imaged (e.g. a location just distal to, within and/or just proximate the patient site PS to be imaged). In some embodiments, a second delivery catheter 50 is slidingly received by a first delivery catheter 50, and probe 100 is advanced through the second delivery catheter 50 to a location proximate a patient site PS to be imaged. In yet other embodiments, three or more delivery catheters 50 are coaxially inserted into each other, with probe 100 advanced through the innermost delivery catheter 50 to a location proximate a patient site PS to be imaged. In some embodiments, probe 100 is advanced through (e.g. through and beyond) one or more delivery catheters 50 without the use of a guidewire.

Delivery catheters 50 can comprise one or more delivery catheters selected from the group consisting of: an introducer; a vascular introducer; an introducer with an ID between 7 Fr and 9 Fr; a delivery catheter (also referred to as a guide catheter) for positioning through the aortic arch (e.g. such that it's distal end is just distal or otherwise proximate the aortic arch) such as a delivery catheter with an ID between 5 Fr and 7 Fr or an ID of approximately 6.5 Fr; a delivery catheter (also referred to as an intermediate catheter) for insertion through a larger, previously placed delivery catheter, such as an intermediate delivery catheter with an ID of between 0.053" and 0.070"; a delivery catheter (also referred to as a microcatheter) with an ID of between 0.0165" and 0.027"; and combinations of one or more of these. In some embodiments, delivery catheters 50 comprise a first delivery catheter $50_{INTRO}$ comprising an introducer, such as an introducer with an ID of between 7 Fr and 9 Fr or an ID of approximately 8 Fr. Delivery catheters 50 can further comprise a second delivery catheter 50 constructed and arranged to be inserted into the first delivery catheter 50, such as a second delivery catheter $50_{GUIDE}$, which can be constructed and arranged for positioning through the aortic arch and comprising an ID between 5 Fr and 7 Fr or an ID of approximately 6.5 Fr. Delivery catheters 50 can comprise a third delivery catheter 50 constructed and arranged to be inserted through the first delivery catheter $50_{INTRO}$ and/or the second delivery catheter $50_{GUIDE}$, such as a third delivery catheter $50_{INTER}$ with an ID of between 0.053" and 0.070". Delivery catheters 50 can comprise a fourth delivery catheter $50_{MICRO}$ constructed and arranged to be inserted through the first, second and/or third delivery catheters 50, such as a fourth delivery catheter $50_{MICRO}$ with an ID of between 0.0165" to 0.027". Imaging probe 100 can be constructed and arranged to be inserted through first, second, third and/or fourth delivery catheters 50, such as when imaging probe 100 comprises an OD of less than 0.070", such as when at least the distal portion of imaging probe 100 comprises an OD of less than or equal to 0.025", 0.022", 0.018", 0.016", 0.015" or 0.014". In some embodiments, at least the distal portion of imaging probe 100 comprises an ID of approximately 0.014" (e.g. an ID between 0.012" and 0.016"). In some embodiments, system 10 comprises a probe 100 and one or more delivery catheters 50 as described herebelow in reference to FIG. 2 or 5.

Each delivery catheter 50 can comprise an optically transparent segment, such as a segment relatively transparent to light transmitted and/or received by optical assembly 130, such as transparent segment 57 shown on delivery catheter 55n and described herein. Transparent segment 57 can comprise a length of up to 50 cm, such as a length of between 1 cm and 15 cm, or a length of up to 2 cm or up to 5 cm.

Each delivery catheter 50 can comprise a spring tip, not shown but such as spring tip 104 described herein as attached to shaft 110 of probe 100.

Guidewires 60 can comprise one or more guidewires, such as guidewires 60a, 60b through 60n shown. Guidewires 60 can comprise one or more guidewires constructed and arranged to support advancement (e.g. intravascular advancement) of probe 100 (e.g. via a rapid exchange lumen in distal portion 118 of shaft 110) and/or a delivery catheter 50 into a patient site PS such as a neural site or a cardiac site. Guidewires 60 can comprise one or more guidewires selected from the group consisting of: a guidewire with an OD between 0.035" and 0.038"; a guidewire with an OD between 0.010" and 0.018"; an access length guidewire such as a guidewire with a length of approximately 200 cm; an exchange length guidewire such as a guidewire with a length of approximately 300 cm; a guidewire with a length between 175 cm and 190 cm; a guidewire with a length between 200 cm and 300 cm and/or an OD between 0.014" and 0.016"; a hydrophilic guidewire; a Stryker Synchro™ guidewire; a Terumo guidewire such as the Terumo Glidewire™ guidewire; a Terumo Traxcess™ guidewire; an X-Celerator™ guidewire; an X-Pedion™ guidewire; an Agility™ guidewire; a Bentson™ guidewire; a Coon™ guidewire; an Amplatz™ guidewire; and combinations of one or more of these. In some embodiments, system 10 comprises a probe 100 and one or more guidewires 60 as described herebelow in reference to FIG. 2 or 5. Guidewires 60 can comprise one or more visualizable portions, such as one or more radiopaque or ultrasonically reflective portions.

System 10 can comprise various sets and configurations of delivery catheters 50 and guidewires 60. In some embodiments, delivery catheters 50 comprise a first delivery catheter 50$_{INTRO}$ comprising an introducer (e.g. a vascular introducer), and at least two delivery catheters 50 that are inserted through delivery catheter 50$_{INTRO}$, these catheters comprising corresponding different sets of IDS and ODS, such as to allow sequential insertion of each delivery catheter 50 through the lumen 52 of a previously placed delivery catheter 50, as described in detail herein. In some embodiments, a first delivery catheter 50 is advanced over a first guidewire 60, and a smaller OD delivery catheter 50 is subsequently advanced over a smaller OD guidewire 60 (e.g. after the first guidewire 60 is removed from the first delivery catheter 50 and replaced with the second guidewire 60). In some embodiments, after image data is collected by an imaging probe 100 positioned within a delivery catheter (e.g. after a retraction in which the image data is collected), imaging probe 100 is removed and replaced with a guidewire 60 over which an additional device can be placed (e.g. another delivery catheter 50, a treatment device 91, an implant delivery device 80 or other device). In some embodiments, probe 100, one or more delivery catheters 50 and/or one or more guidewires 60 are inserted, advanced and/or retracted as described herebelow in reference to FIG. 2, 5, 6A-E, 7A-E, 8A-D, 9A-C or 10A-E.

As an alternative to advancement of probe 100, one or more delivery catheters 50 and/or one or more guidewires 60 through one or more blood vessels (e.g. advancement of or more delivery catheters 50 over a guidewire 60 through one or more arteries or veins), one or more of these devices can be advanced to a patient site PS via a non-blood vessel lumen, such as the epidural and/or intrathecal space of the spine, or via another body lumen or space (e.g. also as can be performed over a guidewire 60).

In some embodiments, one or more delivery catheters 50 comprise a functional element 53 (e.g. functional elements 53a, 53b, 53c and 53n shown). Each functional element 53 can comprise one or more functional elements such as one or more sensors, transducers and/or other functional elements as described in detail herebelow.

Figure 1A:
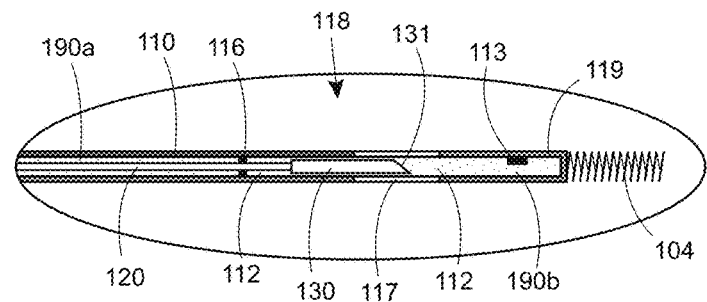
FIG. 1A is magnified view of the distal portion of the shaft of the imaging probe of FIG. 1, consistent with the present inventive concepts.

Referring additionally to FIG. 1A, a magnified view of distal portion 118 is illustrated, consistent with the present inventive concepts. A lumen 112 extends from proximal end 111 of shaft 110 to distal portion 118, ending at a location proximal to distal end 119. Positioned within lumen 112 is a rotating optical core, core 120. An optical assembly, optical assembly 130 is positioned on the distal end of core 120. Optical assembly 130 includes surface 131 which is positioned within an optically translucent and/or effectively transparent portion of shaft 110, viewing portion 117. Optical assembly 130 is constructed and arranged to collect image data through at least a portion of shaft 110 (e.g. through viewing portion 117). In some embodiments, optical assembly 130 is further constructed and arranged to collect image data through at least a portion of an additional device, such as at least a portion of a shaft of a delivery catheter 50 (e.g. an optically transparent portion of a delivery catheter 50, such as transparent segment 57 described herein). Connector 102 can be rotatably attached to core 120 (e.g. allowing rotation of core 120 relative to one or more portions of connector 102 while preventing longitudinal translation of core 120 relative to connector 120). In some embodiments, connector 102 is fixedly attached to shaft 110, such as to prevent all relative motion between connector 102 and shaft 110, such as to prevent longitudinal translation between shaft 110 and core 120 (e.g. when shaft 110 and optical assembly 130 are retracted in unison during image data collection as described herein).

In some embodiments, a fluid 190 is included in lumen 112 (e.g. in the space not occupied by core 120 and optical assembly 130), such as fluid 190a and fluid 190b shown in FIG. 1A. Fluid 190 (e.g. fluid 190b) can comprise an optically transparent fluid. In some embodiments, fluid 190a and fluid 190b comprise similar materials. Alternatively or additionally, fluid 190a and fluid 190b can comprise dissimilar materials. In some embodiments, fluid 190a comprises a more viscous fluid than fluid 190b. Fluid 190 can be constructed and arranged to limit undesired variations in rotational velocity of core 120 and/or optical assembly 130. In some embodiments, fluid 190 comprises a non-newtonian fluid or other fluid whose viscosity changes with shear. In some embodiments, a seal is included in lumen 112, sealing element 116, constructed and arranged to provide a seal between optical core 120 and the walls of shaft 110. Sealing element 116 can allow for the rotation of optical core 120, while preventing the mixing and/or migrating of fluids 190a and 190b.

Shaft 110 can comprise one or more materials, and can comprise at least a portion which is braided. In some embodiments, at least the distal portion 118 of shaft 110 comprises an OD less than or equal to 0.025", such as an OD less than or equal to 0.022", 0.018", 0.016", 0.015" or 0.014". In some embodiments, shaft 110 comprises a material selected from the group consisting of: polyether ether ketone (PEEK), polyimide, nylon; fluorinated ethylene propylene (FEP); polytetrafluoroethylene (PTFE); polyether block amide (Pebax); and combinations of one or more of these. In some embodiments, shaft 110 comprises at least a portion including a braid including stainless steel and/or a nickel titanium alloy, such as a shaft 110 that includes a braid positioned over thin walled FEP or PTF. The braided portion can be coated with Pebax or other flexible material.

Viewing portion 117 of shaft 110 can comprise one or more materials, and can comprise similar or dissimilar materials to a different portion of shaft 110. Viewing portion 117 can comprise a similar ID and/or OD as one or more other portions of shaft 110. In some embodiments, viewing portion 117 comprises an inner and/or outer diameter that is larger than an inner and/or outer diameter of shaft 110 at mid portion 115 of shaft 110. Viewing portion 117 can comprise a similar or dissimilar flexibility as one or more other portions of shaft 110. Viewing portion 117 can comprise one or more optically transparent materials selected from the group consisting of: Pebax; amorphous PEEK; polyimide; glass; sapphire; and combinations of one or more of these.

In some embodiments, a flexible tip portion is positioned on the distal end of shaft 110, such as spring tip 104 shown. Spring tip 104 can comprise a length of between 0.5 cm and 5 cm, such as a length of approximately 1 cm, 2 cm or 3 cm. At least a portion of spring tip 104 can be made visible to an imaging apparatus, such as by including a radiopaque material such as platinum visible to an X-ray imaging device. Spring tip 104 can comprise a core comprising a material such as stainless steel.

Console 200 can comprise an assembly, rotating assembly 210 constructed and arranged to rotate at least rotatable optical core 120. Console 200 can comprise an assembly, retraction assembly 220, constructed and arranged to retract shaft 110 and/or optical assembly 130. In some embodiments, retraction assembly 220 and probe 100 can be configured such that during image data collection, retraction assembly 220 retracts optical assembly 130 and shaft 110 in unison. In these embodiments, shaft 110 can comprise a relatively short viewing window, viewing portion 117 surrounding optical assembly 130, since optical assembly 130 does not translate within shaft 110. For example, in these embodiments, viewing portion 117 can comprise a length less than or equal to 20 mm, less than or equal to 15 mm, less than or equal to 6 mm, or less than or equal to 4 mm, such as when viewing portion 117 comprises a length of approximately 3 mm. In these embodiments in which viewing portion 117 comprises a relative short length, viewing portion 117 can comprise a material that is softer and/or more flexible than other portions of shaft 110 (e.g. without significantly impacting the column and/or torsional strength of probe 100). In some embodiments, viewing portion 117 comprises a length between 5 mm and 50 mm, such as a length of approximately 10 mm or approximately 12 mm. In these embodiments in which optical assembly 130 does not translate within shaft 110, shaft 110 diameter (ID and/or OD) can be reduced at locations proximal to viewing portion 117, such as when the OD of shaft 110 (at least the portion of shaft 110 surrounding and proximate optical assembly), comprises an OD of less than or equal to 0.025", 0.016" or 0.014". Alternatively or additionally, in these embodiments in which optical assembly 130 does not translate within shaft 110, portions of the shaft proximal to optical assembly 130 (e.g. proximal to viewing portion 117) can include a non-transparent construction, such as a braided construction or a construction using materials such as metal tubing (e.g. nitinol or stainless steel hypotube), such as to improve pushability of probe 100. Rotating assembly 210 and/or retraction assembly 220 can be of similar construction and arrangement to those described herebelow in reference to FIG. 13. Console 200 can comprise an imaging assembly 230 configured to provide light to optical assembly 130 (e.g. via core 120) and collect light from optical assembly 130 (e.g. via core 120). Imaging assembly 230 can include a light source 231. Light source 231 can comprise one or more light sources, such as one or more light sources configured to provide one or more wavelengths of light to optical assembly 130 via core 120. Light source 231 is configured to provide light to optical assembly 130 (via core 120) such that image data can be collected comprising cross-sectional, longitudinal and/or volumetric information related to the patient site PS or implanted device being imaged. Light source 231 can be configured to provide light such that the image data collected includes characteristics of tissue within the patient site PS being imaged, such as to quantify, qualify or otherwise provide information related to a patient disease or disorder present within the patient site PS being imaged. Light source 231 can be configured to deliver broadband light and have a center wavelength in the range from 800 nm to 1700 nm, from 1280 nm and 1310 nm, or approximately 1300 nm (e.g. light delivered with a sweep range from 1250 nm to 1350 nm). The light source 231 bandwidth can be selected to achieve a desired resolution, which can vary according to the needs of the intended use of system 10. In some embodiments, bandwidths are about 5% to 15% of the center wavelength, which allows resolutions of between 5 microns and 20 microns. Light source 231 can be configured to deliver light at a power level meeting ANSI Class 1 ("eye safe") limits, though higher power levels can be employed. In some embodiments, light source 231 delivers light in the 1.3 μm band at a power level of approximately 20 mW. Tissue light scattering is reduced as the center wavelength of delivered light increases, however water absorption increases. Light source 231 can deliver light at a wavelength approximating 1300 nm to balance these two effects. Light source 231 can be configured to deliver shorter wavelength light (e.g. approximately 800 nm light) to traverse patient sites to be imaged including large amounts of fluid. Alternatively or additionally, light source 231 can be configured to deliver longer wavelengths of light (e.g. approximately 1700 nm light), such as to reduce a high level of scattering within a patient site to be imaged.

Rotational assembly 210 can be constructed and arranged to rotate core 120 (and subsequently one or more components of optical assembly 130) at a rotational velocity of approximately 250 rps, or at a rotational velocity between 40 rps and 1000 rps. In some embodiments, rotational assembly 210 is constructed and arranged to rotate core 120 at one rate (e.g. at least 50 rps or approximately 250 rps) during image data collection (i.e. an "imaging mode"), and at a different rate (e.g. a slower rate, such as a rate between 30 rps and 150 rps) during a "preview mode". During preview mode, a "positioning operation" can be performed in which optical assembly 130 is linearly positioned and/or a flush procedure can be initiated. The positioning operation can be configured to visualize bright reflections (e.g. via one or more implants such as an implanted stent, flow director and/or coils). Alternatively or additionally, the preview mode can be configured to allow an operator (e.g. a clinician) to confirm that optical assembly 130 has exited the distal end 59 of a surrounding delivery catheter 50. The preview mode can be configured to reduce time and acceleration forces associated with rotating core 120 at a velocity to accommodate image data collection (e.g. a rotational velocity of at least 150 rps or approximately 250 rps).

Retraction assembly 220 can be constructed and arranged to retract optical assembly 130 (e.g. by retracting shaft 100) at a retraction rate of approximately 40 mm/sec, such as a retraction rate between 5 mm/sec and 60 mm/sec. Retraction assembly 220 can be constructed and arranged to perform a pullback of between 20 mm and 100 mm. such as a pullback that is performed in a time period between 1.0 seconds and 15.0 seconds.

Console 200 can comprise a display 250, such as a display configured to provide one or more images (e.g. video) based on the collected image data. Imaging assembly 230 can be configured to provide an image on display 250 with an updated frame rate of up to approximately 250 frames per second (e.g. similar to the rotational velocity of core 120). Display 250 can provide a 2-D and/or 3-D representation of 2-D and/or 3-D data.

Console 200 can comprise one or more functional elements, such as functional element 203 shown in FIG. 1. Functional element 203 can comprise one or more functional elements such as one or more sensors, transducers and/or other functional elements as described in detail herebelow.

Console 200 can comprise an algorithm, such as algorithm 240 shown, which can be configured to adjust (e.g. automatically and/or semi-automatically adjust) one or more operational parameters of system 10, such as an operational parameter of console 200, probe 100 and/or a delivery catheter 50. Alternatively or additionally, algorithm 240 can be configured to adjust an operational parameter of a separate device, such as injector 300 or implant delivery device 80 described herebelow. In some embodiments, algorithm 240 is configured to adjust an operational parameter based on one or more sensor signals, such as a sensor signal provided by a sensor-based functional element of the present inventive concepts as described herein (e.g. a signal provided by one or more of functional elements 53, 83, 93, 103, 203, 303). Algorithm 240 can be configured to adjust an operational parameter selected from the group consisting of: a rotational parameter such as rotational velocity of core 120 and/or optical assembly 130; a retraction parameter of shaft 110 and/or optical assembly 130 such as retraction velocity, distance, start position, end position and/or retraction initiation timing (e.g. when retraction is initiated); a position parameter such as position of optical assembly 130; a line spacing parameter such as lines per frame; an image display parameter such as a scaling of display size to vessel diameter; a probe 100 configuration parameter; an injectate 305 parameter such as a saline to contrast ratio configured to determine an appropriate index of refraction; a light source 231 parameter such as power delivered and/or frequency of light delivered; and combinations of one or more of these. In some embodiments, algorithm 240 is configured to adjust a retraction parameter such as a parameter triggering the initiation of the pullback, such as a pullback that is initiated based on a parameter selected from the group consisting of: lumen clearing; injector 300 signal; change in image data collected (e.g. a change in an image, based on the image data collected, that correlates to proper evacuation of blood from around optical assembly 130); and combinations of one or more of these. In some embodiments, algorithm 240 is configured to adjust a probe 100 configuration parameter, such as when algorithm 240 identifies (e.g. automatically identifies via an RF or other embedded ID) the attached probe 100 and adjusts a parameter such as arm path length and/or other parameter as listed above.

Injector 300 can comprise a power injector, syringe pump, peristaltic pump or other fluid delivery device configured to inject a contrast agent, such as radiopaque contrast, and/or other fluids. In some embodiments, injector 300 is configured to deliver contrast and/or other fluid (e.g. contrast, saline and/or Dextran). In some embodiments, injector 300 delivers fluid in a flushing procedure as described herebelow. In some embodiments, injector 300 delivers contrast or other fluid through a delivery catheter 50 with an ID of between 5 Fr and 9 Fr, a delivery catheter 50 with an ID of between 0.53" to 0.70", or a delivery catheter 50 with an ID between 0.0165" and 0.027". In some embodiments, contrast or other fluid is delivered through a delivery catheter as small as 4 Fr (e.g. for distal injections). In some embodiments, injector 300 delivers contrast and/or other fluid through the lumen of one or more delivery catheters 50, while one or more smaller delivery catheters 50 also reside within the lumen 52. In some embodiments, injector 300 is configured to deliver two dissimilar fluids simultaneously and/or sequentially, such as a first fluid delivered from a first reservoir and comprising a first concentration of contrast, and a second fluid from a second reservoir and comprising less or no contrast. Injector 300 can comprise one or more functional elements, such as functional element 303 shown in FIG. 1. Functional element 303 can comprise one or more functional elements such as one or more sensors, transducers and/or other functional elements as described in detail herebelow.

Implant 85 can comprise an implant (e.g. a temporary or chronic implant) for treating one or more of a vascular occlusion or an aneurysm. In some embodiments, implant 85 comprises one or more implants selected from the group consisting of: a flow diverter; a Pipeline™ flow diverter; a Surpass™ flow diverter; an embolization coil; a stent; a Wingspan™ stent; a covered stent; an aneurysm treatment implant; and combinations of one or more of these. Delivery device 80 can comprise a catheter or other tool used to deliver implant 85, such as when implant 85 comprises a self-expanding or balloon expandable portion. Implant delivery device 80 can comprise a functional element, such as functional element 83 shown in FIG. 1. Functional element 83 can comprise one or more functional elements such as one or more sensors, transducers and/or other functional elements as described in detail herebelow. In some embodiments, system 10 comprises a probe 100, one or more implants 85 and/or one or more implant delivery devices 80 as described herebelow in reference to FIG. 5. In some embodiments, probe 100 is configured to collect data related to implant 85 and/or implant delivery device 80 (e.g. implant 85 and/or implant delivery device 80 anatomical location, orientation and/or other configuration data), after implant 85 and/or implant delivery device 80 has been inserted into the patient.

Treatment device 91 can comprise an occlusion treatment or other treatment device selected from the group consisting of: a balloon catheter constructed and arranged to dilate a stenosis or other narrowing of a blood vessel; a drug eluting balloon; an aspiration catheter; a sonolysis device; an atherectomy device; a thrombus removal device such as a stent retriever device; a Trevo™ stentriever; a Solitaire™ stentriever; a Revive™ stentriever; an Eric™ stentriever; a Lazarus™ stentriever; a stent delivery catheter; a microbraid implant; an embolization system; a WEB™ embolization system; a Luna™ embolization system; a Medina™ embolization system; and combinations of one or more of these. In some embodiments, probe 100 is configured to collect data related to treatment device 91 (e.g. treatment device 91 location, orientation and/or other configuration data), after treatment device 91 has been inserted into the patient. Treatment device 91 can comprise a functional element, such as functional element 93 shown in FIG. 1.

$2^{nd}$ Imaging device 92 can comprise an imaging device such as one or more imaging devices selected from the group consisting of: an X-ray; a fluoroscope such as a single plane or biplane fluoroscope; a CT Scanner; an MRI; a PET Scanner; an ultrasound imager; and combinations of one or more of these.

Functional elements 53, 83, 93, 103, 113, 203, and/or 303 can each comprise one or more sensors, transducers and/or other functional elements, as described in detail herebelow.

In some embodiments, a functional element 113 is positioned proximate optical assembly 130 (e.g. distal to optical assembly 130 as shown in FIG. 1A, at the same axial location as optical assembly 130 and/or proximal to optical assembly 130). In some embodiments, imaging probe 100 comprises functional element 103 shown in FIG. 1. Functional element 103 is shown positioned on a proximal portion of shaft 110, however it can be positioned at another probe 100 location such as on, in and/or within connector 102. Functional elements 103 and/or 113 can each comprise one or more functional elements such as one or more sensors, transducers and/or other functional elements as described in detail herebelow.

In some embodiments, functional element 53, 83, 93, 103, 113, 203 and/or 303 comprise a sensor, such as a sensor configured to provide a signal related to a parameter of a system 10 component and/or a sensor configured to provide a signal related to a patient parameter. Functional element 53, 83, 93, 103, 113, 203 and/or 303 can comprise one or more sensors selected from the group consisting of: a physiologic sensor; a pressure sensor; a strain gauge; a position sensor; a GPS sensor; an accelerometer; a temperature sensor; a magnetic sensor; a chemical sensor; a biochemical sensor; a protein sensor; a flow sensor such as an ultrasonic flow sensor; a gas detecting sensor such as an ultrasonic bubble detector; a sound sensor such as an ultrasound sensor; and combinations of one or more of these. In some embodiments, functional element 53, 83, 93, 103, 113, 203 and/or 303 can comprise one or more physiologic sensors selected from the group consisting of: a pressure sensor such as a blood pressure sensor; a blood gas sensor; a flow sensor such as a blood flow sensor; a temperature sensor such as a blood or other tissue temperature sensor; and combinations of one or more of these. In some embodiments, algorithm 240 is configured to process the signal received by a sensor, such as a signal provided by a sensor as described herein. In some embodiments, functional element 53, 83, 93, 103 and/or 113 comprises a position sensor configured to provide a signal related to a vessel path (e.g. a vessel lumen path) in three dimensions. In some embodiments, functional element 53, 83, 93, 103 and/or 113 comprises a magnetic sensor configured to provide a signal for positioning optical assembly 130 relative to one or more implanted devices (e.g. one or more implants 85 described herein comprising a ferrous or other magnetic portion). In some embodiments, functional element 53, 83, 93, 103 and/or 113 comprises a flow sensor, such as a flow sensor configured to provide a signal related to blood flow through a blood vessel of the patient site PS (e.g. blood flow through a stenosis or other partially occluded segment of a blood vessel). In these embodiments, algorithm 240 can be configured to assess blood flow (e.g. assess the significance of an occlusion), such as to provide information to a clinician regarding potential treatment of the occlusion. In some embodiments, optical assembly 130 comprises functional element 113, such as when optical assembly 130 is constructed and arranged as a sensor that provides a signal related to blood flow. In some embodiments, functional element 53, 83, 93, 103 and/or 113 comprises a flow sensor configured to provide a signal used to co-register vessel anatomic data to flow data, which can be used to provide pre and post intervention modeling of flow (e.g. aneurysm flow), assess risk of rupture and/or otherwise assess adequacy of the intervention. In some embodiments, functional element 53, 83, 93, 103 and/or 113 comprises an ultrasound sensor configured to provide a signal (e.g. image or frequency data) which can be co-registered with near field optical derived information provided by optical assembly 130. In some embodiments, functional element 53, 83, 93, 103 and/or 113 are configured to be deployed by their associated device, such as to implant the functional element (e.g. a sensor-based functional element) into the patient. The implantable functional element 53, 83, 93, 103 and/or 113 can comprise microchip and/or MEMS components. The implantable functional element 53, 83, 93, 103 and/or 113 can comprise at least a portion that is configured to be visualized (e.g. by image data collected by probe 100 and/or a separate imaging device such as second imaging device 92).

In some embodiments, functional element 53, 83, 93, 103, 113, 203 and/or 303 can comprise one or more transducers selected from the group consisting of: a heating element such as a heating element configured to deliver sufficient heat to ablate tissue; a cooling element such as a cooling element configured to deliver cryogenic energy to ablate tissue; a sound transducer such as an ultrasound transducer; a vibrational transducer; and combinations of one or more of these.

In some embodiments, functional element 53, 83, 93, 103 and/or 113 comprises a pressure release valve configured to prevent excessive pressure from accumulating in the associated device. In some embodiments, functional element 53, 83, 93, 103 and/or 113 comprises one or more sideholes, such as one or more sideholes used to deliver a fluid in a flushing procedure as described herein.

In some embodiments, functional element 53, 83, 93, 103, 113, 203 and/or 303 comprise a visualizable marker, such as when functional element 53, 83, 93, 103 and/or 113 comprise a marker selected from the group consisting of: radiopaque marker; ultrasonically reflective marker; magnetic marker; ferrous material; and combinations of one or more of these.

Probe 100 is configured to collect image data, such as image data collected during rotation and/or retraction of optical assembly 130. Optical assembly 130 can be rotated by rotating core 120. Optical assembly 130 can be retracted by retracting shaft 110. Optical assembly 130 can collect image data while surrounded by a portion of a shaft of a delivery catheter 50 (e.g. when within a transparent segment 57 of a delivery catheter) and/or when there is no catheter 50 segment surrounding optical assembly 130 (e.g. when optical assembly 130 has been advanced beyond the distal ends 59 of all delivery catheters 50 into which probe 100 is inserted.

During collection of image data, a flushing procedure can be performed, such as by delivering one or more fluids, injectate 305 (e.g. as propelled by injector 300 or other fluid delivery device), to remove blood or other somewhat opaque material (hereinafter non-transparent material) proximate optical assembly 130 (e.g. to remove non-transparent material between optical assembly 130 and a delivery catheter and/or non-transparent material between optical assembly 130 and a vessel wall), such as to allow light distributed from optical assembly 130 to reach and reflectively return from all tissue and other objects to be imaged. In these flushing embodiments, injectate 305 can comprise an optically transparent material, such as saline. Injectate 305 can comprise one or more visualizable materials, as described herebelow. Injectate 305 can be delivered by injector 300 as described hereabove.

Alternative or in addition to its use in a flushing procedure, injectate 305 can comprise material configured to be viewed by second imaging device 92, such as when injectate 305 comprises a contrast material configured to be viewed by a second imaging device 92 comprising a fluoroscope or other X-ray device; an ultrasonically reflective material configured to be viewed by a second imaging device 92 comprising an ultrasound imager; and/or a magnetic material configured to be viewed by a second imaging device 92 comprising an MRI.

Injectate 305 can be delivered by one or more delivery catheters 50 (e.g. in the space between a first delivery catheter 50 and an inserted delivery catheter 50, or in the space between a delivery catheter 50 and an inserted probe 100). Injectate 305 delivered in a flushing procedure (or other injectate 305 delivery procedure) can be delivered out the distal end 59 of a delivery catheter 50 (e.g. a distal end 59 positioned proximal to optical assembly 130), as described herebelow in reference to FIG. 5, 6A-E, 7A-E, 8A-D, 9A-C or 10A-E. Alternatively or additionally, any delivery catheter 50 can comprise one or more sideholes passing through a portion of the associated shaft 51, such as sideholes 58 shown positioned on a distal portion of delivery catheter 50c. In some embodiments, a delivery catheter 50 comprises a microcatheter comprising sideholes 58 positioned in a distal portion, such as a microcatheter with an ID less than 0.027" (e.g. a microcatheter with an ID between 0.016" and 0.027" or an ID between 0.021" and 0.027"). In some embodiments, flushing fluid is delivered towards optical assembly 130 from both sideholes 58 and from the distal end 59 of a delivery catheter 50 as described herebelow in reference to FIG. 12. Sideholes 58 can be constructed and arranged to allow a flushing fluid to pass from within shaft 51 and through the sideholes 58, such as when a separate shaft is inserted within the delivery catheter 50 (e.g. a shaft 51 of an additional delivery catheter 50 or the shaft 110 of probe 100). Delivery of flushing fluid through sideholes 58 and/or the distal end of the delivery catheter 50 can be performed to clear blood from an area from a luminal segment surrounding optical assembly 130, such as during collecting of image data.

In some embodiments, the delivery of injectate 305 during a flushing procedure is based on a parameter selected from the group consisting of: a pre-determined volume of injectate to be delivered; a pre-determined time during which injectate is delivered; an amount of time of delivery including a time extending from a time prior to retraction of shaft 110 that continued until the collecting of the image data has been completed (e.g. completion of retraction of shaft 110); and combinations of one or more of these. In some embodiments, injector 300 delivers fluid in a flushing procedure with an approximate flow profile selected from the group consisting of: contrast (e.g. between 20% and 100% contrast that can be mixed with saline) at 5 ml/second for 6 seconds (e.g. for imaging of a carotid artery including 4 seconds of collecting image data); contrast (e.g. between 20% and 100% contrast that can be mixed with saline) at 4 ml/second for 6 seconds (e.g. for imaging of a vertebral artery including 4 seconds of collecting image data); and combinations of one or more of these. In some embodiments, a flushing procedure comprises delivery of injectate 305 (e.g. via one or more delivery catheters 50) for between 2 seconds to 8 seconds, such as a delivery of injectate for approximately 4 seconds (e.g. to purge blood or other non-transparent fluid from a luminal segment of a blood vessel or other area surrounding optical assembly 130 during collection of image data from a patient site PS). In similar flushing procedures, injectate 305 is delivered at a rate between 3 ml/second and 6 ml/second (e.g. via one or more delivery catheters 50), to purge non-transparent material.

In these flushing procedures, injectate 305 can comprise a transparent fluid selected from the group consisting of: saline; contrast; Dextran; and combinations of one or more of these. In some embodiments, the volume of injectate 305 delivered and/or the time of injectate 305 delivery during a flushing procedure is determined by a parameter selected from the group consisting of: type of procedure being performed; diameter of vessel in which optical assembly 130 is positioned; length of pullback; duration of pullback; and combinations of one or more of these. In some embodiments, injectate 305 is delivered during a flushing procedure by a delivery catheter with an ID greater than 0.027" (e.g. a first delivery catheter 50 whose distal end 59 is more proximal than a second delivery catheter 50 inserted into the first delivery catheter 50). In some embodiments, injectate 305 is delivered via multiple lumens 52 in associated multiple delivery catheters 50 (e.g. in the space between two or more pairs of delivery catheters 50 arranged columinally).

In some embodiments, injectate 305 comprises a first fluid delivered in a first portion of a flushing procedure (e.g. a fluid comprising saline and/or a fluid comprising no or minimal contrast), and a second fluid including contrast (e.g. a second fluid comprising saline and contrast), such as to limit the amount of contrast delivered to the patient during the flush procedure. In these embodiments, injector 300 can comprise two reservoirs (as described hereabove), such as a first reservoir for supplying the first fluid and a second reservoir for supplying the second fluid. When comprised of two reservoirs, injector 300 can be configured to deliver the fluids in each reservoir at different rates, such as to achieve different pressures and/or to provide flushing through different catheters with different IDs.

As described herein, optical assembly 130 can be rotated (e.g. via rotation of core 120) and retracted (e.g. via retraction of shaft 110 by retraction assembly 220) during collection of image data, such as a rotation combined with retraction to create a 3D image of the patient site PS. In some embodiments, optical assembly 130 is rotated at a rate between 40 rps and 1000 rps, such as a rate of approximately 250 rps. In some embodiments, optical assembly 130 is rotated at a first rate during an imaging mode, and a second rate during a preview mode (imaging mode and preview mode each described hereabove). In some embodiments, the retraction of optical assembly 130 spans a distance of between 1 cm and 15 cm, such as a retraction of approximately 4 cm. In some embodiments, optical assembly 130 is retracted at a rate of between 1 mm/sec and 60 mm/sec. In some embodiments, the retraction of optical assembly 130 comprises a retraction of approximately 7.5 cm over 4 seconds and/or a retraction rate of approximately 20 mm/sec. In some embodiments, retraction of optical assembly 130 comprises a resolution of between 5 µm and 20 µm axially and/or a resolution between 20 µm and 100 µm longitudinally. The longitudinal resolution is governed by two factors: the spot-size (light beam cross-section) at the tissue surface being imaged and the spacing between successive rotations of optical assembly 130 during retraction. For a rotation rate of 100 rps and a pullback rate of 22 mm/sec, a pitch of 220 µm between rotations results. In these configurations, a spot size between 20 µm and 40 µm would result in collecting image data which under-samples the objects being imaged. System 10 can be configured to more closely match spot size with pitch, such as by correlating spot size with rotation rate and/or pullback rate.

Figure 14:
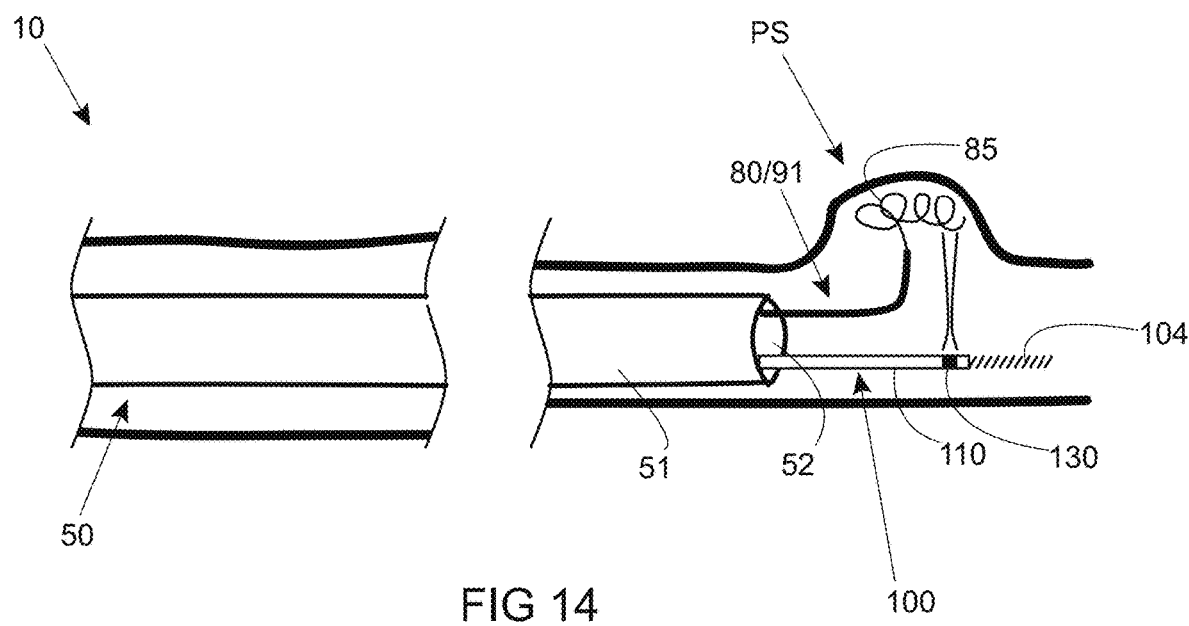
FIG. 14 is a schematic anatomical view of an imaging probe in a side-by-side configuration with a second device, consistent with the present inventive concepts.
Figure 15:
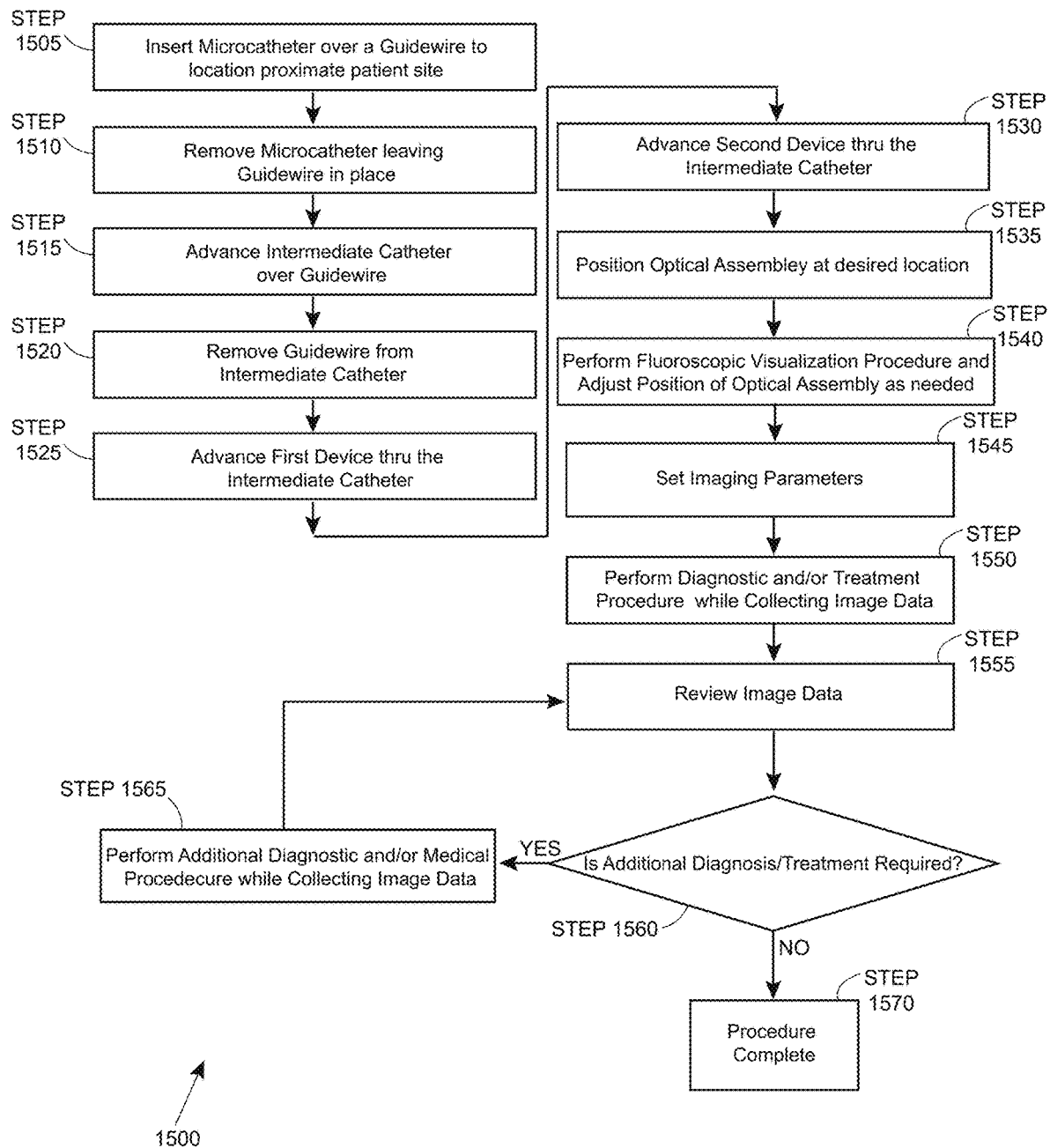
FIG. 15 is a flow chart of a method of creating an image using an imaging probe in a side-by-side configuration with a second device, consistent with the present inventive concepts.

In some embodiments, imaging probe 100 and a second device (e.g. a diagnostic and/or treatment device), such as implant delivery device 80 or treatment device 91 are positioned in a side-by-side configuration within a single delivery catheter 50, as described herebelow in reference to FIG. 14 and/or FIG. 15.

Figure 2:
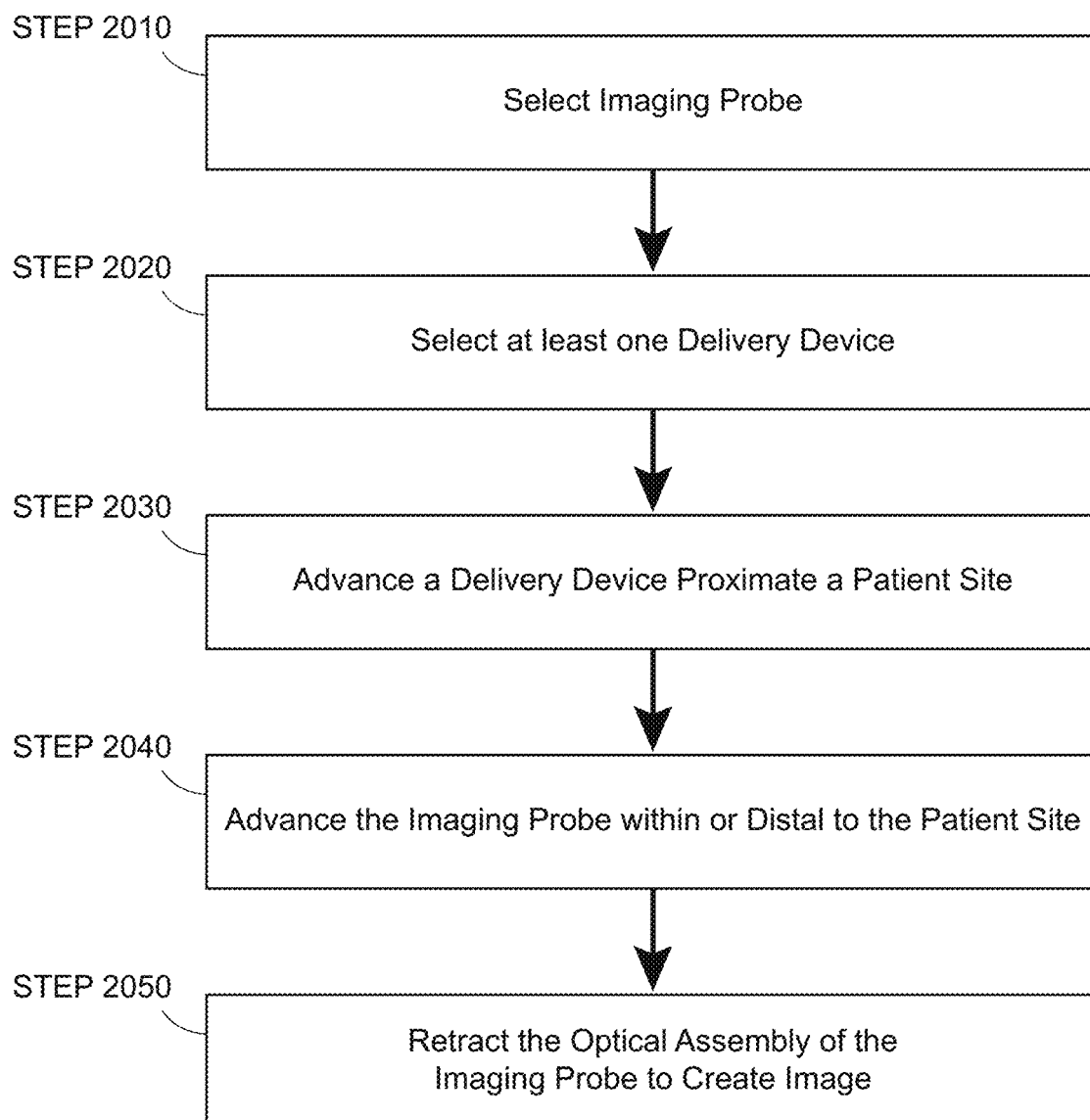
FIG. 2 is a flow chart of a method of creating an image, consistent with the present inventive concepts.

Referring now to FIG. 2, a flow chart of a method of creating an image is illustrated, consistent with the present inventive concepts. The method of FIG. 2 will be described using the devices and components of system 10 described hereabove in reference to FIG. 1. In Step 2010, an imaging probe 100 is selected for use. In some embodiments, the imaging probe is of similar construction and arrangement to the similar components described in applicant's U.S. Provisional Application Ser. No. 62/148,355, titled "Micro-Optic Probes for Neurology", filed Apr. 29, 2015, the content of which is incorporated herein in its entirety. In Step 2020, at least one delivery device is selected, such as the selection of one or more guidewires 60 and/or delivery catheters 50 described herein.

In Step 2030, a delivery catheter 50 is advanced to a location proximate a patient site PS, such as a neural site or a cardiac site. Step 2030 can involve the advancement of multiple guidewires 60 and/or delivery catheters 50 each of which are advanced and/or retracted in sequential steps such that a most distal guidewire 60 and/or delivery catheter 50 eventually provides access to a patient site PS to be imaged (e.g. an intracranial location proximate the patient's brain), from a remote or otherwise different location, such as from the patient's leg (e.g. via a femoral artery), arm (e.g. via the brachial artery or radial artery), or neck (e.g. via a carotid artery). In some embodiments, an anti-coagulation procedure (e.g. the systemic delivery of a blood thinner such as heparin) is performed prior to inserting one or more delivery catheters 50. In some embodiments, one or more guidewires 60, one or more delivery catheters 50 and/or probe 100 is advanced through one or more veins of the patient. In some embodiments, one or more guidewires 60, one or more delivery catheters 50 and/or probe 100 is advanced through the spine of the patient (e.g. within the epidural space or intrathecal space of the spine). In some embodiments, one or more delivery devices (e.g. one or more guidewires 60 and/or delivery catheters 50) are advanced to a location within a patient site PS as described herebelow in reference to FIG. 5, 6A-E, 7A-E, 8A-D, 9A-C, 10A-E or 12.

In Step 2040, probe 100 is advanced over a guidewire 60 and/or through a delivery catheter 50 to the patient site PS (e.g. through the smallest diameter delivery catheter 50 of a series of delivery catheters 50 used to access the patient site PS as described herein).

In Step 2050, shaft 110 of probe 100 is retracted and image data is collected during the retraction (e.g. image data used to create a three dimensional image of tissue proximate the patient site PS). In some embodiments, optical assembly 130 is positioned (in Step 2040) distal to the distal end of a delivery catheter 50, and image data is collected while optical assembly 130 remains distal to the distal end of the delivery catheter 50 (e.g. as described herebelow in reference to FIG. 3). In other embodiments, optical assembly 130 is positioned (in Step 2040) proximal to the distal end of a delivery catheter 50, and image data is collected through the shaft 51 of the delivery catheter 50 by optical assembly 130 (as described herebelow in reference to FIG. 4A or 4B). In some embodiments, a guidewire 60 is inserted (e.g. reinserted) into a delivery catheter 50 after probe 100 is removed from the delivery catheter 50 (e.g. after image data is collected by system 10 during a retraction of optical assembly 130 of imaging probe 100). In these embodiments, probe 100 can be subsequently reinserted into the delivery catheter 50 (e.g. after the guidewire 60 is removed and/or to collect additional image data).

In some embodiments, a first delivery catheter $50_{INTRO}$ comprises a vascular introducer (e.g. a 7 Fr to 9 Fr introducer) which can be placed through the patient's skin into a blood vessel (e.g. a vein or artery of the leg, arm or neck as described herein) or other anatomical location using standard percutaneous techniques. A second delivery catheter $50_{GUIDE}$ (e.g. a guide catheter or a catheter with an OD between 5 Fr and 7 Fr) can be inserted through delivery catheter $50_{INTRO}$, and advanced to a first anatomical location such as a location over the aortic arch. Delivery catheter $50_{GUIDE}$ can be advanced to the first anatomical location over a guidewire $60_L$, such as a hydrophilic guidewire comprising an OD between 0.035" and 0.038". Delivery catheter $50_{GUIDE}$ can comprise a straight tip or angled tip guide catheter. In some embodiments, prior to advancement of delivery catheter $50_{GUIDE}$, a separate delivery catheter $50_{DIAG}$ is inserted through delivery catheter $50_{INTRO}$, such as to effectively direct guidewire $60_L$ into one or more blood vessels (e.g. when delivery catheter $50_{GUIDE}$ comprises a straight tip guide catheter). In these embodiments, after the guidewire $60_L$ is advanced into the desired blood vessel, the delivery catheter $50_{DIAG}$ can be removed and replaced with delivery catheter $50_{GUIDE}$.

After delivery catheter $50_{GUIDE}$ is in place, probe 100 can be inserted through delivery catheter $50_{GUIDE}$ and advanced to a patient site PS to be imaged (e.g. advanced over guidewire $60_L$, advanced over a smaller or other different guidewire 60 after guidewire $60_L$ is removed, or advanced without a guidewire after guidewire $60_L$ is removed). Subsequently, imaging data can be obtained by rotating and/or retracting optical assembly 130 as described herein. Alternative to inserting probe 100 at this time, a smaller delivery catheter 50 can be inserted into and through delivery catheter $50_{GUIDE}$, such as a delivery catheter $50_{INTER}$ comprising an intermediate catheter and/or a catheter with an ID between 0.053" and 0.070". Delivery catheter $50_{INTER}$ can be advanced to a location more distal than the distal end 59 of delivery catheter $50_{GUIDE}$. In some embodiments, guidewire $60_L$ is replaced with a different guidewire 60, such as a replacement with a smaller guidewire $60_S$ (e.g. comprising an OD between 0.010" and 0.014").

After delivery catheter $50_{INTER}$ is in place, probe 100 can be inserted through delivery catheter $50_{INTER}$ and advanced to a patient site PS to be imaged (e.g. advanced over guidewire $60_L$, advanced over a smaller or other different guidewire 60 after guidewire $60_L$ is removed, or advanced without a guidewire after guidewire $60_L$ is removed). Subsequently, imaging data can be obtained by rotating and/or retracting optical assembly 130 as described herein. Alternatively to inserting probe 100 at this time, a smaller delivery catheter 50 can be inserted into and through delivery catheter $50_{INTER}$, such as a delivery catheter $50_{MICRO}$ comprising a microcatheter and/or a catheter with an ID between 0.0165" and 0.027". Delivery catheter $50_{MICRO}$ can be advanced to a location more distal than the distal end 59 of delivery catheter $50_{INTER}$. In some embodiments, guidewire $60_L$ is removed from delivery catheter $50_{INTER}$, and replaced with a smaller guidewire $60_S$, over which delivery catheter $50_{MICRO}$ is advanced. Guidewire $60_S$ can comprise a guidewire with an OD between 0.010" and 0.014".

After delivery catheter $50_{MICRO}$ is in place, probe 100 can be inserted through delivery catheter $50_{MICRO}$ and advanced to a patient site PS to be imaged (e.g. advanced over guidewire $60_L$ or $60_S$, advanced over a smaller or other different guidewire 60 after guidewire $60_L$ or $60_S$ is removed, or advanced without a guidewire after guidewire $60_L$ or $60_S$ is removed). Subsequently, imaging data can be obtained by rotating and/or retracting optical assembly 130 as described herein. Alternatively to inserting probe 100 at this time, delivery catheter $50_{INTER}$ can be advanced over delivery catheter $50_{MICRO}$ (e.g. while a guidewire 60 is within delivery catheter $50_{MICRO}$), delivery catheter $50_{MICRO}$ and any inserted guidewires 60 removed, and probe 100 inserted into delivery catheter $50_{INTER}$, as described herebelow in reference to FIG. 10. Subsequently, imaging data can be obtained by rotating and/or retracting optical assembly 130 as described herein.

Figure 3:
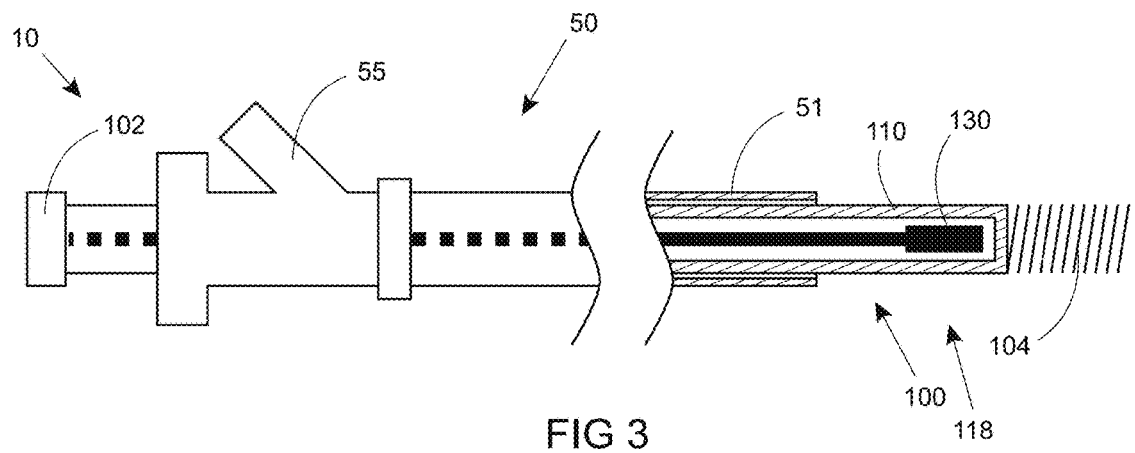
FIG. 3 is a side, partial sectional view of a system comprising an imaging probe and a delivery catheter, wherein the imaging probe comprises an optical assembly configured to collect image data while positioned outside the delivery catheter, consistent with the present inventive concepts.

Referring now to FIG. 3, a side, partial sectional view of a system comprising an imaging probe and a delivery catheter is illustrated, wherein the imaging probe comprises an optical assembly configured to collect image data while positioned outside the delivery catheter, consistent with the present inventive concepts. System 10 comprises probe 100 and at least one delivery catheter 50, each of which can be of similar construction and arrangement to the similar components described hereabove in reference to FIG. 1. Probe 100 can comprise proximal connector 102 and spring tip 104 as described herein. Imaging probe 100 and delivery catheter 50 are constructed and arranged such that optical assembly 130 can be positioned distal to the distal end of shaft 51 of delivery catheter 50. For example, probe 100 can comprise a longer length (e.g. a longer shaft 110 length) than the length of delivery catheter 50, such as when probe 100 comprises a length at least 1 cm longer than the length of delivery catheter 50, such as a length at least 2 cm, 3 cm, 4 cm, or 5 cm longer. In some embodiments, shaft 110 of probe 100 comprises an insertable length of up to 200 cm, and a non-insertable length (i.e. the proximal portion of shaft 110) of approximately 7 cm. In some embodiments, at least the distal portion 118 of shaft 110 comprises an OD of approximately 0.014", such as when delivery catheter 50 comprises an ID of approximately 0.0165" (e.g. with an OD of approximately 0.022"). In some embodiments, at least the distal portion 118 of shaft 110 comprises an OD between 0.014" and 0.016", such as when delivery catheter 50 comprises an OD of no more than 0.032". In some embodiments, probe 100 comprises a length of up to 200 cm, such as when delivery catheter 50 comprises a length at least 2 cm shorter than the length of probe 100. Probe 100 can be retracted during collection of image data, such as a retraction of shaft 110 of probe 100 of at least 1 cm, such as a retraction of at least 2 cm, 3 cm, 4 cm, 5 cm, 8 cm or 10 cm. System 10 can comprise one or more delivery catheters 50, wherein delivery catheter 50 shown is the smallest diameter of a set of delivery catheters 50 currently positioned within the patient, and into which probe 100 has been inserted.

Figure 4A:
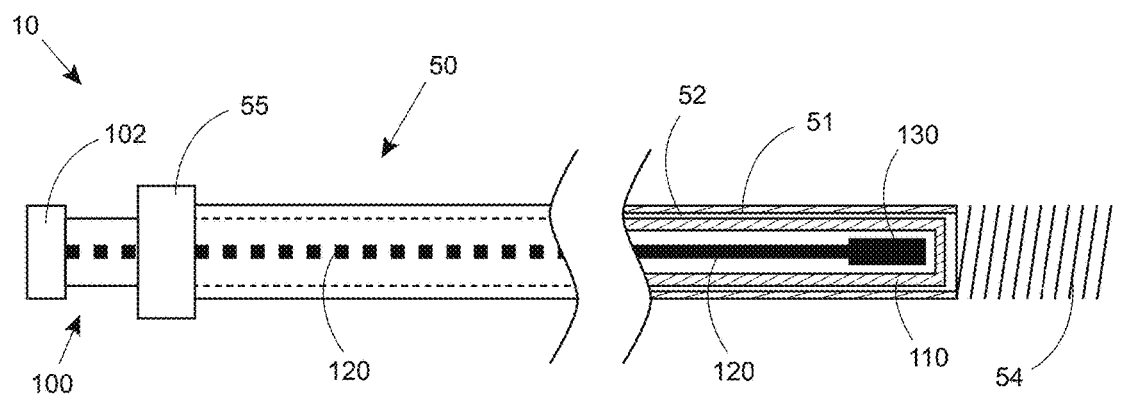
FIGS. 4A and 4B are side, partial sectional views of two configurations of a system comprising an imaging probe and a delivery catheter, wherein the imaging probe comprises an optical assembly configured to collect image data while positioned within the distal portion of the delivery catheter, consistent with the present inventive concepts.
Figure 4B:
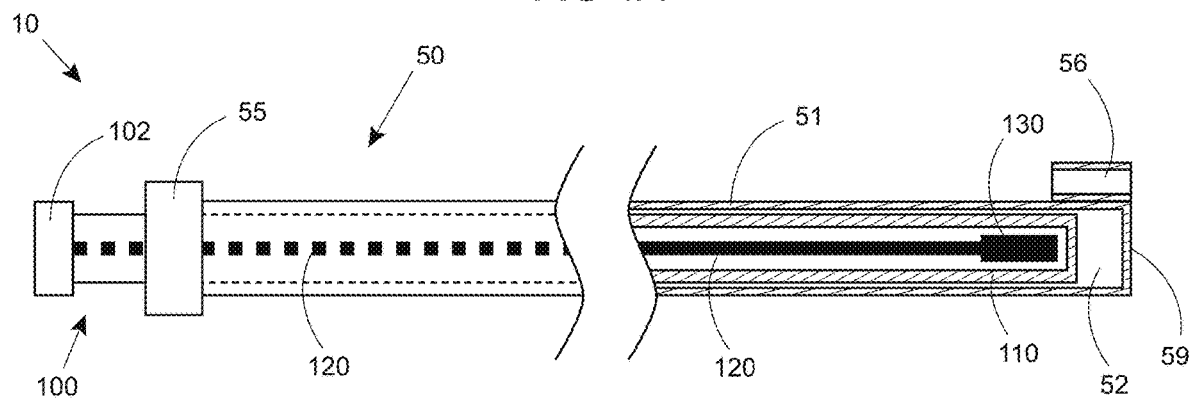

Referring now to FIGS. 4A and 4B, side, partial sectional views of two configurations of a system comprising an imaging probe and a delivery catheter are illustrated, wherein the imaging probe comprises an optical assembly configured to collect image data while positioned within the distal portion of the delivery catheter, consistent with the present inventive concepts. System 10 comprises probe 100 and delivery catheter 50, each of which can be of similar construction and arrangement to the similar components described hereabove in reference to FIG. 1. Imaging probe 100 and delivery catheter 50 are constructed and arranged such that optical assembly 130 can be positioned within a distal portion of shaft 51 of delivery catheter 50. For example, delivery catheter 50 can comprise a closed end (as shown in FIG. 4B) and/or optical assembly 130 can otherwise be positioned within the distal portion of delivery catheter 50 during its retraction to collect image data. In some embodiments, delivery catheter 50 is first inserted into the patient over a guidewire 60 (e.g. and also through one or more separate, larger diameter delivery catheters 50 as described herein but not shown), after which imaging probe 100 is inserted into delivery catheter 50 to the position shown in FIG. 4A or 4B. In other embodiments, delivery catheter 50 and imaging probe 100 are inserted into the patient simultaneously (e.g. in unison through a second, larger diameter delivery catheter 50 from which a guidewire 60 has been removed). In these embodiments, imaging probe 100 and delivery catheter 50 can be frictionally engaged with each other, such as to maintain a relative position between the shafts of the two devices. Imaging probe 100 can be constructed and arranged to be disengaged and slidingly removed from delivery catheter 50. System 10 can comprise one or more delivery catheters 50, wherein delivery catheter 50 shown is the smallest diameter of a set of delivery catheters 50 currently positioned within the patient, and into which probe 100 has been inserted.

In some embodiments, delivery catheter 50 comprises a lumen with a closed end (also known as a "blind lumen"), such as is lumen 52 shown in FIG. 4B. In some embodiments, delivery catheter 50 is constructed and arranged to be advanced over a guidewire (e.g. guidewire 60 described herein) in a rapid exchange fashion, such as via a rapid exchange lumen, sidecar 56, shown in FIG. 4B. Delivery catheter 50 can comprise a transparent portion 57, not shown, but as described hereabove.

Figure 5:
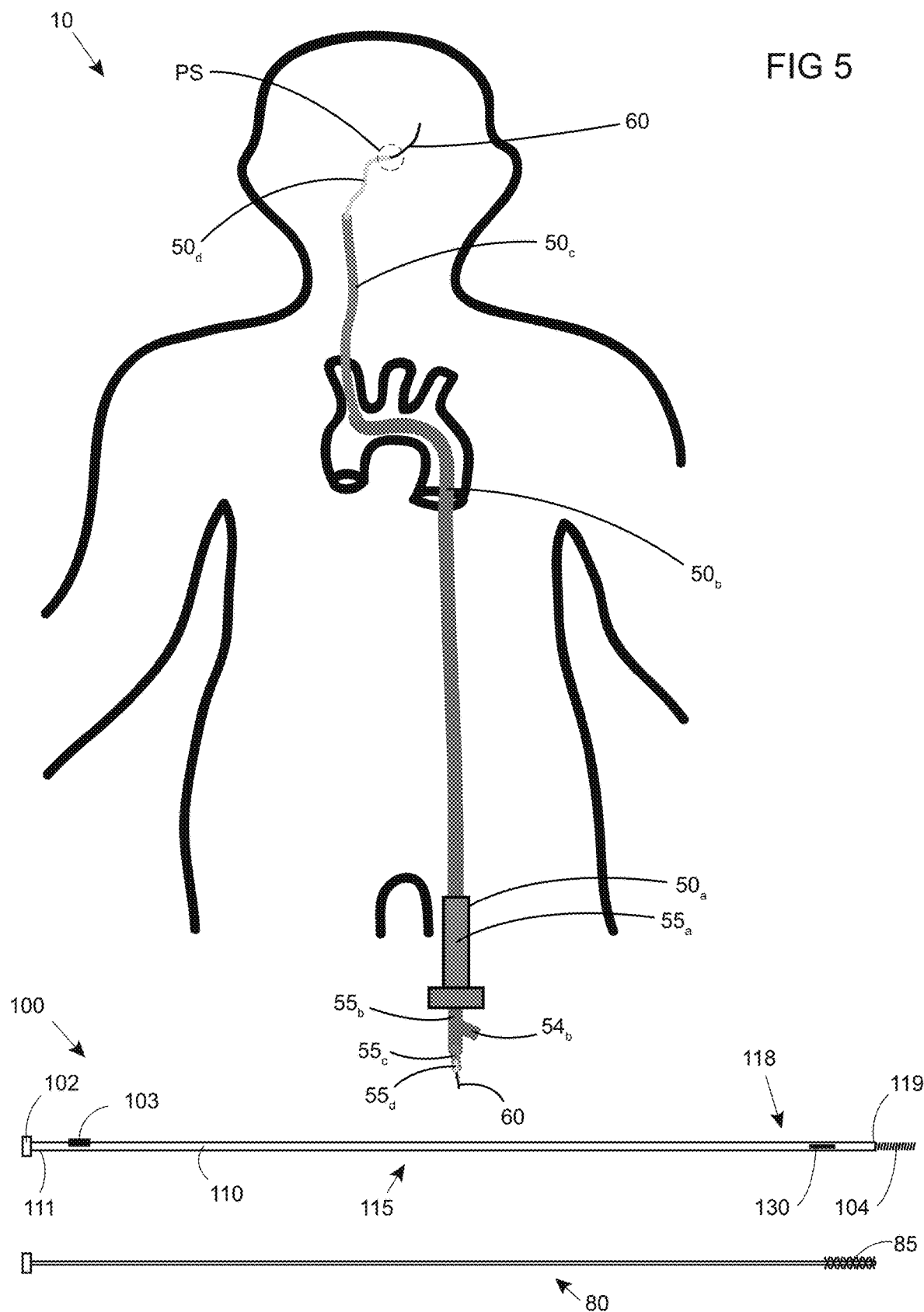
FIG. 5 is an anatomical view of system percutaneously inserted into a patient, consistent with the present inventive concepts.

Referring now to FIG. 5, an anatomical view of an imaging system comprising multiple devices that have been percutaneously inserted into a patient is illustrated, consistent with the present inventive concepts. System 10 comprises probe 100, and a kit of delivery devices including multiple delivery catheters 50, and one or more guidewires 60. In some embodiments, system 10 comprises one or more similar components to system 10 described hereabove in reference to FIG. 1. Delivery catheters 50 comprise one or more delivery catheters, such as introducer 50a, a first delivery catheter 50b (e.g. a guide catheter as described herein), a second delivery catheter 50c (e.g. an intermediate catheter as described herein), and/or a third delivery catheter 50d (e.g. a microcatheter as described herein), each shown in FIG. 5. Delivery catheter 50a has been introduced into a blood vessel of the patient, such as a femoral artery, brachial artery, radial artery, carotid artery or a vein of the patient, such as by using standard percutaneous techniques to place an elongate device through the patient's skin and into a blood vessel. Guidewire 60 (e.g. a guidewire with an OD between 0.035" and 0.038") is positioned such that additional delivery catheters can be delivered using an over-the-wire advancement through one or more blood vessels. Delivery catheter 50b has been inserted into and through delivery catheter 50a (e.g. over guidewire 60), such that its distal end is positioned at a location just distal to or otherwise proximate the aortic arch, such as at a location proximate the intracranial artery (ICA) or vertebral artery. Subsequently, delivery catheter 50c has been inserted into and through delivery catheter 50b (e.g. over guidewire 60), such that its distal end is advanced to an intravascular location as far distal as the middle cerebral artery (MCA). In some embodiments, the distal end of delivery catheter 50c is positioned within or at least proximate a location selected from the group consisting of: internal ceratoid artery; intracranial internal carotid artery (from the cervical ICA); petrous ICA; proximal cavernous ICA; distal cavernous/clinoidal ICA; supraclinoid ICA; the M1 segment V3-4 junction of the vertebral artery; distal V4; proximal basilar; proximal-mid basilar; mid-basilar; and combinations of one or more of these. In some embodiments, guidewire 60 is replaced with a smaller guidewire 60 (e.g. a guidewire with an OD of between 0.010" and 0.014" as described herein). Subsequently, delivery catheter 50d has been inserted into and through second delivery catheter 50c (e.g. over guidewire 60), such that its distal end is positioned at a location proximate (e.g. just distal to, within and/or just proximal to) a patient site PS, comprising a neural site, as defined hereabove, or a cardiac site.

As described herein, guidewire 60 can comprise multiple guidewires, such as multiple guidewires with different lengths, diameters and/or stiffnesses, such as when a subsequent delivery catheter 50 is advanced over a more flexible guidewire 60 than a previous delivery catheter 50 (e.g. more flexible guidewires 60 are used to advance smaller delivery catheters 50 to a more distal location). In some embodiments, one or more of delivery catheters 50a-d comprise a Tuohy valve of a connector 55a-d, respectively, on their proximal end, such as to reduce blood leakage from the proximal end of the associated delivery catheter 50. In some embodiments, one or more delivery catheters 50 comprise a port 54 (e.g. port 54b shown on the proximal end of delivery catheter 50b), such as to connect to a source of contrast, flushing and/or other fluids to be delivered via a lumen 52 (not shown) of the associated delivery catheter 50.

The distal end 119 of shaft 110 is advanced to be proximate the distal end of delivery catheter 50d. In some embodiments, image data is collected while retracting shaft 110 while optical assembly 130 remains within the shaft of delivery catheter 50d (such as is described herebelow in reference to FIGS. 8A-8E). In these embodiments, the distal portion of the shaft of delivery catheter 50d can comprise a transparent segment, transparent segment 57 (not shown) as described herein, such that optical assembly 130 remains within the transparent segment 57 while collecting image data. In other embodiments, delivery catheter 50d is retracted, and optical assembly 130 is outside of the shaft of delivery catheter 50d while collecting image data (e.g. during retraction of shaft 110 such as is described herebelow in reference to FIGS. 7A-E). In yet other embodiments, probe 100 is advanced such that optical assembly 130 is positioned distal to the distal end of delivery catheter 50d, and similarly, optical assembly 130 is outside of the shaft of delivery catheter 50d while collecting image data (e.g. during retraction of shaft 110 such as is described herebelow in reference to FIGS. 6A-D).

A flushing procedure (e.g. as described herein) can be performed through any delivery catheter 50, prior to and/or during the collecting of image data by optical assembly 130. In some embodiments, pullback of shaft 110 is initiated when adequate clearing is confirmed, such as by analysis of image data collected by optical assembly 130 (e.g. an operator analysis of an image or an automated analysis performed by algorithm 240).

In some embodiments, system 10 comprises probe 100 and one or more delivery devices and/or implants configured to treat a disease or disorder such as stroke and/or to remove thrombus from a blood vessel. In these embodiments, system 10 can comprise probe 100 and one or more components selected from the group consisting of: a delivery catheter 50 comprising a balloon guide catheter of approximately between 8 Fr or 9 Fr; a treatment device 91 (described hereabove in reference to FIG. 1) comprising a thrombus extraction device such as the Penumbra 5 MaxAce (or similar); a delivery catheter 50 comprising a distal portion with an OD of approximately 5 Fr, an ID of approximately 0.054" and/or a length of approximately 132 cm, and/or a Covidien Solitaire FR Retriever (or similar); a delivery catheter 50 configured to deliver a treatment device 91 comprising a thrombus extraction device, such as a catheter with an ID between approximately 0.021" and 0.027"; a guidewire such a Stryker Synchro guidewire; and combinations of one or more of these. In some stroke treatment or other thrombus removal applications, system 10 comprises probe 100 and one or more components selected from the group consisting of: a delivery catheter 50 comprising a balloon guide catheter of approximately between 8 Fr and 9 Fr (e.g. a delivery catheter 50 advanced into a proximal vessel such as the proximal internal carotid artery or subclavian artery just proximal to the vertebral artery take-off, which is inflated to prevent antegrade flow); a delivery catheter 50 such as a Stryker Merci Balloon Guide Catheter of approximately 9 Fr; a Stryker Flowgate balloon guide catheter of approximately 8 Fr; a treatment device 91 comprising a Penumbra ACE 64 device or similar; a delivery catheter 50 comprising a Covidien Marksman microcatheter with a diameter (e.g. an OD) of approximately 0.027" or similar; a treatment device 91 comprising a Covidien Solitaire FR retriever device or similar; and combinations of one or more of these. In some embodiments, system 10 includes both a treatment device 91 comprising a thrombus removal device (e.g. the Penumbra ACE 64 device or similar thrombus removal device) and a delivery catheter 50 configured to remove thrombus. In these embodiments, the treatment device 91 comprising the thrombus removal device is used first, and the delivery catheter 50 is used to remove thrombus if the treatment device 91 is unsuccessful at removing sufficient thrombus. In some stroke treatment or other thrombus removal applications including deployment of a thrombus removal device (e.g. a Penumbra ACE™ or other stent retriever), system 10 comprises probe 100 and one or more components selected from the group consisting of: a first delivery catheter 50 comprising an introducer with an ID between 7 Fr and 9 Fr; a second delivery catheter 50 comprising a guide catheter configured to be slidingly received by the first delivery catheter 50 and comprising an ID between 5 Fr and 7 Fr, an ID of approximately 0.088", a length of between 80 cm and 90 cm and/or a distal end configured to be positioned proximate the aortic arch; a third delivery catheter 50 comprising a reperfusion catheter configured to be slidingly received by the second delivery catheter and comprising an OD between 3.8 Fr and 5.4 Fr and/or a length between 132 cm and 153 cm; a fourth delivery catheter 50 comprising a microcatheter configured to be slidingly received by the third delivery catheter 50 and comprising an OD of approximately 2.6 Fr and/or a length of approximately 160 cm; an injector 300 comprising a power injector; a treatment device comprising a stent retriever or other thrombus removal device; a Penumbra ACE™ stent retriever; and combinations of one or more of these.

In some embodiments, system 10 comprises probe 100 and one or more delivery devices and/or implants configured to treat a disease or disorder such as an aneurysm. In these embodiments, system 10 can be configured to treat the aneurysm by delivering coils, such as when system 10 comprises probe 100 and one or more components selected from the group consisting of: a delivery catheter 50 comprising an approximately 6 Fr guide catheter such as a 6 Fr Cordis Envoy catheter (or similar) and/or a 6 Fr Penumbra Neuron catheter (or similar); a delivery catheter 50 comprising a Stryker SL-10 catheter (or similar); an implant 85 comprising one or more embolization coils such as one or more Target embolization coils (or similar); an implant delivery device such as a catheter configured to deliver one or more embolization coils; and combinations of one or more of these. In some aneurysm treatment applications including delivery of coils, system 10 comprises probe 100 and one or more components selected from the group consisting of: a delivery catheter 50 comprising an approximately 6 Fr guide catheter such as a 6 Fr Cordis Envoy™ catheter and/or a 6 Fr Penumbra Benchmark™ catheter; a delivery catheter 50 comprising a Stryker SL-10™ catheter (or similar); a delivery catheter 50 comprising a Covidien Echelon™ Catheter (e.g. Echelon 14, Echelon 10, or similar), such as a catheter with a length of approximately 150 cm with a 0°, 45° or 90° tip angle; a guidewire 60 comprising a Covidien X-Celerator™ hydrophilic guidewire, a Covidien X-Pedion™ guidewire and/or a Stryker Synchro™ guidewire; one or more embolization coils; and combinations of one or more of these. In some aneurysm treatment applications including delivery of coils, system 10 comprises probe 100 and one or more components selected from the group consisting of: a first delivery catheter 50 comprising an introducer with an ID between 7 Fr and 9 Fr; a second delivery catheter 50 comprising a guide catheter configured to be slidingly received by the first delivery catheter and comprising an ID between 5 Fr and 7 Fr, a Touhy valve and/or a length of approximately 90 cm; a third delivery catheter 50 comprising an intermediate catheter configured to be slidingly received by the second delivery catheter 50 and comprising an OD less than 7 Fr and/or a length of approximately 115 cm; a fourth delivery catheter 50 comprising a microcatheter configured to be slidingly received by the third delivery catheter 50 and comprising an ID of approximately 0.0165" and/or a length of approximately 150 cm; a first guidewire 60 configured to be slidingly received by the first delivery catheter 50, the second delivery catheter 50, the third delivery catheter 50 and/or the fourth delivery catheter 50 and comprising a diameter (e.g. an OD) of approximately 0.014" and/or a length between 175 cm and 190 cm; injector 300 comprising a power injector; treatment device 91 comprising a coil deployment catheter; one or more coils; and combinations thereof.

Alternatively or additionally, system 10 can be configured to treat an aneurysm by implanting a flow diverter, such as when system 10 comprises probe 100 and one or more components selected from the group consisting of: a delivery catheter 50 comprising a guiding catheter such as a guiding catheter with an ID of approximately 6 Fr and/or a length of approximately 110 cm (e.g. configured to be delivered to a location over the aortic arch); a guidewire 60 such as a guidewire with an OD of approximately 0.035"; a Cook Guidewire (or similar); a delivery catheter 50 comprising a catheter with an ID of approximately 0.058", an OD of less than 7 Fr, and/or a length of approximately 115 cm; a delivery catheter 50 with a distal portion with an OD of approximately 2.7 Fr, an ID of approximately 0.027" and/or a length between 135 cm and 150 cm; a flow diverter such as a Covidien EV3 Pipeline™ flow diverter (or similar); a delivery catheter 50 comprising a delivery catheter 50 configured to deliver a flow diverter such as a Covidien Excelsior™ XT-27 catheter (or similar); and combinations of one or more of these. In some aneurysm treatment applications including implantation of a flow diverter, system 10 comprises probe 100 and one or more components selected from the group consisting of: a delivery catheter 50 comprising an approximately 5 Fr or 6 Fr sheath such as a 6 Fr Cool Flexor Shuttle™ guiding catheter (e.g. which can be delivered over the aortic arch); a delivery catheter 50 of approximately 115 cm length and/or 0.058" ID, such as a Covidien EV3™ 5 Fr catheter; a delivery catheter 50 comprising a Covidien Marksman™ 0.027" catheter; an implant 85 comprising a Covidien EV3 Pipeline™ Flow Diverter (e.g. delivered by the Covidien Marksman™ 0.027" catheter); a guidewire 60 comprising a Cook 0.035" guidewire, a Covidien X-Celerator™ hydrophilic guidewire, a Covidien X-Pedion™ guidewire and/or a Stryker Synchro™ guidewire; and combinations of one or more of these. In some aneurysm treatment applications including implantation of a flow diverter (e.g. a Pipeline™ or Pipeline Flex™ flow diverter), system 10 comprises probe 100 and one or more components selected from the group consisting of: a first delivery catheter 50 comprising an introducer with an ID between 7 Fr and 9 Fr; a second delivery catheter 50 comprising a guide catheter configured to be slidingly received by the first delivery catheter 50 and comprising an ID between 5 Fr and 7 Fr, a Touhy valve and/or a length of approximately 90 cm; a third delivery catheter 50 comprising an intermediate catheter configured to be slidingly received by the second delivery catheter 50 and comprising an OD less than 7 Fr and/or a length of approximately 115 cm; a fourth delivery catheter 50 comprising a microcatheter configured to be slidingly received by the third delivery catheter 50 and comprising an ID less than 0.027"; a first guidewire 60 configured to be slidingly received by the first delivery catheter 50, the second delivery catheter 50, the third delivery catheter 50 and/or the fourth delivery catheter 50 and comprising a length of between 175 cm and 190 cm; a second guidewire 60 configured to be slidingly received by the first delivery catheter 50, the second delivery catheter 50, the third delivery catheter 50 and/or the fourth delivery catheter 50 and comprising a length of between 175 cm and 190 cm; injector 300 such as a power injector; a flow diverter such as a Pipeline™ flow diverter or a Pipeline Flex™ flow diverter; and combinations of one or more of these. In some aneurysm treatment applications including implantation of a flow diverter (e.g. a Surpass™ or Surpass Future™ flow diverter), system 10 comprises probe 100 and one or more components selected from the group consisting of: a first delivery catheter 50 comprising an introducer with an ID between 7 Fr and 9 Fr; a second delivery catheter 50 comprising a guide catheter configured to be slidingly received by the first delivery catheter 50 and comprising an ID between 5 Fr and 7 Fr, a Touhy valve and/or a length of approximately 90 cm; a third delivery catheter 50 comprising an intermediate catheter configured to be slidingly received by the second delivery catheter 50 and comprising an OD less than 7 Fr and/or a length of approximately 115 cm; a fourth delivery catheter 50 comprising a microcatheter configured to be slidingly received by the third delivery catheter 50 and comprising a Surpass™ delivery catheter, an OD less than 3.3 Fr or less than 3.7 Fr and/or a length of approximately 135 cm; a first guidewire 60 configured to be slidingly received by the first delivery catheter 50, the second delivery catheter 50, the third delivery catheter 50 and/or the fourth delivery catheter 50 and comprising an exchange length guidewire; injector 300 such as a power injector; a flow diverter such as a Surpass™ flow diverter and/or a Surpass Future™ flow diverter; and combinations of one or more of these.

Alternatively or additionally, system 10 can be configured to treat an aneurysm by delivering stent assisted coils, such as when system 10 comprises probe 100 and one or more components selected from the group consisting of: a delivery catheter 50 comprising an approximately 6 Fr guide catheter such as a 6 Fr Cordis Envoy™ catheter (or similar) and/or a 6 Fr Penumbra Neuron™ catheter (or similar); a delivery catheter 50 comprising a Cordis Prowler Select Plus™ catheter; an implant delivery device 80 and/or implant 85 comprising Cordis Enterprise™ vascular reconstruction device; a delivery catheter 50 comprising a Stryker XT27™ catheter; an implant delivery device 80 and/or implant 85 comprising a Stryker Neuroform EZ™ stent system; an implant 85 comprising one or more stents; an implant 85 comprising one or more embolization coils; and combinations of one or more of these. In some aneurysm treatment applications including delivery of stent assisted coils, system 10 comprises probe 100 and one or more components selected from the group consisting of: a delivery catheter 50 comprising an approximately 6 Fr guide catheter such as a 6 Fr Cordis Envoy™ catheter and/or a 6 Fr Penumbra Neuron™ catheter; a delivery catheter 50 comprising a Cordis Prowler Select™ for Enterprise and/or a Covidien Marksman™ for Neuroform™; an implant 85 and/or delivery device 80 comprising a Stryker Neuroform EZ™ stent system; an implant 85 comprising one or more stents; an implant 85 comprising one or more embolization coils; a guidewire 60 comprising a Covidien X-Celerator™ hydrophilic guidewire, a Covidien X-Pedion™ guidewire and/or a Stryker Synchro™ guidewire; and combinations of one or more of these.

Referring now to FIGS. 6A-E, schematic anatomical views of a series of steps for creating an image are illustrated, including advancing an imaging probe beyond the distal end of a delivery catheter prior to collecting image data, consistent with the present inventive concepts. System 10 includes imaging probe 100 and one or more delivery devices, such as at least one delivery catheter 50 and at least one guidewire 60. In some embodiments, system 10 comprises one or more similar components to system 10 described hereabove in reference to FIG. 1. In some embodiments, system 10 has been introduced into the patient as described hereabove in reference to FIG. 1, 2 or 5, such as when delivery catheter 50 of FIG. 6A comprises one or more delivery catheters 50, such as one or more delivery catheters 50 including at least delivery catheter 50d of FIG. 1 or 5. In FIG. 6A, guidewire 60 has been advanced through a vessel, such as a blood vessel, such that its distal end is at or beyond patient site PS. Delivery catheter 50 has been partially advanced over guidewire 60. While patient site PS of FIGS. 6A-E is shown to include an aneurysm, alternatively or additionally patient site PS can comprise a site of a different patient disease or disorder, a site including an implant such as implant 85, a site including a patient treatment device such as treatment device 91 and/or any internal body location of the patient such as those described herein.

In FIG. 6B, the distal end of delivery catheter 50 has been advanced proximate (e.g. just proximal as shown), patient site PS. In FIG. 6C, guidewire 60 has been removed, and probe 100 has been inserted through delivery catheter 50 such that its distal end, comprising spring tip 104 is proximate the distal end of delivery catheter 50. In FIG. 6D, probe 100 is advanced such that optical assembly 130 is positioned distal to and/or within patient site PS, outside of delivery catheter 50. Subsequently, image data is collected while retracting shaft 110 of probe 100 to the position shown in FIG. 6E. The image data collected comprising image data of the blood, vessel wall and other tissue within patient site PS and/or image data of occlusive matter (e.g. thrombus or plaque) within patient site PS. In some embodiments, the image data further includes image data of an implant (e.g. implant 85 described herein), such as is described herebelow in reference to FIGS. 9A-C, and/or image data of a treatment device such as treatment device 91.

A flushing procedure (e.g. as described herein) can be performed through any delivery catheter 50, during one or more of Steps 6A-E. In some embodiments, a flushing procedure is at least performed during Step 6D, such as via delivery catheter 50 shown, or a more proximal delivery catheter 50 (not shown). In some embodiments, pullback of shaft 110 is initiated when adequate clearing is confirmed by analysis of image data collected by optical assembly 130 (e.g. an operator analysis of an image or an automated analysis performed by algorithm 240).

Referring now to FIGS. 7A-E, schematic anatomical views of a series of steps for creating an image are illustrated, including retracting a delivery catheter to uncover an optical assembly of an imaging probe prior to collecting image data, consistent with the present inventive concepts. System 10 includes imaging probe 100 and one or more delivery devices, such as at least one delivery catheter 50 and at least one guidewire 60. In some embodiments, system 10 comprises one or more similar components to system 10 described hereabove in reference to FIG. 1. In some embodiments, system 10 has been introduced into the patient as described hereabove in reference to FIG. 5, such as when delivery catheter 50 of FIG. 7A comprises one or more delivery catheters 50, such as one or more delivery catheters 50 including at least delivery catheter 50d of FIG. 5. In FIG. 7A, guidewire 60 has been advanced through a vessel, such as a blood vessel, such that its distal end is at or beyond patient site PS. Delivery catheter 50 has been partially advanced over guidewire 60. While patient site PS of FIGS. 7A-E is shown to include an aneurysm, alternatively or additionally patient site PS can comprise a site of a different patient disease or disorder, a site including an implant such as implant 85, a site including a patient treatment device such as treatment device 91 and/or any internal body location of the patient such as those described herein.

In FIG. 7B, the distal end of delivery catheter 50 has been advanced distal to and/or within patient site PS. In FIG. 7C, guidewire 60 has been removed, and probe 100 has been inserted through delivery catheter 50 such that its distal end, comprising spring tip 104 is proximate the distal end of delivery catheter 50. In FIG. 7D, delivery catheter 50 is retracted such that optical assembly 130 is positioned distal to and/or within patient site PS, outside of delivery catheter 50. Subsequently, image data is collected while retracting shaft 110 of probe 100 to the position shown in FIG. 7E. The image data collected comprising image data of the blood, vessel wall and other tissue within patient site PS and/or image data of occlusive matter (e.g. thrombus or plaque) within patient site PS. In some embodiments, the image data further includes image data of an implant (e.g. implant 85 described herein), such as is described herebelow in reference to FIGS. 9A-C, and/or image data of a treatment device such as treatment device 91.

A flushing procedure (e.g. as described herein) can be performed through any delivery catheter 50, during one or more of Steps 7A-E. In some embodiments, a flushing procedure is at least performed during Step 7D, such as via delivery catheter 50 shown, or a more proximal delivery catheter 50 (not shown). In some embodiments, pullback of shaft 110 is initiated when adequate clearing is confirmed by analysis of image data collected by optical assembly 130 (e.g. an operator analysis of an image or an automated analysis performed by algorithm 240).

Figure 8A:
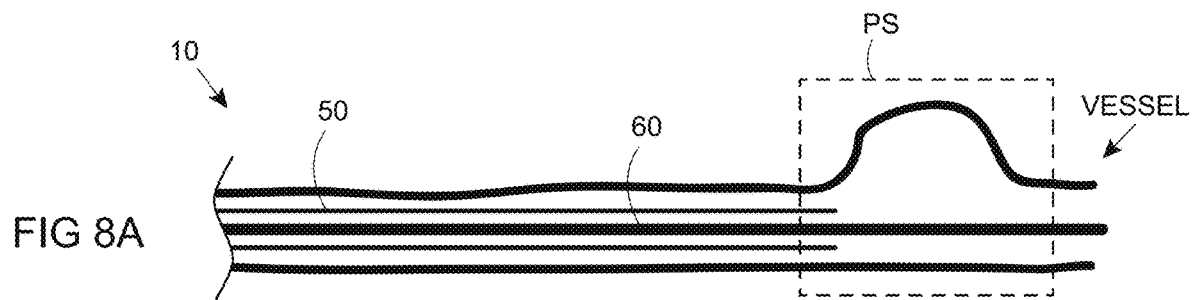
FIGS. 8A-D are schematic anatomical views of a series of steps for creating an image, including collecting image data while the optical assembly of an imaging probe is positioned within a delivery catheter, consistent with the present inventive concepts.

Referring now to FIGS. 8A-D, schematic anatomical views of a series of steps for creating an image are illustrated, including collecting image data while the optical assembly of an imaging probe is positioned within a delivery catheter, consistent with the present inventive concepts. System 10 includes imaging probe 100 and one or more delivery devices, such as at least one delivery catheter 50 and at least one guidewire 60. In some embodiments, system 10 comprises one or more similar components to system 10 described hereabove in reference to FIG. 1. In some embodiments, system 10 has been introduced into the patient as described hereabove in reference to FIG. 5, such as when delivery catheter 50 of FIG. 8A comprises one or more delivery catheters 50, such as one or more delivery catheters 50 including at least delivery catheter 50d of FIG. 5. In FIG. 8A, guidewire 60 has been advanced through a vessel, such as a blood vessel, such that its distal end is at or beyond patient site PS. Delivery catheter 50 has been partially advanced over guidewire 60. While patient site PS of FIGS. 8A-D is shown to include an aneurysm, alternatively or additionally patient site PS can comprise a site of a different patient disease or disorder, a site including an implant such as implant 85, a site including a patient treatment device such as treatment device 91 and/or any internal body location of the patient such as those described herein.

Figure 8B:
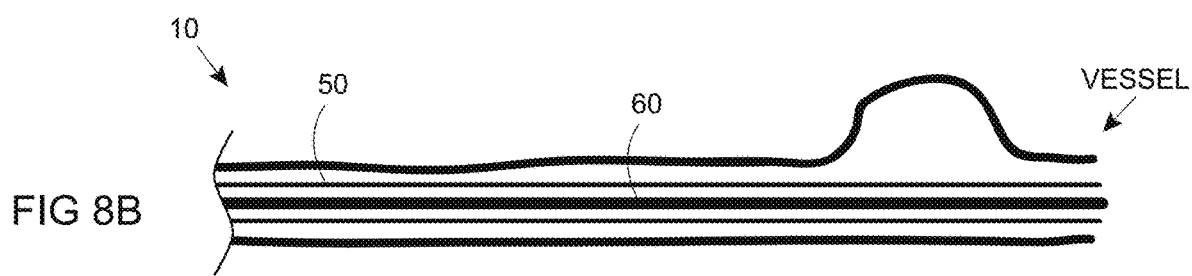
Figure 8C:
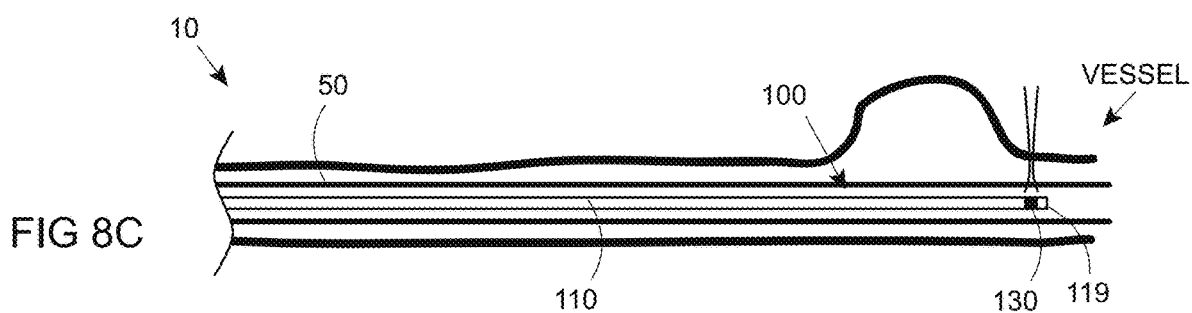
Figure 8D:
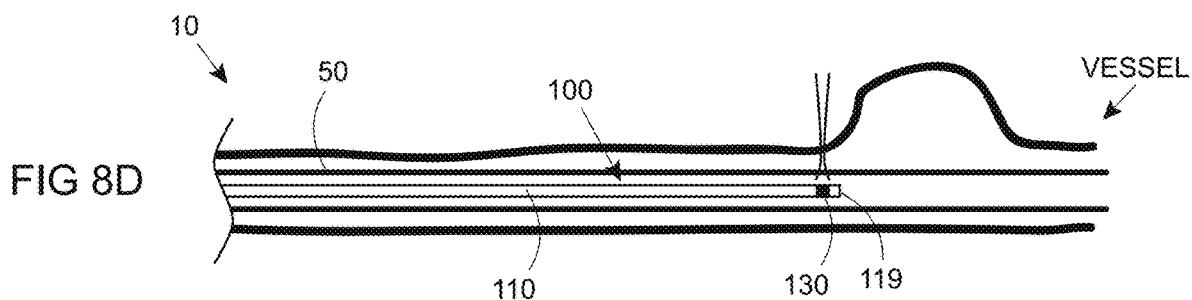

In FIG. 8B, the distal end of delivery catheter 50 has been advanced distal to and/or within patient site PS. In FIG. 8C, guidewire 60 has been removed, and probe 100 has been inserted through delivery catheter 50 such that its distal end 119 is proximate the distal end of delivery catheter 50. In some embodiments, probe 100 further includes spring tip 104 as described hereabove. Subsequently, image data is collected while retracting shaft 110 of probe 100 to the position shown in FIG. 8D. In these embodiments, the distal portion of the shaft of delivery catheter 50 can comprise a transparent segment, as described herebelow in reference to FIG. 9. The image data collected comprising image data of the blood, vessel wall and other tissue within patient site PS and/or image data of occlusive matter (e.g. thrombus or plaque) within patient site PS. In some embodiments, the image data further includes image data of an implant (e.g. implant 85 described herein), such as is described herebelow in reference to FIGS. 9A-C, and/or image data of a treatment device such as treatment device 91.

A flushing procedure (e.g. as described herein) can be performed through any delivery catheter 50, during one or more of Steps 8A-E. In some embodiments, a flushing procedure is at least performed during Step 8C, such as via delivery catheter 50 shown, or a more proximal delivery catheter 50 (not shown). In some embodiments, pullback of shaft 110 is initiated when adequate clearing is confirmed by analysis of image data collected by optical assembly 130 (e.g. an operator analysis of an image or an automated analysis performed by algorithm 240).

Figure 9A:
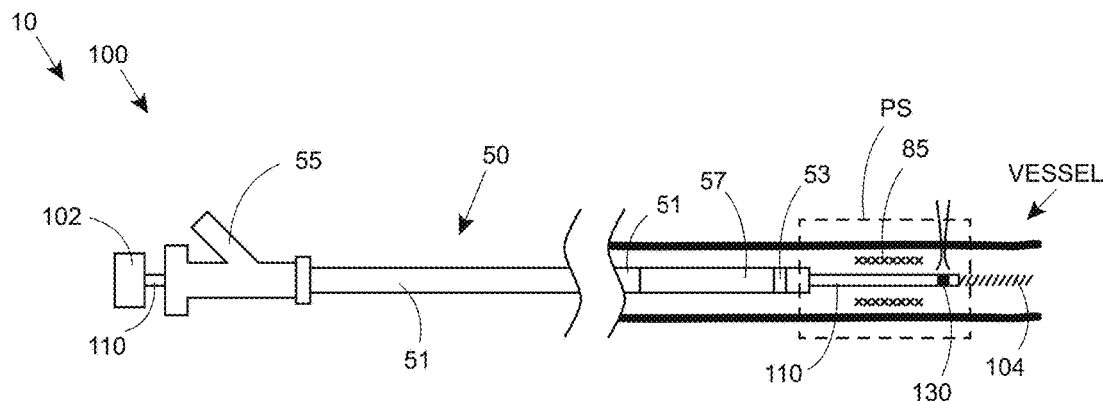
FIGS. 9A-C are schematic anatomical views of a series of steps for creating an image, including advancing a delivery catheter over an imaging probe into a patient site to be imaged, consistent with the present inventive concepts.
Figure 9B:
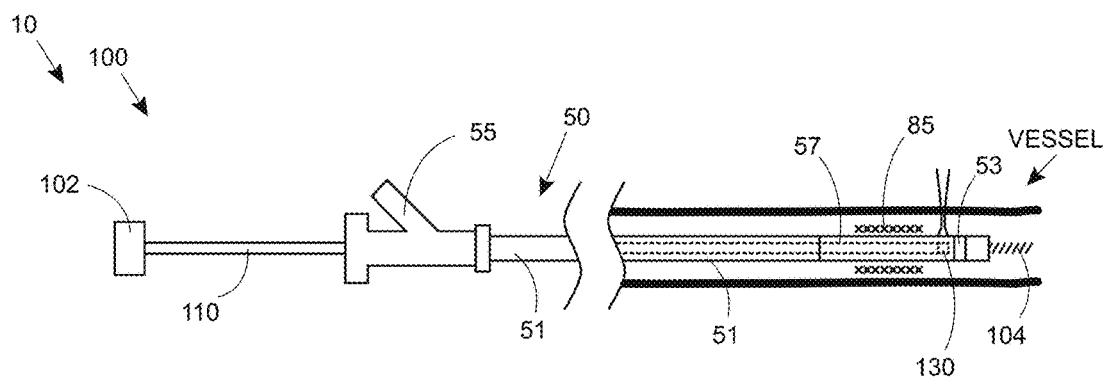
Figure 9C:
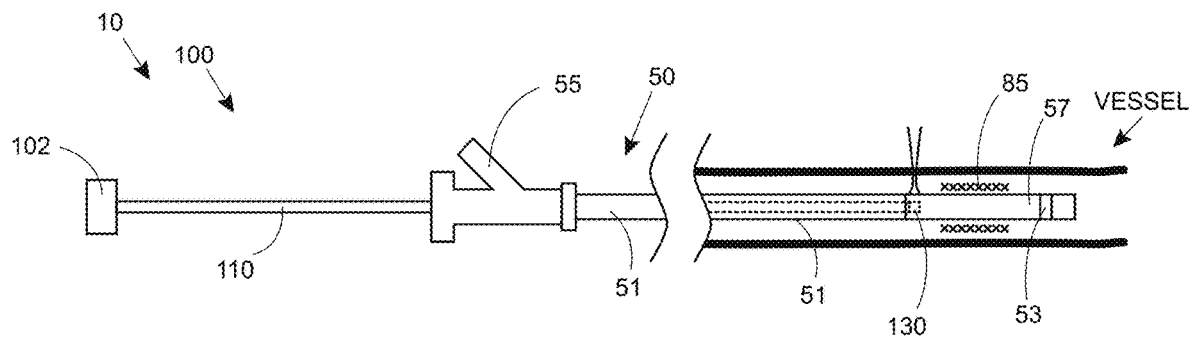

Referring now to FIG. 9A-C, schematic anatomical views of a series of steps for creating an image are illustrated, including advancing a delivery catheter over an imaging probe into a patient site PS to be imaged, consistent with the present inventive concepts. System 10 includes imaging probe 100, one or more delivery devices, such as at least one delivery catheter 50 and at least one guidewire 60 (not shown but such as is described hereabove in reference to FIG. 1), and implant 85. In some embodiments, system 10 comprises one or more similar components to system 10 described hereabove in reference to FIG. 1. In some embodiments, system 10 has been introduced into the patient as described hereabove in reference to FIG. 5, such as when delivery catheter 50 of FIG. 9A comprises one or more delivery catheters 50, such as one or more delivery catheters 50 including at least delivery catheter 50d of FIG. 5. In some embodiments, delivery catheter 50 comprises a transparent segment 57 in the distal portion of shaft 51, and/or a functional element 53 (e.g. a radiopaque marker), such as are described herebelow in reference to FIG. 11. Transparent segment 57 can comprise a length of up to 15 cm, such as a length of up to 10 cm, 5 cm, 2 cm or 1 cm.

In FIG. 9A, probe 100 has been inserted through delivery catheter 50 such that optical assembly 130 has passed beyond the distal end of delivery catheter 50 and is positioned within and/or distal to implant 85 (e.g. an implant for treating an aneurysm or a stenosis and/or one or more other implants as described hereabove in reference to FIG. 1). In Step 9B, delivery catheter 50 can be advanced such that transparent segment 57 is positioned around optical assembly 130 (e.g. optical assembly 130 is proximate the distal end of transparent segment 57). Subsequently, image data is collected while retracting shaft 110 of probe 100 to the position shown in FIG. 9C. The image data collected comprising image data of the blood, vessel wall and other tissue within patient site PS, image data of occlusive matter (e.g. thrombus or plaque) within patient site PS (e.g. an aneurysm, stenotic location, an implant location, a treatment device location and/or other patient site PS as described herein), and/or image data of implant 85. In some embodiments, probe 100 is retracted without the advancement of delivery catheter 50 shown in Step 9B.

A flushing procedure (e.g. as described herein) can be performed through any delivery catheter 50, during one or more of Steps 9A-E. In some embodiments, a flushing procedure is at least performed during Step 9C, such as via delivery catheter 50 shown, or a more proximal delivery catheter 50 (not shown). In some embodiments, pullback of shaft 110 is initiated when adequate clearing is confirmed by analysis of image data collected by optical assembly 130 (e.g. an operator analysis of an image or an automated analysis performed by algorithm 240).

Figure 10A:
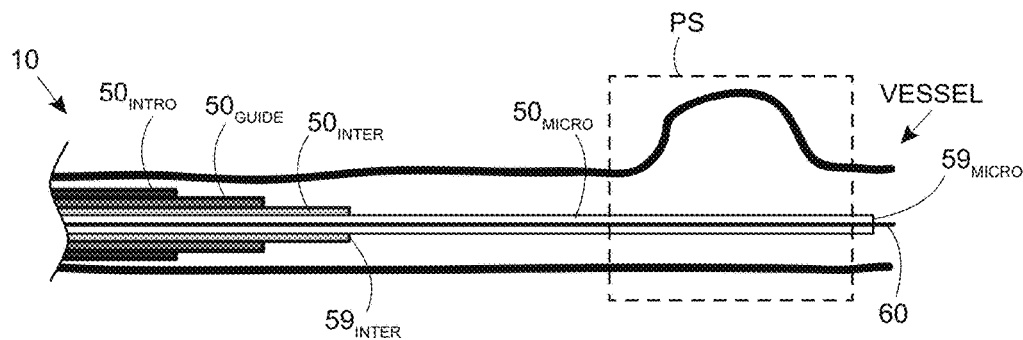
FIGS. 10A-E are schematic anatomical views of a series of steps for creating an image, including removing a smaller delivery catheter from a larger delivery catheter prior to inserting the imaging probe, consistent with the present inventive concepts.

Referring now to FIGS. 10A-E, a delivery catheter 50 is advanced over a smaller delivery catheter 50, after which the smaller delivery catheter 50 is removed from the lumen 52 of the larger delivery catheter 50 and probe 100 inserted in its place. System 10 includes imaging probe 100, one or more delivery devices, such as at least one delivery catheter 50 and at least one guidewire 60. As shown in FIG. 10A, delivery catheter $50_{MICRO}$ has been inserted into the larger delivery catheter $50_{INTER}$. (e.g. over guidewire 60 such as a guidewire with an OD of between 0.010" and 0.014"). Delivery catheter $50_{MICRO}$ has been advanced such that distal end $59_{MICRO}$ of delivery catheter $50_{MICRO}$ has passed through and beyond the distal end $59_{INTER}$ of delivery catheter $50_{INTER}$. (for example, such that distal end $59_{MICRO}$ is positioned within and/or beyond patient site PS). While patient site PS of FIGS. 10A-E is shown to include an aneurysm, alternatively or additionally patient site PS can comprise a site of a different patient disease or disorder, a site including an implant such as implant 85, a site including a patient treatment device such as treatment device 91 and/or any internal body location of the patient such as those described herein.

Figure 10B:
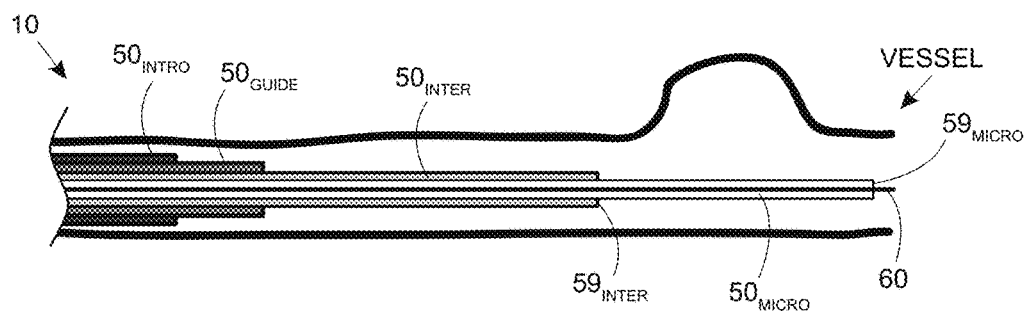
Figure 10C:
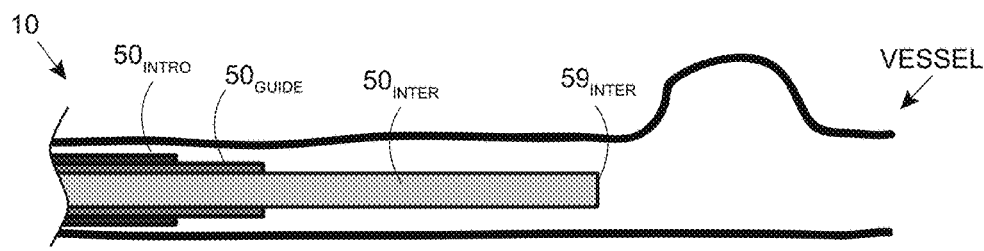
Figure 10D:
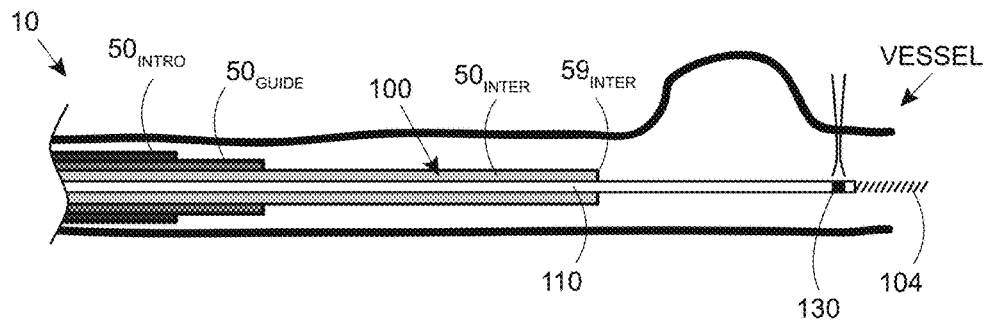
Figure 10E:
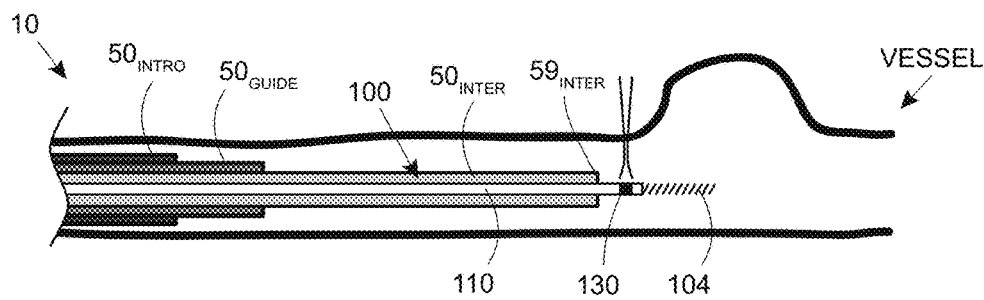

Delivery catheter $50_{INTER}$ can have already been inserted (as shown in FIG. 10A) through one or more other delivery catheters 50, such as when delivery catheter $50_{INTER}$ is inserted through a larger delivery catheter $50_{GUIDE}$, which has previously been inserted through a delivery catheter $50_{INTRO}$ comprising an introducer (e.g. a vascular introducer). In certain embodiments, delivery catheter $50_{INTER}$ is subsequently advanced over a smaller delivery catheter, delivery catheter $50_S$ (e.g. when delivery catheter $50_S$ is positioned over a guidewire 60), as shown in FIG. 10B. This subsequent advancement of the larger delivery catheter $50_L$ (over delivery catheter $50_S$) can provide a safer and/or more effective advancement of the delivery catheter $50_L$ than would have been accomplished by advancing the delivery catheter $50_L$ over guidewire 60 alone (without the benefit of support provided by delivery catheter $50_S$). The distal end $59_{INTER}$ of delivery catheter $50_{INTER}$ can be positioned at a location proximal to patient site PS (as shown), within patient site PS and/or distal to patient site PS. After the advancement of the delivery catheter $50_{INTER}$ over the delivery catheter $50_{MICRO}$, the smaller delivery catheter $50_S$, and if appropriate the surrounded guidewire 60, can be removed, as shown in FIG. 10C. Subsequently, probe 100 can be advanced through delivery catheter $50_{INTER}$, as shown in FIG. 10D, such as to a location within and/or just distal to patient site PS (e.g. optical assembly 130 is positioned within and/or just distal to patient site PS). The removal of delivery catheter $50_{MICRO}$ can be performed to accommodate a larger diameter probe 100 and/or to provide a larger space between probe 100 and the surrounding delivery catheter $50_{INTER}$ (e.g. to reduce the resistance encountered during a flushing procedure as described herein). In some embodiments, the probe 100 comprises an OD between 0.014" and 0.025", and the surrounding delivery catheter $50_L$ comprises an ID between 0.053" and 0.070". Shaft 110 of probe 100 can be retracted (e.g. after a flushing procedure has been initiated), and image data collected as optical assembly 130 translates to the proximal end of patient site PS, as shown in FIG. 10E. Flushing fluid (e.g. injectate 305 via injector 300) can be delivered in the space between probe 100 and delivery catheter $50_{INTER}$. Alternatively or additionally, flushing fluid can be delivered in the space between any two delivery catheters (e.g. in the space between delivery catheter $50_{GUIDE}$ and $50_{INTER}$, and/or in the space between $50_{INTRO}$ and $50_{GUIDE}$), via one or more ports 54 described hereabove.

Figure 11:
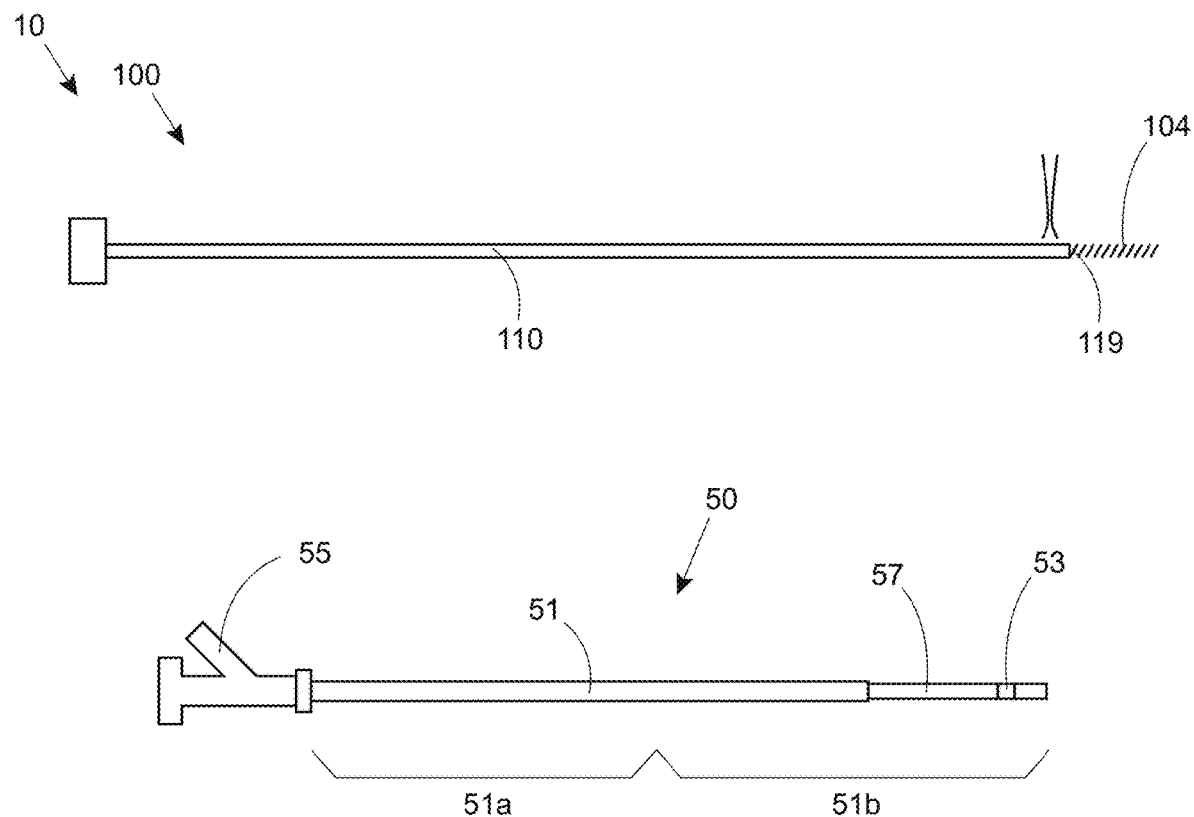
FIG. 11 is a schematic view of a system comprising an imaging probe and a delivery catheter comprising a shaft with a transparent segment, consistent with the present inventive concepts.

Referring now to FIG. 11, a schematic view of a system comprising an imaging probe and a delivery catheter comprising a shaft with a transparent segment is illustrated, consistent with the present inventive concepts. System 10 comprises imaging probe 100, which can be of similar construction and arrangement to imaging probe 100 described hereabove in reference to FIG. 1. System 10 further comprises one or more delivery devices, such as delivery catheter 50 shown. Probe 100 and delivery catheter 50 are constructed and arranged such that delivery catheter 50 can slidingly receive probe 100, as described herein. System 10 can further comprise other delivery devices, such as one or more additional delivery catheters and/or one or more guidewires (e.g. one or more guidewires constructed and arranged to support over-the-wire delivery of delivery catheter 50 and/or probe 100).

Delivery catheter 50 comprises an elongate shaft, shaft 51 comprising a proximal portion 51a and a distal portion 51b. In some embodiments, distal portion 51b comprises a smaller diameter than proximal portion 51a. In some embodiments, proximal portion 51a comprises an OD of approximately 0.024" and/or an ID of approximately 0.165". In some embodiments, distal portion 51b comprises an OD of approximately 0.022" and/or an ID of approximately 0.165". In some embodiments, distal portion 51b is more flexible than proximal portion 51a. Distal portion 51b comprises an optically transparent portion, transparent segment 57. Distal portion 51b and/or transparent segment 57 can comprise a length of at least 1 cm, such as a length of at least 2 cm, 3 cm, 4 cm, 5 cm, 7 cm or 10 cm. Delivery catheter 50 can comprise one or more functional elements, such as functional element 53 shown positioned in distal portion 51b. In some embodiments, functional element 53 comprises a visualizable marker, such as a marker selected from the group consisting of: a radiopaque marker; an ultrasonically reflective marker; a magnetic marker; a ferrous marker; and combinations of one or more of these.

In some embodiments, delivery catheter 50 comprises a connector 55 on its proximal end, such as a Touhy or other connector comprising a port (e.g. port 54 described hereabove) which can attach to a supply of fluids as described herein (e.g. a syringe, a power injector, and the like).

Figure 12:
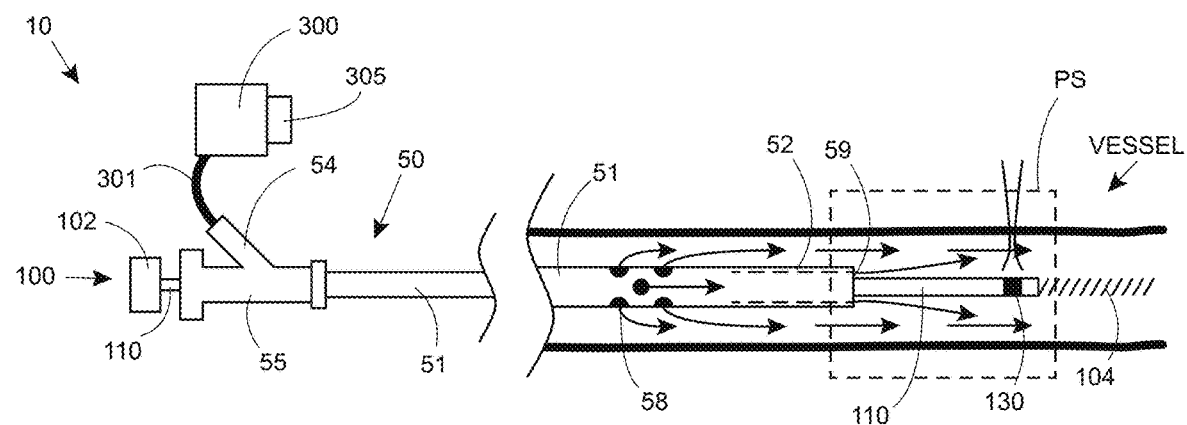
FIG. 12 is a schematic anatomical view of a system comprising an imaging probe and a delivery catheter including sideholes delivering a flushing fluid, consistent with the present inventive concepts.

Referring now to FIG. 12, a schematic anatomical view of a system comprising an imaging probe and a delivery catheter including sideholes delivering a flushing fluid is illustrated, consistent with the present inventive concepts. System 10 comprises probe 100 and at least one delivery catheter 50, each of which can be of similar construction and arrangement to the similar components described hereabove in reference to FIG. 1. The distal portions of delivery catheter 50 and probe 100 are shown in a magnified view (to the right of the page). Delivery catheter 50 and probe 100 have been inserted into the patient (such as in an interventional procedure including one or more delivery catheters 50 is described hereabove in reference to FIGS. 2, 5, 6A-E, 7A-E, 8A-D, 9A-C or 10A-E). Shaft 110 of probe 100 is advanced such that optical assembly 130 is positioned within or just distal to patient site PS. Patient site PS can comprise an aneurysm, stenotic location, an implant location, a treatment device location and/or other patient site PS as described herein. In some embodiments, optical assembly 130 is positioned distal to the distal end 59 of delivery catheter 50, as shown in FIG. 12 (such as to perform an image data collecting pullback procedure where optical assembly 130 remains outside of shaft 51 throughout the retraction).

System 10 further comprises injector 300, which can be configured to deliver one or more fluids to one or more delivery catheters 50 or other components of system 10. Port 54 of delivery catheter 50 is fluidly attached to injector 300 via tubing 301, such that fluid can be delivered in the space of lumen 52 that surrounds shaft 110 of probe 100 (e.g. the space between the outer wall of shaft 110 and the inner wall of shaft 51).

Just prior to image data collection, delivery of injectate 305 can be initiated by injector 300 propelling fluid into lumen 52 of shaft 51 (e.g. via tubing 301), such as to begin a flushing procedure to clear undesired material from locations surrounding optical assembly 130 (e.g. blood or other material that would prevent or at least limit image data collection by optical assembly 130). Injectate 305 is delivered to these locations via the distal end 59 of shaft 51 (distal end of lumen 52) and/or via sideholes 58. During image data collection (e.g. during rotation and retraction of optical assembly 130), delivery of injectate 305 by injector 300 continues. In some embodiments, a flushing procedure includes delivery of injectate 305 via both the distal end of shaft 51 and sideholes 58.

In some embodiments, delivery catheter 50 comprises multiple delivery catheters 50, one or more of which can include sideholes 58, and each of which can be used to deliver injectate 305 in a flushing or other fluid delivery procedure. Injectate 305 can comprise a contrast material (e.g. a ratio of radiopaque contrast and saline) such as to also allow fluoroscopic imaging of the patient site and neighboring areas.

Figure 13:
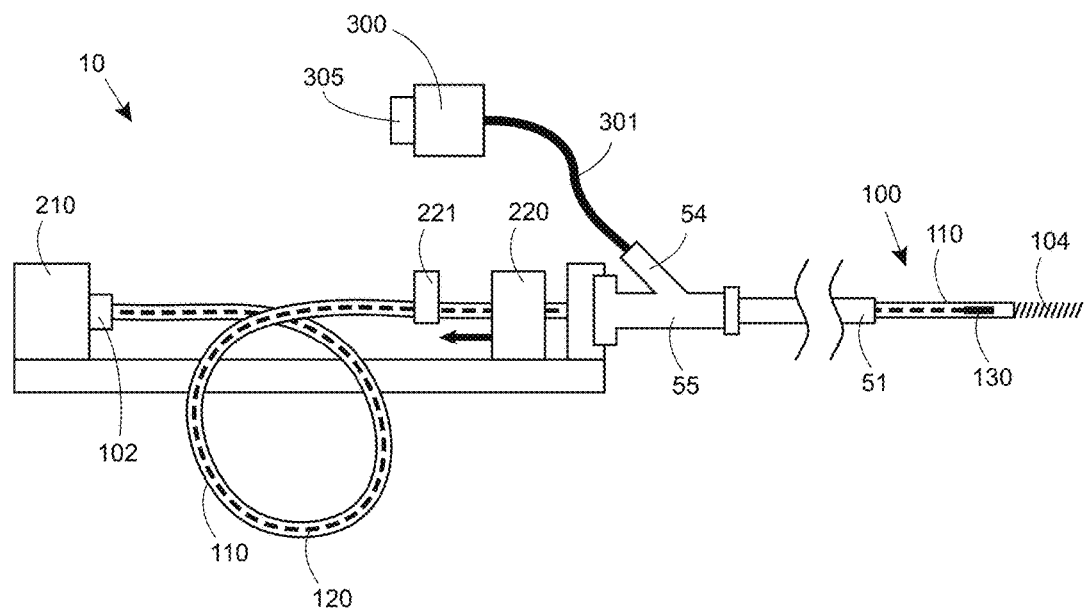
FIG. 13 is a schematic view of a system comprising an imaging probe, a rotating assembly and a retraction assembly, consistent with the present inventive concepts.

Referring now to FIG. 13, a schematic view of a system comprising an imaging probe, a rotating assembly and a retraction assembly is illustrated, consistent with the present inventive concepts. System 10 comprises probe 100, and a kit of delivery devices including multiple delivery catheters 50, and one or more guidewires 60. In some embodiments, system 10 comprises one or more similar components to system 10 described hereabove in reference to FIG. 1, such as those shown in FIG. 13. Imaging probe 100 is operatively connected to retraction assembly 220. Retraction assembly 220 can comprise a linear drive assembly constructed and arranged to cause translation (e.g. retraction and/or advancement) of shaft 110 of probe 100. In some embodiments, clamp 221 is removably attached to shaft 110 such that retraction assembly 220 can push against clamp 221 causing retraction of probe 100. Clamp 221 can also be manipulated by an operator, such as to advance, retract, and/or twist shaft 110 of probe 100, (e.g. to assist a user in advancing probe 100 to a patient site). Clamp 221 can be loosened and/or tightened around shaft 110, such that clamp 221 can be repositioned along the length of shaft 110.

In some embodiments, clamp 221 and retraction assembly 220 are constructed and arranged such that during a pullback of shaft 110, retraction assembly 220 pushes against clamp 221, and shaft 110 is retracted. After the pullback is complete, retraction assembly 220 can return to its starting position without advancing shaft 110 (as clamp 221 is not fixed to retraction mechanism 220).

Imaging probe 100 is also operatively connected to rotating assembly 210. Rotating assembly 210 comprises a motor and/or other rotating mechanisms used to rotate core 120 (e.g. and also optical assembly 130). Rotating assembly 210 and retraction assembly 220 can be of similar construction and arrangement to similar assemblies used in commercial catheter-based OCT systems. One or more components of system 10 can be disposable and/or reusable. Reusable components of system 10 can be configured to be resterilizable.

Referring now to FIG. 14, a schematic anatomical view of an imaging probe in a side-by-side configuration with a second device is illustrated, consistent with the present inventive concepts. System 10 includes imaging probe 100, one or more delivery devices, such as at least one delivery catheter 50 and at least one guidewire 60 (not shown but such as is described hereabove in reference to FIG. 1), and a device to treat and/or diagnose the patient, such as implant delivery device 80 or treatment device 91 described hereabove. Device 80/91 can be configured to deliver implant 85 (e.g. a coil as shown, a stent and/or a covered stent). In some embodiments, imaging probe 100, device 80/91 and/or other component of system 10 is of similar construction and arrangement to a similar component of system 10 described hereabove in reference to FIG. 1, such as when imaging probe 100 comprises shaft 110, optical assembly 130 and/or spring tip 104 shown. In some embodiments, system 10 has been introduced into the patient as described hereabove in reference to FIG. 5, such as when delivery catheter 50 of FIG. 14 comprises one or more delivery catheters 50, such as one or more delivery catheters 50 including at least delivery catheter 50d of FIG. 5. Delivery catheter 50 comprises shaft 51 and lumen 52. In some embodiments, system 10 has been introduced into the patient as described herebelow in reference to FIG. 15, such as when imaging probe 100 and device 80/91 are in the side-by-side configuration within lumen 52 as shown in FIG. 14. Optical assembly 130 and the distal end of device 80/91 are each positioned proximate patient site PS, such that a diagnostic procedure (e.g. a biopsy) and/or a treatment procedure (e.g. placement of a coil or other implant 85) can be performed using device 80/91, with imaging probe 100 collecting image data prior to, during and/or after the diagnosis and/or treatment by device 80/91.

Referring additionally to FIG. 15, a flow chart of a method of creating an image using an imaging probe in a side-by-side configuration with a second device is illustrated, consistent with the present inventive concepts. Method 1500 of FIG. 15 shall be described using system 10 and its components as described hereabove. In Step 1505, a delivery catheter $50_{MICRO}$, such as a microcatheter with an ID of between 0.0165" and 0.027", is advanced over a guidewire 60 to a location proximate patient site PS (e.g. a neural site or a cardiac site as described hereabove). In some embodiments, guidewire 60 is delivered distal to patient site PS, such as at a location just distal to an aneurysm neck or just distal to thrombus or other occlusive matter. Delivery catheter $50_{MICRO}$ and guidewire 60 can be inserted through one or more, larger delivery catheters, such as delivery through an introducer catheter such as catheter $50_{INTRO}$ described hereabove.

In Step 1510, delivery catheter $50_{MICRO}$ is removed, leaving guidewire 60 in place (e.g. when guidewire 60 comprises an exchange length guidewire).

In Step 1515, a larger diameter catheter, delivery catheter $50_{INTER}$, is advanced to patient site PS over guidewire 60. Catheter $50_{INTER}$ can comprise a delivery catheter with an ID of between 0.050" and 0.085", an ID between 0.053" and 0.072", or an ID between 0.070" and 0.072".

In Step 1520, guidewire 60 is removed from delivery catheter $50_{INTER}$ (e.g. removed from a lumen of delivery catheter $50_{INTER}$).

In Step 1525, a first device (e.g. a device with an OD less than 0.035") is advanced through a lumen of delivery catheter $50_{INTER}$, and in Step 1530, a second device (e.g. a device with an OD less than 0.035") is advanced through a lumen of delivery catheter $50_{INTER}$ (e.g. the same lumen). In some embodiments, the first device comprises a diagnostic and/or treatment device (e.g. device 80 and/or 91 described hereabove, device 80/91), and the second device comprises imaging probe 100 (i.e. imaging probe 100 is advanced after device 80/91). Alternatively, the first device comprises imaging probe 100 and the second device comprises a diagnostic and/or treatment device (e.g. device 80/91). In some embodiments, imaging probe 100 comprises an OD less than 0.020", such as an OD less than or equal to 0.0165". In these embodiments, device 80/91 comprises an OD (e.g. an OD less than or equal to 0.035", 0.030", 0.025" or 0.020") configured to be slidingly translated within delivery device $50_{INTER}$ while imaging probe 100 is positioned within the same lumen of delivery device $50_{INTER}$ (e.g. while probe 100 is similarly translated within the lumen of delivery device $50_{INTER}$).

In Step 1535, optical assembly 130 of imaging probe 100 is positioned at a desired location, such as a location within or otherwise proximate an occlusion or an aneurysm. An implant (e.g. implant 85) and/or other diagnostic or treatment portion of device 80/91 (e.g. a distal portion) can be positioned proximate the desired location as well, such as is shown in FIG. 14.

In Step 1540, a fluoroscopic procedure is performed in which a desired location of optical assembly 130 is confirmed or achieved (e.g. via repositioning). A desired location of the diagnostic or treatment portion of device 80/91 can be confirmed or achieved as well. In some embodiments, a small bolus (e.g. 10 ml or less) of fluid including a contrast agent is introduced (e.g. through delivery catheter $50_{INTER}$), such as to enhance fluoroscopic visualization of patient site PS, device 80/91 and/or imaging probe 100.

In Step 1545, one or more imaging parameters of system 10 (e.g. as described herein) are set, such as by a clinician performing the imaging procedure. In some embodiments, console 200 of system 10 is set to a preview mode as described herein. Console 200 can be configured to be set in automatic, semi-automatic and/or manual modes (e.g. modes in which one or more imaging parameters are automatically, semi-automatically and/or manually adjusted). Console 200 can be configured to capture image data relatively continuously or intermittently.

System 10 can be configured to deliver flush material during image data capture, such as injectate 305 delivered via injector 300 as described hereabove in reference to FIG. 1. In some embodiments, console 200 is set in a continuous image data capture mode, and injectate 305 can be delivered for approximately 30 seconds at a flow rate of between 2 ml/sec and 3 ml/sec. In some embodiments, console 200 is set in an intermittent data capture mode, and injectate 305 can have a delivery profile approximating flushing every 10 seconds for a 2 second duration, such as when injectate 305 is delivered at 3 ml/sec to 4 ml/sec. In some embodiments, console 200 is configured to automatically detect delivery of injectate 305, and to place time-stamps on the image data collected (e.g. time stamps relative to the timing of injectate 305 delivery). In some embodiments, console 200 is configured to control the delivery of injectate 305 via injector 300, such as an automatic, semi-automatic and/or manual control as described hereabove.

In some embodiments, console 200 is configured to collect image data in a manual mode. In these embodiments, injectate 305 can be delivered in small boluses, and delivery of injectate 305 (e.g. by injector 300) can be detected and/or controlled by console 200, such as to place time-stamps on the image data collected as described hereabove.

In Step 1550, using the device 80/91, a clinical procedure (e.g. a diagnostic and/or therapeutic procedure) is performed. Prior to, during and/or after performance of the clinical procedure, system 10 collects image data (e.g. via retraction of optical assembly 130 as described hereabove). In some embodiments, device 80/91 comprises a catheter configured to deliver one or more coils (e.g. occlusive coils configured to treat an aneurysm). In some embodiments, device 80/91 comprises a stentriever or other thrombus removal device. In some embodiments, device 80/91 comprises a stent delivery device, such as a covered stent delivery device.

In Step 1555, the image data collected by system 10 is reviewed, such as by the clinician performing the clinical and/or imaging procedure.

In Step 1560, an assessment of the image data is performed to determine if additional diagnosis and/or treatment is required or at least desired. The assessment can comprise a review of a 2D and/or 3D image of the patient site PS prior to, during and/or after the clinical procedure. Alternatively or additionally, the assessment can comprise a review of a 2D and/or 3D image of any implants (e.g. one or more implants 85) implanted in the patient during the procedure, such as to determine sufficient occlusion (e.g. sufficient occlusion of an aneurysm by implantation of coils or a covered stent), adequate positioning and/or apposition of an implant with tissue, adequate flow through a native vessel, and combinations of one or more of these.

If additional diagnosis and/or treatment is not desired, Step 1570 is performed in which the devices are removed from the patient and the procedure is complete.

If additional diagnosis and/or treatment is desired, Step 1565 is performed in which additional diagnosis and/or treatment is performed, such that Steps 1555, 1560 and 1565 are repeated until a desired result is achieved. Additional treatment can include implantation of one or more additional implants (e.g. additional coils implanted), additional dilation of an implant (e.g. dilation of a stent to improve apposition with tissue), and other treatments as described herein.

In some embodiments, in addition to Step 1550, image data is collected by system 10 in any one or more of Steps 1535 through 1550. In some embodiments, image data is collected while optical assembly 130 is retracted approximately 20 mm, which can be followed by an automated or manual advancement to the starting location or other position proximate a distal portion of patient site PS.

A flushing procedure (e.g. as described herein) can be performed through any delivery catheter 50, during one or more of Steps of method 1500 of FIG. 15. In some embodiments, a flushing procedure is at least performed during capture of image data (e.g. during rotation and/or retraction of optical assembly 130), such as via delivery catheter 50$_{INTER}$, or a more proximal delivery catheter 50. In some embodiments, pullback of optical assembly 130 (e.g. pullback of shaft 110) is initiated when adequate clearing is confirmed by analysis of image data collected by optical assembly 130 (e.g. an operator analysis of an image or an automated analysis performed by algorithm 240 of console 200).

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the inventive concepts, and variations of aspects of the inventive concepts that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. A method of creating an image comprising:
   (a) selecting an imaging probe;
   (b) selecting at least one delivery device;
   (c) advancing a first delivery device within a blood vessel of a patient, wherein the first delivery device comprises a first delivery catheter comprising a distal end;
   (d) advancing the imaging probe within the first delivery catheter such that an optical assembly of the imaging probe is proximate a patient site;
   (e) retracting the elongate shaft of the imaging probe and collecting image data of the patient site during the retraction;
   (f) creating one or more images based on the collected image data; and
   (g) advancing a distal end of a diagnostic and/or treatment device through the first delivery catheter while the imaging probe resides within the first delivery catheter, such that the distal end of the diagnostic and/or treatment device is positioned proximate the patient site during the retraction of the elongate shaft.

2. The method according to claim 1, wherein the first delivery catheter comprises an inner diameter (ID) between 0.050" and 0.085".

3. The method according to claim 1, further comprising:
   performing a clinical procedure with the diagnostic and/or treatment device;
   performing an assessment of the image data; and
   determining if an additional clinical procedure is desired based on the image data.

4. The method according to claim 3, wherein the assessment of the image data comprises a review of a two-dimensional (2D) and/or three-dimensional (3D) image of the patient site prior to, during and/or after the clinical procedure.

5. The method according to claim 3, wherein the assessment of the image data comprises a review of a 2D and/or 3D image of any implants implanted in the patient during the procedure.

6. The method according to claim 3, further comprising:
   performing an additional clinical procedure; and
   collecting additional image data related to the additional clinical procedure.

7. The method according to claim 6, wherein the additional clinical procedure comprises a procedure selected from the group consisting of: implantation of one or more additional implants; additional dilation of an implant; and combinations thereof.

8. The method according to claim 1, wherein the optical assembly is positioned distal to the distal end of the first delivery catheter during the collection of the image data.

9. The method according to claim 1, wherein the patient site comprises a blood vessel selected from the group consisting of: artery of the patient's neck; vein of the patient's neck; artery of the patient's head; vein of the patient's head; artery of the patient's brain; vein of the patient's brain; and combinations thereof.

10. The method according to claim 1, wherein step (e) further comprises collecting image data of an implanted device proximate the patient site, and wherein the image created in step (f) further comprises one or more images of the implanted device.

11. The method according to claim 10, wherein step (e) further comprises collecting image data of an implant placement procedure, and wherein the image created in step (f) further comprises creating one or more images of the implant placement procedure.

12. The method according to claim 10, wherein step (e) further comprises collecting image data of a treatment device, and wherein the image created in step (f) further comprises creating one or more images of the treatment device.

13. The method according to claim 12, wherein step (f) further comprises creating one or more images of a treatment procedure.

14. The method according to claim 1, wherein the first delivery catheter comprises a proximal end, a distal end, and a lumen therebetween, wherein the imaging probe is advanced within the first delivery catheter.

15. The method according to claim 14, wherein during step (b) the distal end of the first delivery catheter is advanced to a location proximal to the patient site, and wherein during the collection of image data in step (e) the optical assembly remains distal to the first delivery catheter distal end.

16. The method according to claim 1, wherein the first delivery catheter comprises a distal portion including one or more sideholes, wherein the method further comprises delivering injectate in a flushing procedure through the one or more sideholes.

17. The method according to claim 1, wherein the first delivery catheter is advanced to a location proximate the patient site, and wherein the method comprises advancing the imaging probe optical assembly beyond the distal end of the first delivery catheter.

18. The method according to claim 1, further comprising implanting an implantable device.

19. The method according to claim 18, wherein the patient site comprises the implanted device or a site in which the implanted device will be implanted, the method comprising:
   advancing the optical assembly of the imaging probe to the patient site;
   collecting image data of the patient site;
   analyzing the image data collected; and
   implanting the implantable device based on the analysis.

20. The method according to claim 19, wherein the analysis modifies an implantation parameter selected from the group consisting of: selection of the implantable device; selection of the implantable device porosity; selection of the implantable device metal coverage; selection of the implantable device pore density; selection of the implantable device diameter; selection of the implantable device length; selection of the location to implant the implantable device; a dilation parameter for expanding the implantable device once implanted; a repositioning of the implantable device once implanted; selection of a second implantable device to be implanted; and combinations thereof.

21. The imaging method according to claim 18, wherein the method comprises:
   accessing the patient site with the optical assembly;
   collecting image data of the implanted device;
   analyzing the image data and identifying at least one implantation issue; and
   adjusting the implantation of the implanted device.

22. The imaging method according to claim 21, wherein the implantation issue identified comprises an issue selected from the group consisting of: malposition of implanted device; inadequate deployment of implanted device; presence of air bubbles; and combinations thereof.

23. The method according to claim 1, wherein the diagnostic and/or treatment device comprises an OD less than or equal to 0.035".

24. The method according to claim 1, wherein the imaging probe comprises an OD of less than 0.025".

25. The method according to claim 1, wherein the imaging probe comprises an OD of less than 0.018".

* * * * *